United States Patent
Li et al.

(10) Patent No.: US 11,596,693 B2
(45) Date of Patent: Mar. 7, 2023

(54) ANTIBODY-DRUG CONJUGATES AND USES THEREOF

(71) Applicant: MABPLEX INTERNATIONAL CO., LTD., Shandong (CN)

(72) Inventors: Lele Li, Shandong (CN); Changjiang Huang, Shandong (CN); Youxiang Sun, Shandong (CN); Lina Liu, Shandong (CN)

(73) Assignee: MABPLEX INTERNATIONAL CO., LTD, China (Shandong) Pilot Free Trade Zone (CN)

( * ) Notice: Subject to any disclaimer, the term of this patent is extended or adjusted under 35 U.S.C. 154(b) by 311 days.

(21) Appl. No.: 16/650,226

(22) PCT Filed: Oct. 23, 2019

(86) PCT No.: PCT/CN2019/112663
§ 371 (c)(1),
(2) Date: Mar. 24, 2020

(87) PCT Pub. No.: WO2021/022678
PCT Pub. Date: Feb. 11, 2021

(65) Prior Publication Data
US 2021/0228728 A1    Jul. 29, 2021

(30) Foreign Application Priority Data
Aug. 7, 2019    (CN) .......................... 201910723947.8

(51) Int. Cl.
A61K 47/68    (2017.01)

(52) U.S. Cl.
CPC ...... *A61K 47/6801* (2017.08); *A61K 47/6855* (2017.08); *A61K 47/6889* (2017.08)

(58) Field of Classification Search
None
See application file for complete search history.

(56) References Cited

U.S. PATENT DOCUMENTS

| | | |
|---|---|---|
| 2015/0105540 A1 | 4/2015 | Miao et al. |
| 2015/0366985 A1* | 12/2015 | Brown ............... A61K 31/4709 530/331 |
| 2016/0324984 A1 | 11/2016 | Brinkmann et al. |
| 2016/0346402 A1* | 12/2016 | Lerchen ............. C07K 16/2863 |
| 2018/0125988 A1 | 5/2018 | Yang |
| 2018/0169262 A1 | 6/2018 | Lu et al. |
| 2019/0321483 A1 | 10/2019 | Wen et al. |

FOREIGN PATENT DOCUMENTS

| | | |
|---|---|---|
| CN | 106132431 | 11/2016 |
| CN | 107207564 | 9/2017 |
| CN | 108201625 | 6/2018 |
| CN | 108853514 | 11/2018 |
| CN | 109106951 | 1/2019 |
| CN | 110099697 | 8/2019 |
| WO | WO 2013/160453 | 10/2013 |
| WO | WO 2016/077505 | 5/2016 |
| WO | WO 2018/112253 | 6/2018 |
| WO | WO 2019/034176 | 2/2019 |
| WO | WO 2019/127607 | 7/2019 |

OTHER PUBLICATIONS

Huang et al., Chem. Commun., 2019, 55, 5175 (Year: 2019).*
Database Caplus Chemical Abstracts Service, Columbus, Ohio, US; Database Accession No. 2019:684370. Abstract of Huang et al., Chem. Commun., 2019, 55, 5175 (Year: 2019).*
Database Caplus Chemical Abstracts Service, Columbus, Ohio, US; Database Accession No. 2015:1095156, Abstract of U.S. Publication No. 20160346402, Bayer Pharma Aktiengesellschaft, Germany, Lerchen et al., (Year: 2015).*
Extended European Search Report issued in European Patent Application No. 19861250.9, dated Sep. 23, 2021.
English translation of Office Communication issued in Chinese Patent Application No. Aug. 26, 2020, dated Aug. 26, 2020.
Office Communication issued in Canadian Patent Application No. 3,076,712, dated Apr. 8, 2021.
English Translation of PCT International Search Report and Written Opinioni issued in International Application No. PCT/CN2019/112663, dated Jul. 22, 2020.
Fang et al., "Structurally Defined αMHC-II Nanobody-Drug Conjugates: A Therapeutic and Imaging System for B-Cell Lymphoma," *Angew. Chem. Int. Ed.*, 55:2416-2420, 2016.
Office Communication issued in Australian Patent Application No. 2019341066, dated Sep. 28, 2020.

* cited by examiner

Primary Examiner — Karl J Puttlitz
(74) Attorney, Agent, or Firm — ParkerHighlander PLLC

(57) ABSTRACT

Provided is an antibody-drug conjugate (ADC) using one or more cysteine or derivatives thereof as linkers to couple one or more drugs at the limited binding sites of an antibody, making it possible to produce an ADC product with high drug payload, or to choose a drug with less toxicity, thereby obtaining an ADC product with wide therapeutic window. In addition, since a plurality of drugs may be coupled to one binding site, the ADC products obtained by the method of the present disclosure have better uniformity in the case of same DAR value. Moreover, the amount of antibody required for production may be greatly reduced, thereby lowering the cost. Compared with the antibody-drug conjugates coupled only one drug, the antibody-drug conjugates produced by the method of the present disclosure have the same inhibition or killing effect on tumor cells while using fewer drugs for coupling to the same site.

19 Claims, No Drawings

ANTIBODY-DRUG CONJUGATES AND USES THEREOF

This application is a national phase application under 35 U.S.C. § 371 of International Application No. PCT/CN2019/112663, filed Oct. 23, 2019, which claims priority to Chinese Patent Application No. 201910723947.8, filed Aug. 7, 2019, the disclosures of which are hereby incorporated by reference in their entirety.

FIELD

The present disclosure relates to the field of biomedicine, and in particular to an antibody-drug conjugate using one or more cysteine residues or derivatives thereof as a linker and uses thereof, and the linker may load one or more drugs at a limited binding site of the antibody as desired.

BACKGROUND

Antibody-drug conjugate (ADC) refers to a class of biological drugs that an active drug is linked with an antibody via a chemical linker. ADCs are like a precision-guided weapon system, in which the active drug is used as an ammunition to accurately kill diseased cells under the guidance of the antibody. Therefore, ADCs combine the dual advantages of high potency of cytotoxic drugs and high targeting of antibodies. By the end of July 2019, only six antibody-conjugated drugs have been approved worldwide (Table 1).

TABLE 1

Marketed antibody-drug conjugates

| Generic name of drugs | Companies | Time to market | Indication |
| --- | --- | --- | --- |
| Brentuximab vedotin | Seattle, Takeda | 2011 | Hodgkin's lymphoma |
| Trastuzumab emtansine | Genentech | 2013 | Breast cancer |
| Inotuzumab ozogamicin | Pfizer | 2017 | Acute lymphoblastic leukemia |
| Gemtuzumab ozogamicin | Pfizer | 2017 | Acute myeloid leukemia |
| Moxetumomab pasudotox | AstraZeneca | 2018 | Hairy cell leukemia |
| Polatuzumab vedotin-piiq | Genentech | 2019 | Diffuse large B cell lymphoma |

Due to the non-uniqueness of the selected binding sites on the antibody and the complexity of the ligation reaction, the actual resulting ADC product is an ADC mixture containing different amounts of antibodies linked with different amounts of drugs at different sites. The heterogeneity of the ADC drug production makes it a great challenge to the production and quality control of drugs. When considering product uniformity, there is an important indicator, that is, DAR value (drug-to-antibody ratio), which is the average number of drugs that can be carried by a unit number of antibody. If the DAR value is too small, the drug molecules carried by antibody are too little, which may affect the overall drug efficacy. However, if the average DAR value is too high, the antibody is loaded with too many drug molecules, which leads the ADC as a whole unstable, change the pharmacokinetic parameters, and may increase the plasma clearance, shorten half-life, and increase systemic drug toxicity.

At present, there are three classical coupling methods for ADCs, one is amide coupling, the other one is thiol coupling, and the third one is cross-linking.

Amide coupling is to couple a drug to a lysine (Lys) residue of an antibody via a linker. The first generation of the ADC drug Mylotarg adopts such a way of amide coupling. There are nearly one hundred lysine in IgG, the coupling may happen on nearly 40 exposed lysine residues on the light chain and heavy chain of the antibody, and each antibody may be coupled with a number of drug molecules at different amounts via lysine coupling. Therefore, the ADCs obtained by amide coupling are highly heterogeneous, and the product has extremely poor uniformity, which seriously affects the PK/PD and therapeutic window of the drug (see http://www.sohu.com/a/277791166_464404).

In thiol coupling, an interchain disulfide bond of an antibody is first broken to form a free cysteine (Cys) residue, which is further coupled with a linker-drug complex capable of matching cysteine residue. Since there are only 4 pairs of interchain disulfide bonds in IgG, 8 free cysteine residues may be formed after all interchain disulfide bonds have been broken, thus the average DAR of ADCs obtained by monothiol coupling is 0-8. Although thiol coupling may give better control to the number of drugs on each antibody, the breakage of the interchain disulfide bond greatly reduces the stability of the antibody.

Cross-linking is a new type of coupling which is developed on the basis of thiol coupling. Like thiol coupling, an interchain disulfide bond of the antibody is first broken to form two free residues, which are further coupled simultaneously. Since there are only 4 pairs of interchain disulfide bonds on one antibody, there are 8 free cysteine residues after the interchain disulfide bonds are all broken, thus the ADCs formed by bridge coupling have an average DAR of 0-4. Compared with thiol coupling, bridge coupling may give better control to the homogeneity of the product, and can greatly provide stability of the antibody after coupling. However, the DAR of the bridge coupling is up to 4, that is, up to 4 drugs may be coupled to one antibody. The number of antigens on the surface of tumor cells is limited, and the antigen expression level required for effective ADC activity varies depending on the characteristics of different antigens. ADC requires at least $1\times10^4$ antigens/cell to ensure the delivery of a lethal amount of cytotoxic drug. Ideally, the antigen targeted by the antibody of the ADC should be evenly expressed on the surface of the tumor cells with a high copy number ($>10^5$/cell). Tumor cells usually have a limited number of antigens on their surface (approximately 5,000 to $10^6$ antigens/cell), while ADCs have an average DAR of 3.5-4 (e.g., Brentuximab vedotin has an average DAR of 4 and Trastuzumab emtansine has an average DAR of 3.5), which makes the amount of drug delivered to tumor cells is very low, giving a less effect on tumor cells. This is considered to be one of the main reasons of clinical failure of ADCs.

Based on the limited number of antigens on the surface of tumor cells, in order to ensure that a limited number of drugs carried by antibodies can effectively kill tumor cells, small molecules with particularly strong toxicity are often used in clinic. At present, the small molecules used in ADCs mainly include classes of auristatin, maytansine, calicheamicin, doxorubicin, etc. These small molecules have a stronger killing effect on cancer cells as compared with traditional chemotherapy drugs. Typically, killing of target cells may be achieved by an dose of four to six molecules on average. However, once these highly toxic small molecule drugs are off-targeted in the body, they are fatal to the patient. In addition, since these small molecules are particularly toxic (e.g., DM1 has an $IC_{50}$ of about $10^{-11}$ mol/L for many cells, DM4 has an $IC_{50}$ of about $10^{-12}$ mol/L (Ref. 1: Widdison W C, Wilhelm S D, Cavangh E E, et al. Semisynthetic maytansine analogues for the targeted treatment of cancer [J]. J Med Chem, 2006, 49: 4392-4408; Ref. 2: Lambert J M. Antibody-maytansinoid conjugates: a new strategy for the treatment of Cancer [J]. Drugs Future, 2010, 35: 471-480.), and MMAE has an $IC_{50}$ about $10^{-11}$-$10^{-9}$ mol/L). If there are conditions such as off-target and early drug release, there will be a very big risks for the patients. The FDA has conducted a pooled analysis of 20 investigational new drugs (INDs) and found that the toxicity of ADC drugs in animals is mainly hematopoietic toxicity, hepatotoxicity and reproductive toxicity, and some of them also have skin toxicity and nephrotoxicity, wherein the hematopoietic toxicity, hepatotoxicity and reproductive toxicity are directly related to small molecule cytotoxic drugs (Ref. 3: Saber H, Leighton J K. An FDA oncology analysis of antibody-drug conjugates [J]. Regul Toxicol Pharmacol, 2015, 71(3): 444-452). However, if a small molecule drug with low toxicity is used, the amount of small molecule drug as payload is often too low, so that the generated drug effect is too low, leading to clinical failure.

SUMMARY

In order to solve the above problems, the present disclosure provides a novel antibody-drug conjugate capable of coupling more active drugs, and the technical solutions of the present disclosure are as follows.

The present disclosure provides an antibody-drug conjugate represented by formula (I) to (IV):

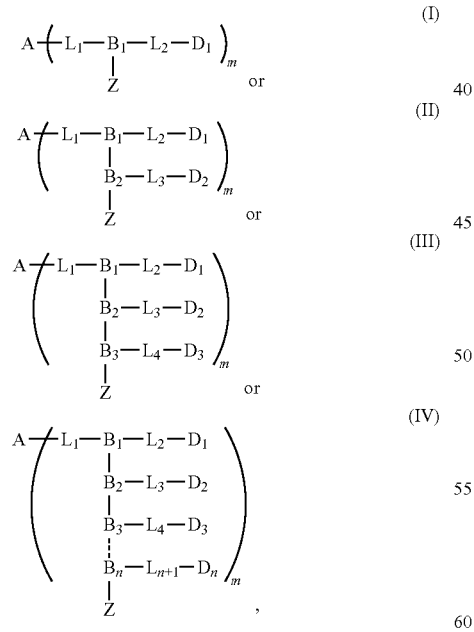

wherein,
  A is an antibody or a functional binding fragment thereof;
  $B_1$, $B_2$, $B_3$, . . . , and $B_n$ are cysteine or a derivative thereof, which may be the same or different; $B_1$ and $B_2$, $B_2$ and $B_3$, . . . , $B_{n-1}$ and $B_n$ are linked via a peptide bond through a dehydration condensation reaction;
  $L_1$, $L_2$, $L_3$, $L_4$, . . . , and $L_{n+1}$ are each independently a linker, which may be the same or different; $L_1$ is covalently linked to the amino terminus of $B_1$, $L_2$ and $B_1$, $L_3$ and $B_2$, $L_4$ and $B_3$, . . . , $L_{n+1}$ and $B_n$ are covalently linked via a thiol group, and $L_2$ and $D_1$, $L_3$ and $D_2$, $L_4$ and $D_3$, . . . , $L_{n+1}$ and $D_n$ are covalently linked;
  $D_1$, $D_2$, $D_3$, . . . , and $D_n$ are each independently an active drug, which may be the same or different;
  Z is a group covalently linked to the carbonyl group of $B_1$ in formula (I), the carbonyl group of $B_2$ in formula (II), the carbonyl group of $B_3$ in formula (III) or the carbonyl group of $B_n$ in formula (IV);
  n is an integer greater than or equal to 4, which represents the number of branches linking to the active drugs; and
  m is selected from 1, 2, 3, 4, 5, 6, 7 and 8.

Further, the structures of $B_1$, $B_2$, $B_3$, . . . , $B_n$ are represented by formula (V) respectively:

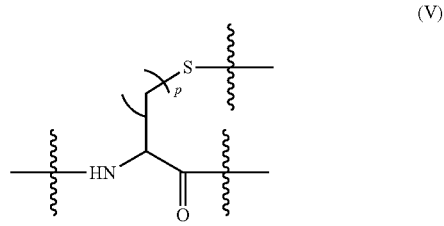

wherein p is selected from 1, 2, 3, 4, 5, 6, 7 and 8.
Further, Z is selected from the group consisting of: OH, SH, $NH_2$,

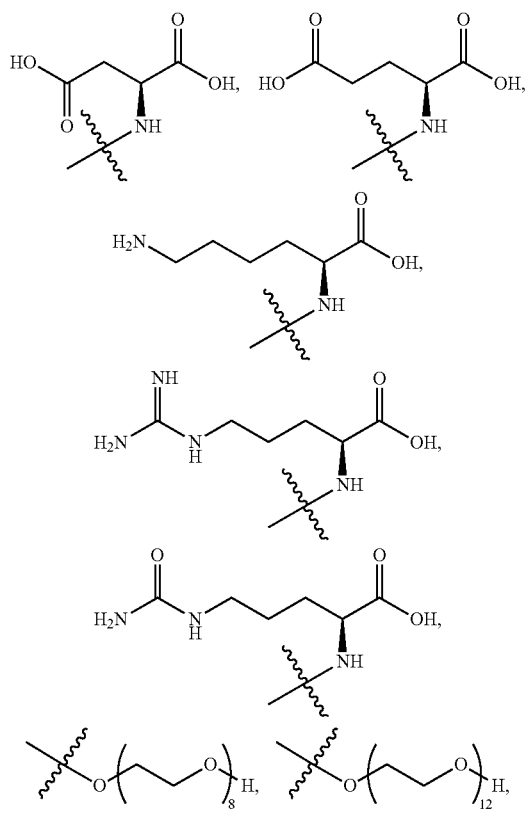

-continued

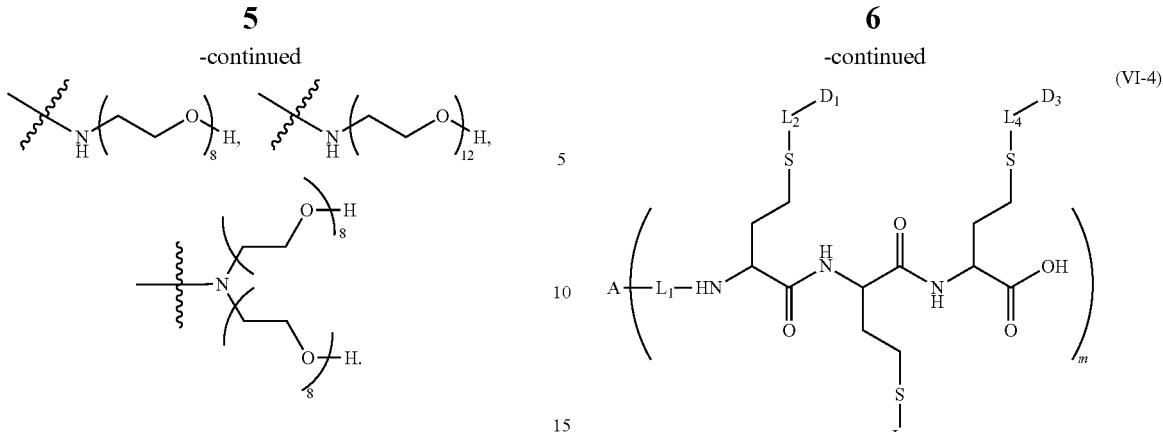

Further, the antibody-drug conjugate has the structure represented by formula (VI-1) to (VI-5):

(VI-1)

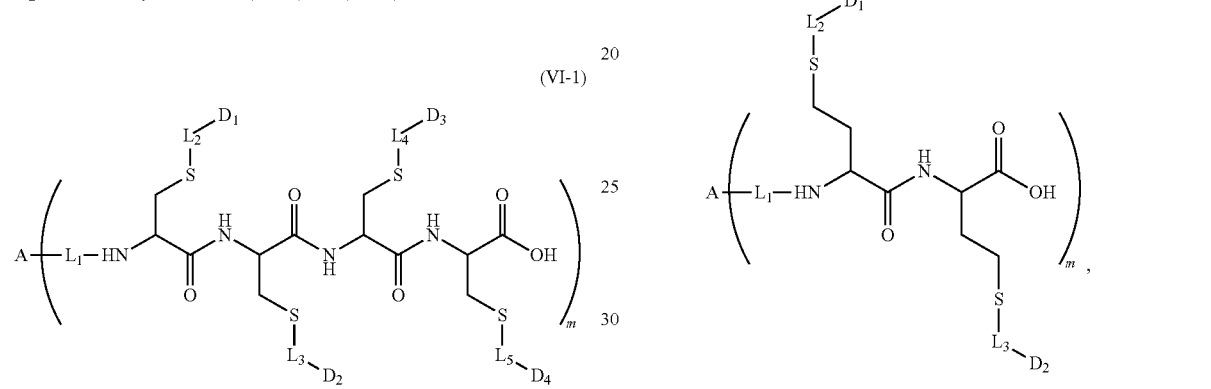

(VI-2)

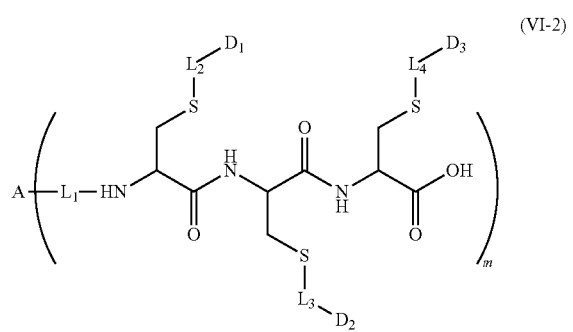

(VI-3)

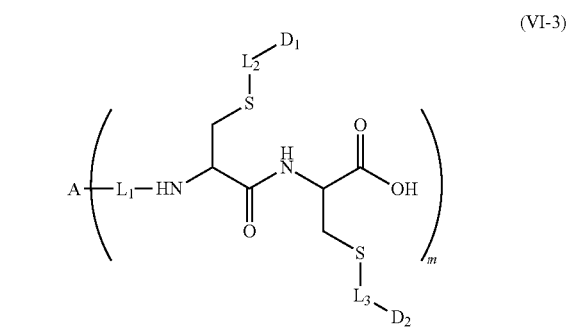

(VI-4)

(VI-5)

wherein,

A is an antibody or a functional binding fragment thereof;

$L_1$, $L_2$, $L_3$, $L_4$, and $L_5$ are each independently a linker, which may be the same or different;

$D_1$, $D_2$, $D_3$ and $D_4$ are each independently an active drug, which may be the same or different; and m is selected from 1, 2, 3, 4, 5, 6, 7 and 8.

Further, $L_1$ is covalently linked to an amino residue or a thiol residue of the antibody; preferably, $L_1$ is covalently linked to a thiol group of the antibody; more preferably, $L_1$ is covalently linked to a thiol residue formed by breaking an interchain disulfide bond of the antibody.

Further, $L_1$, $L_2$, $L_3$, $L_4$, . . . , and $L_{n+1}$ are a cleavable linker, a combination of cleavable linkers or a non-cleavable linker.

More further, the cleavable linker includes a peptide linker and a polysulfide bond, and wherein the peptide linker comprises 2-20 amino acids, preferably the peptide linker is selected from the group consisting of -valine-citrulline- (-Val-Cit-), -glycine-glycine-phenylalanine-glycine- (-Gly-Gly-Phe-Gly-), -valine-alanine-(-Val-Ala-), -valine-lysine- (-Val-Lys-), -valine-arginine- (-Val-Arg-), -phenylalanine-citrulline- (-Phe-Cit-), -phenylalanine-lysine- (-Phe-Lys-), -phenylalanine-arginine- (-Phe-Arg-) and a combination thereof; and the polysulfide bond contains 2-8 sulfur atoms, preferably the polysulfide bond is selected from the group consisting of a disulfide bond (—S—S—), a trisulfide bond (—S—S—S—) and a tetrasulfide bond (—S—S—S—S—).

In some specific examples, $L_1$ may be selected from the following structures:

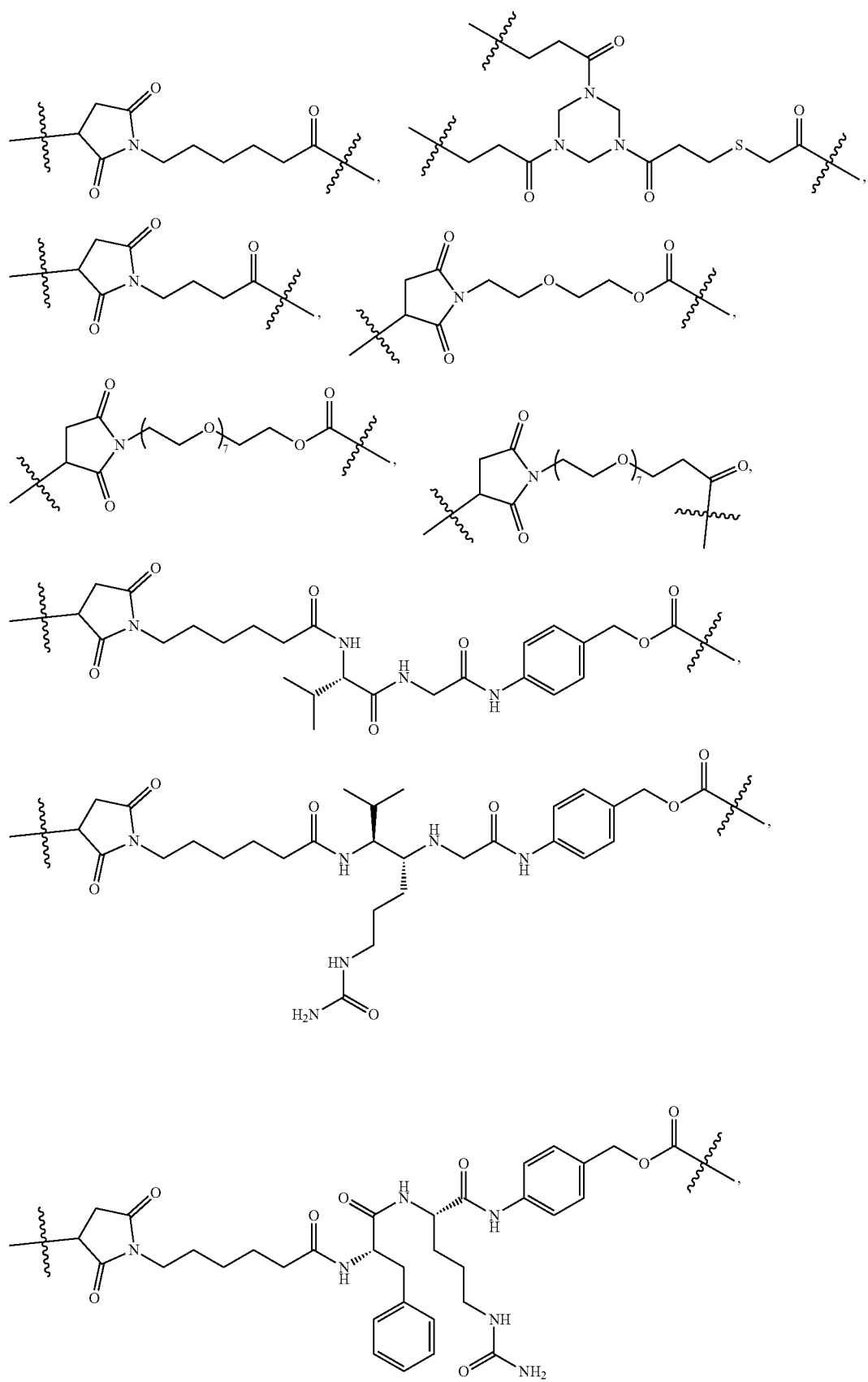

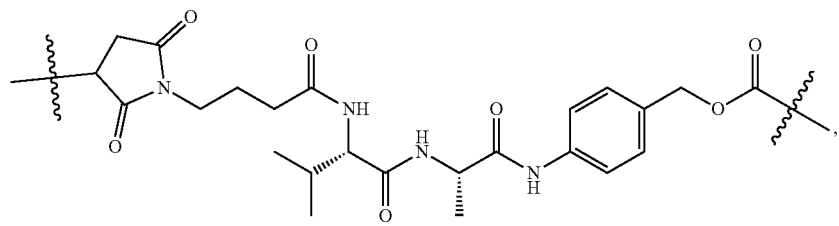
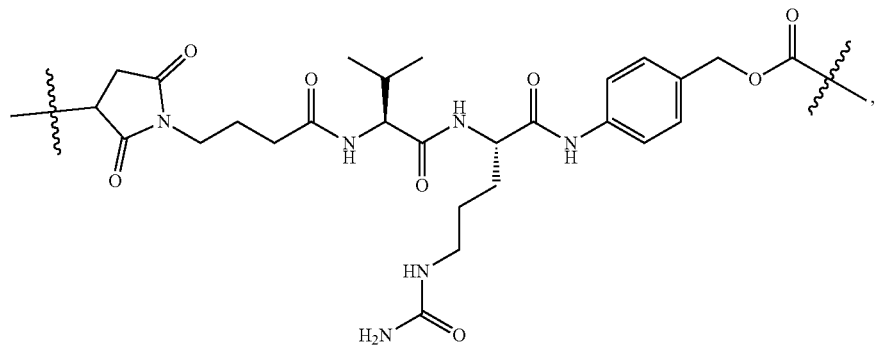
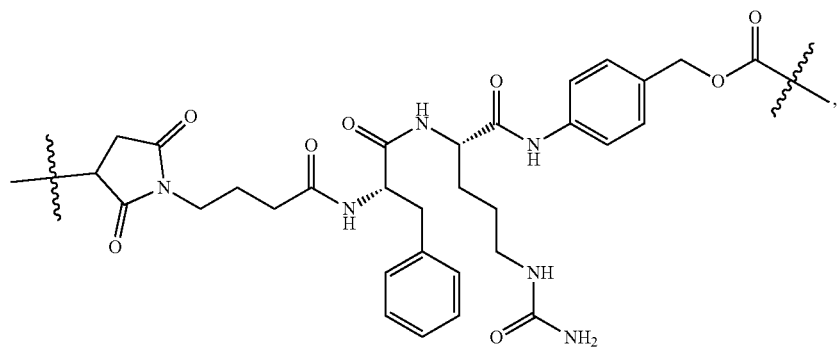
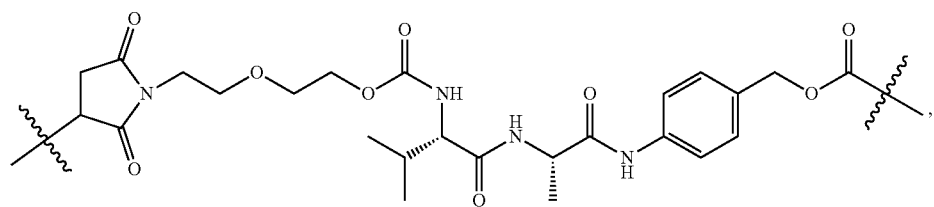
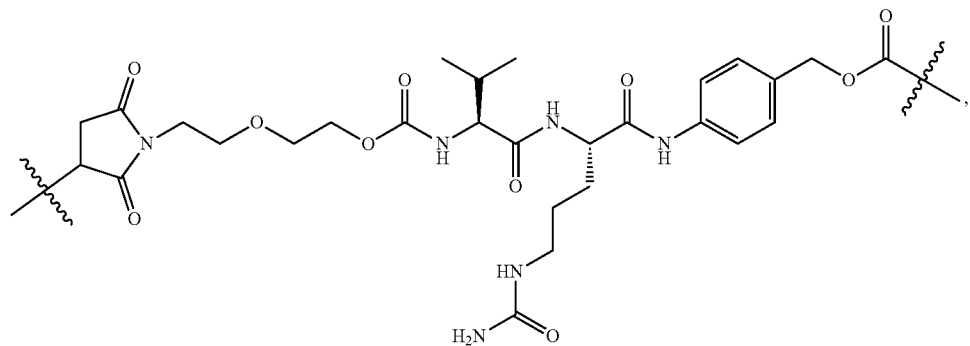

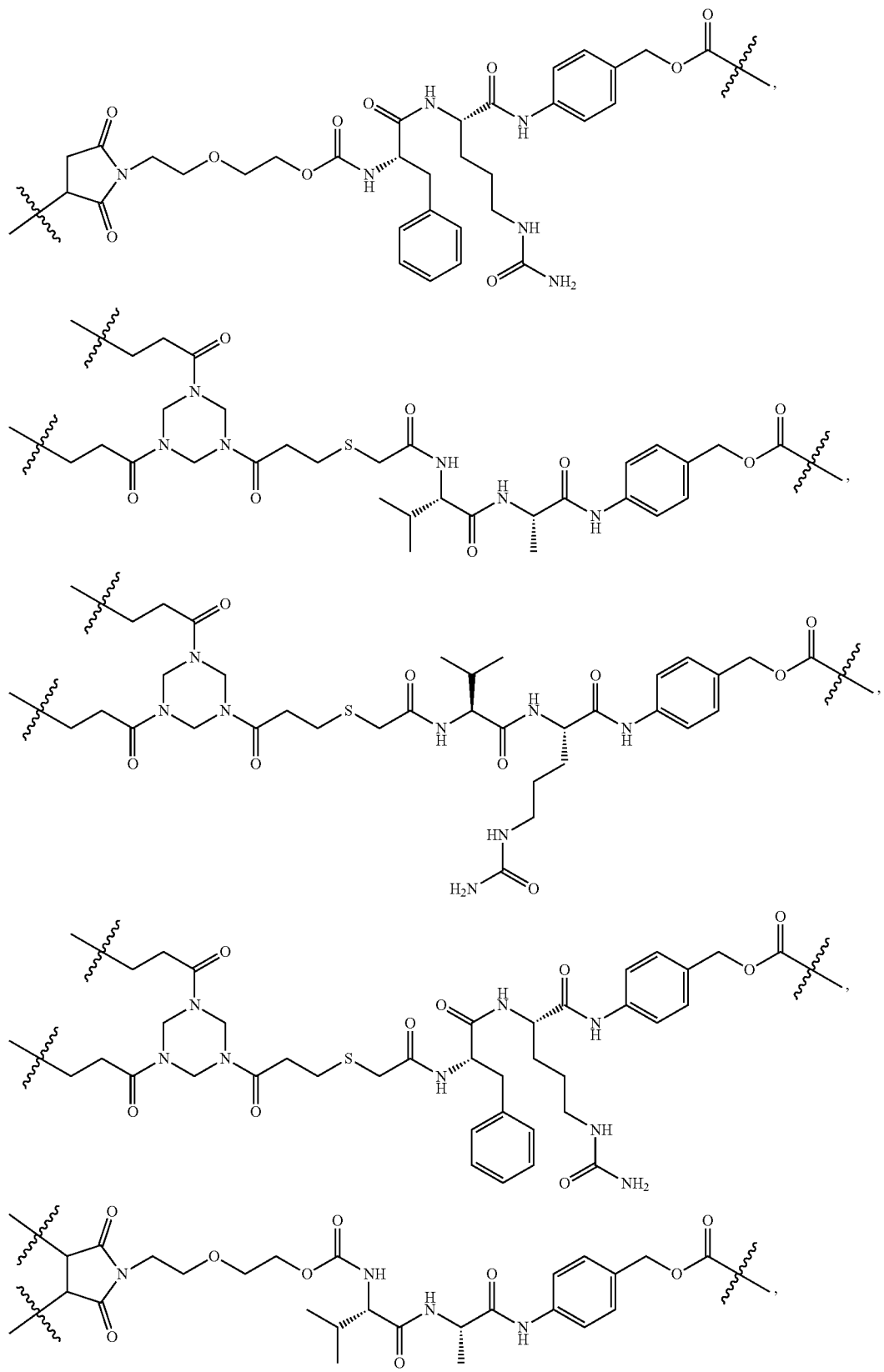 [SMILES: *C(=O)OCc1ccc(NC(=O)[C@H](CCCNC(N)=O)NC(=O)[C@H](Cc2ccccc2)NC(=O)OCCOCCN2C(=O)CC(*)C2=O)cc1 ; *CCC(=O)N1CN(C(=O)CC*)CN(C(=O)CCSCC(=O)N[C@H](C(=O)N[C@@H](C)C(=O)Nc2ccc(COC(*)=O)cc2)C(C)C)C1 ; *CCC(=O)N1CN(C(=O)CC*)CN(C(=O)CCSCC(=O)N[C@H](C(=O)N[C@@H](CCCNC(N)=O)C(=O)Nc2ccc(COC(*)=O)cc2)C(C)C)C1 ; *CCC(=O)N1CN(C(=O)CC*)CN(C(=O)CCSCC(=O)N[C@@H](Cc2ccccc2)C(=O)N[C@@H](CCCNC(N)=O)C(=O)Nc2ccc(COC(*)=O)cc2)C1 ; *C(=O)OCc1ccc(NC(=O)[C@H](C)NC(=O)[C@@H](NC(=O)OCCOCCN2C(=O)C(*)C(*)C2=O)C(C)C)cc1]

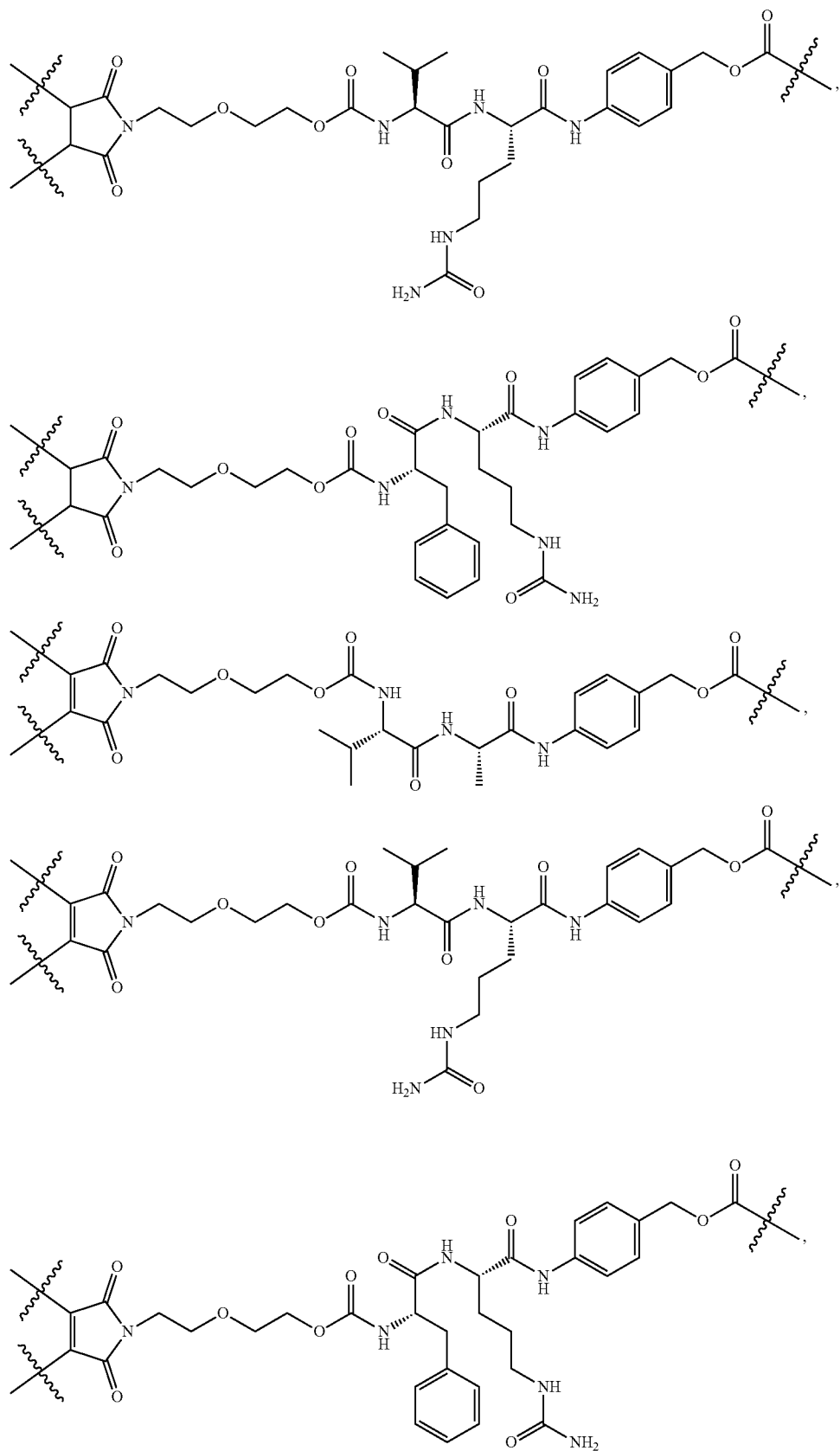

-continued
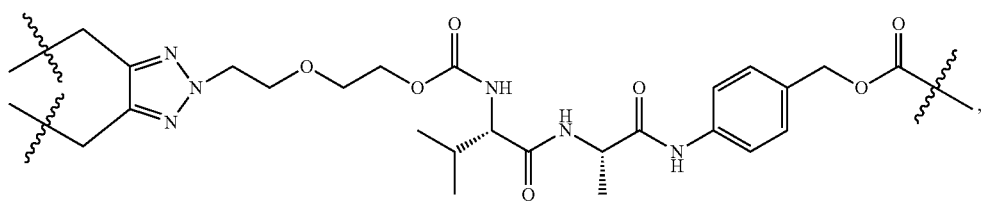
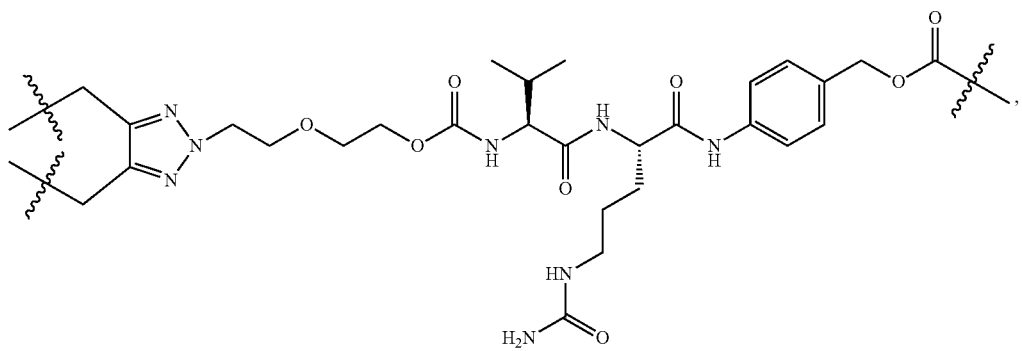
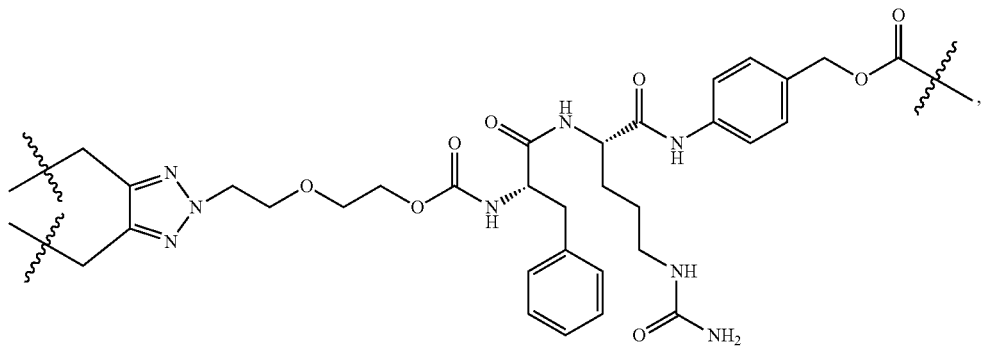
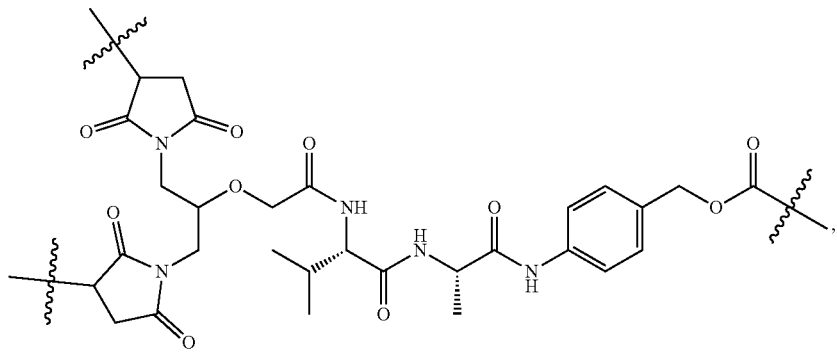
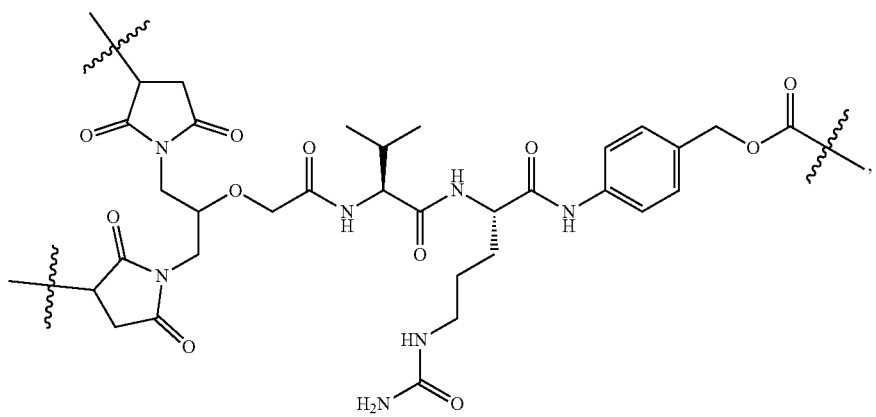

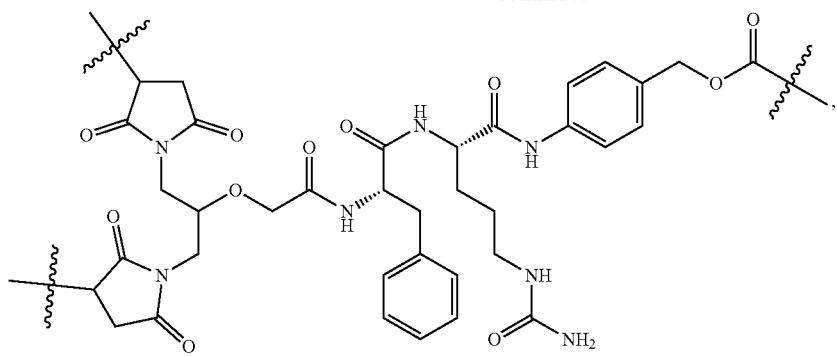
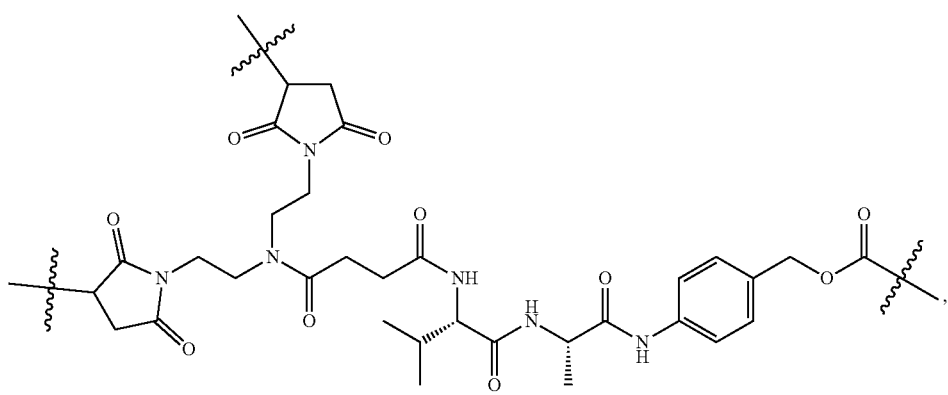
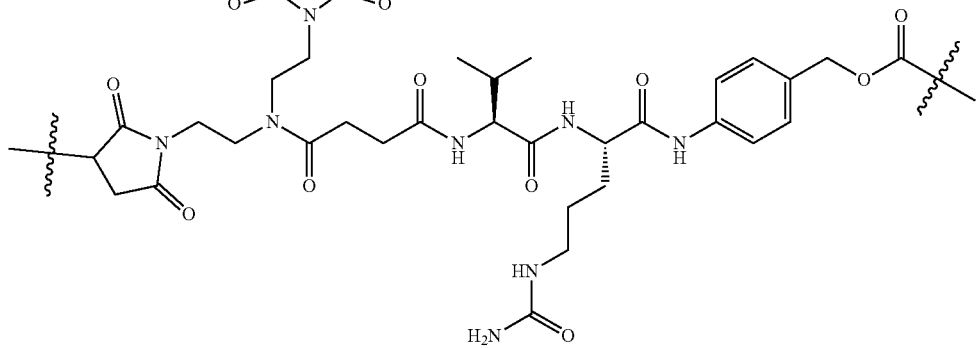
and
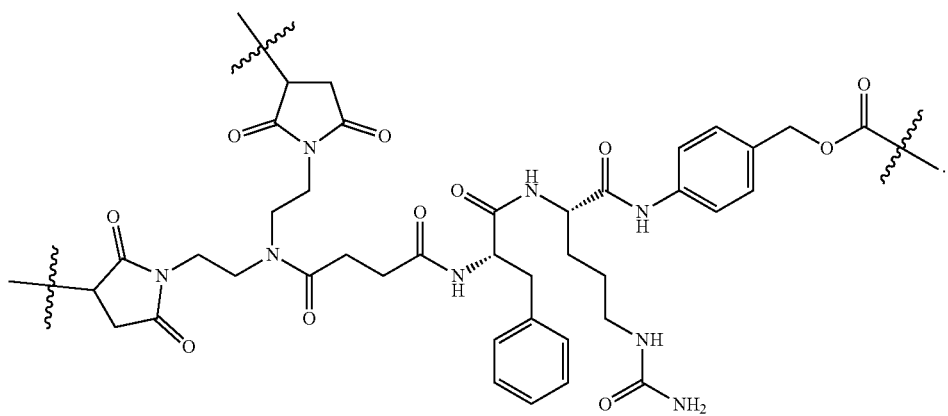

In some specific examples, $L_2, L_3, L_{49} \ldots, L_{n+1}$ may be selected from the following structures:
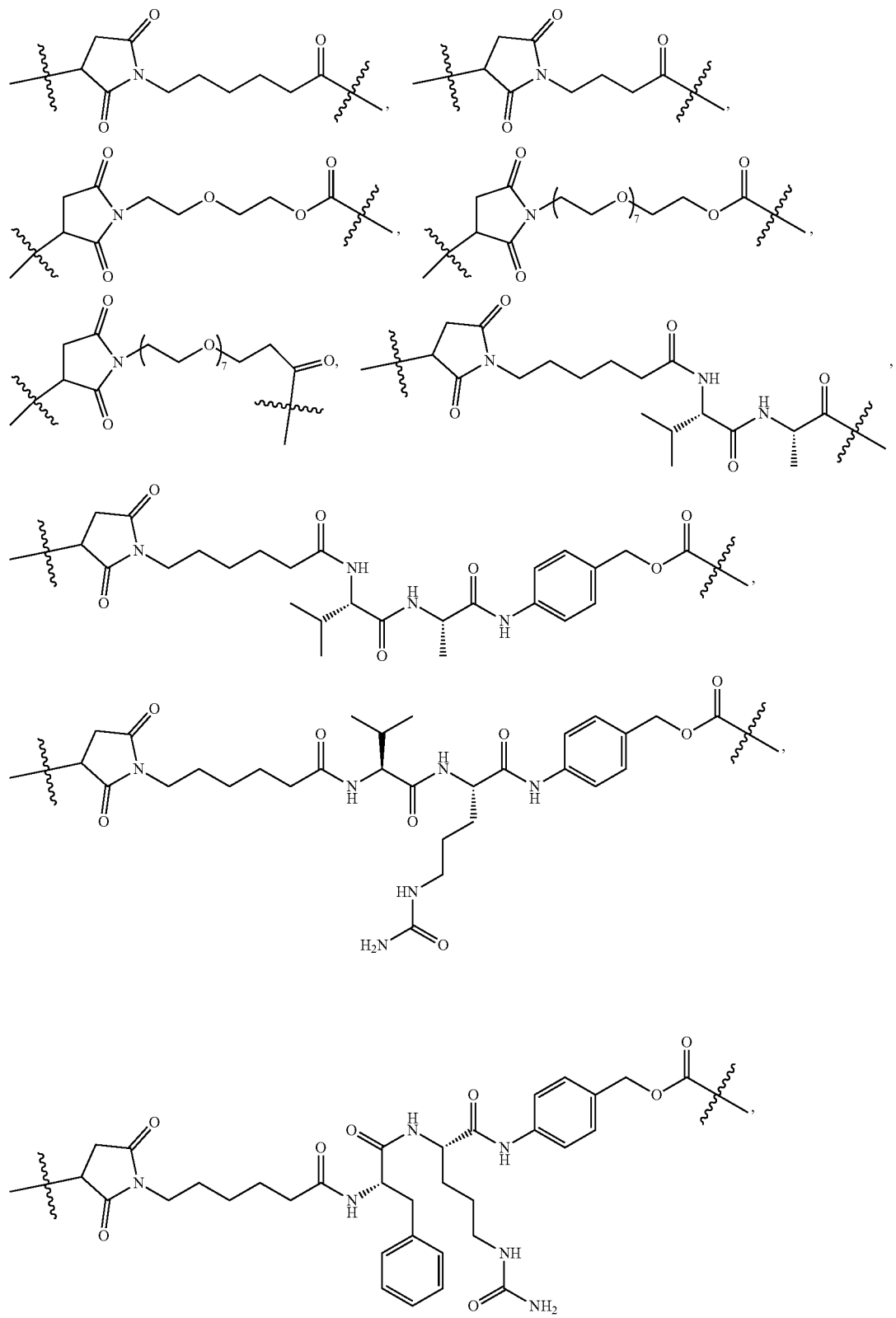

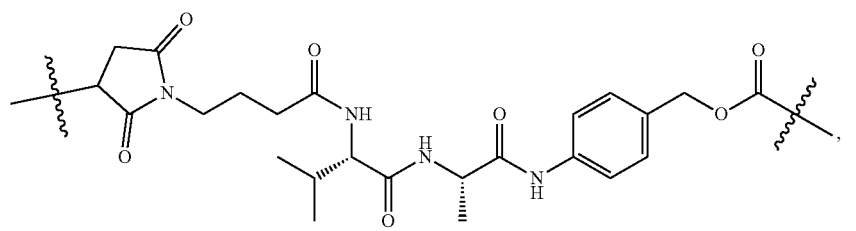
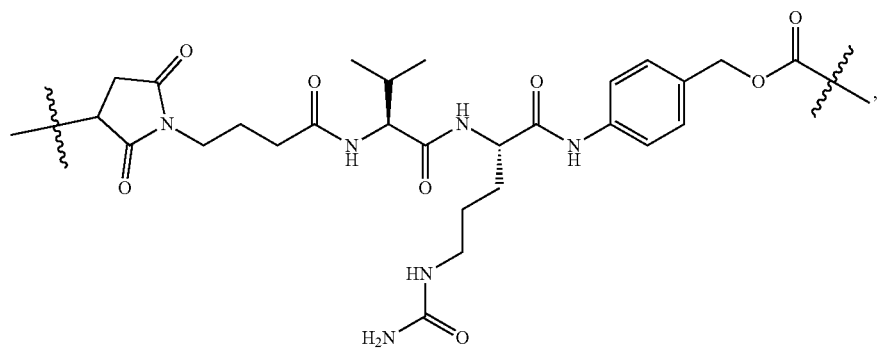
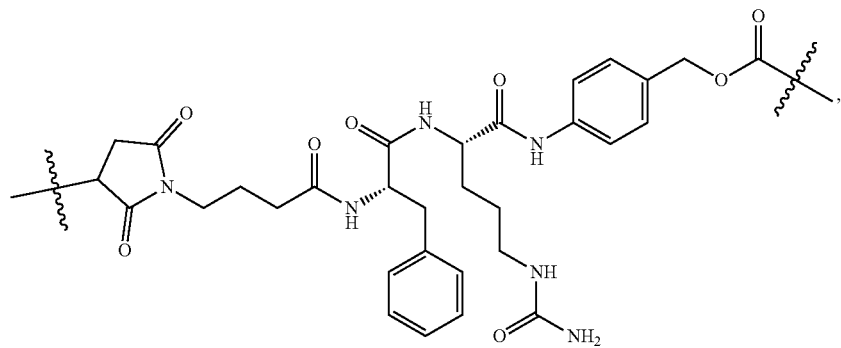
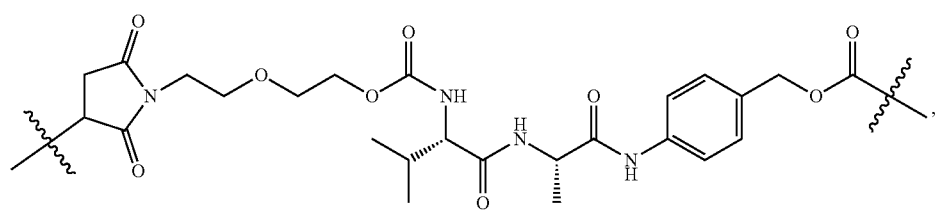
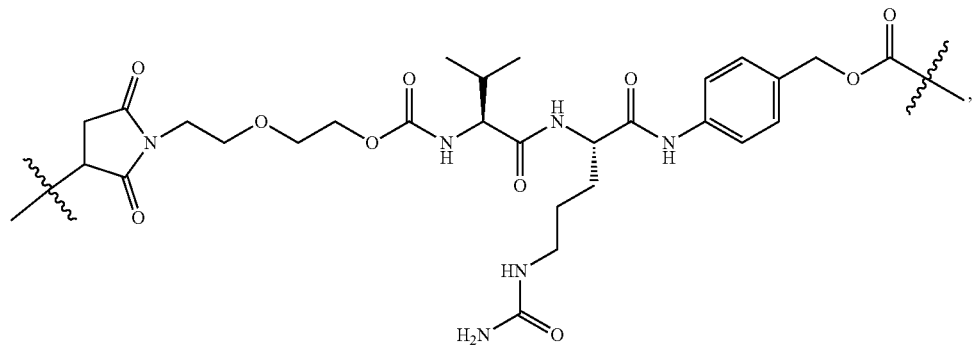

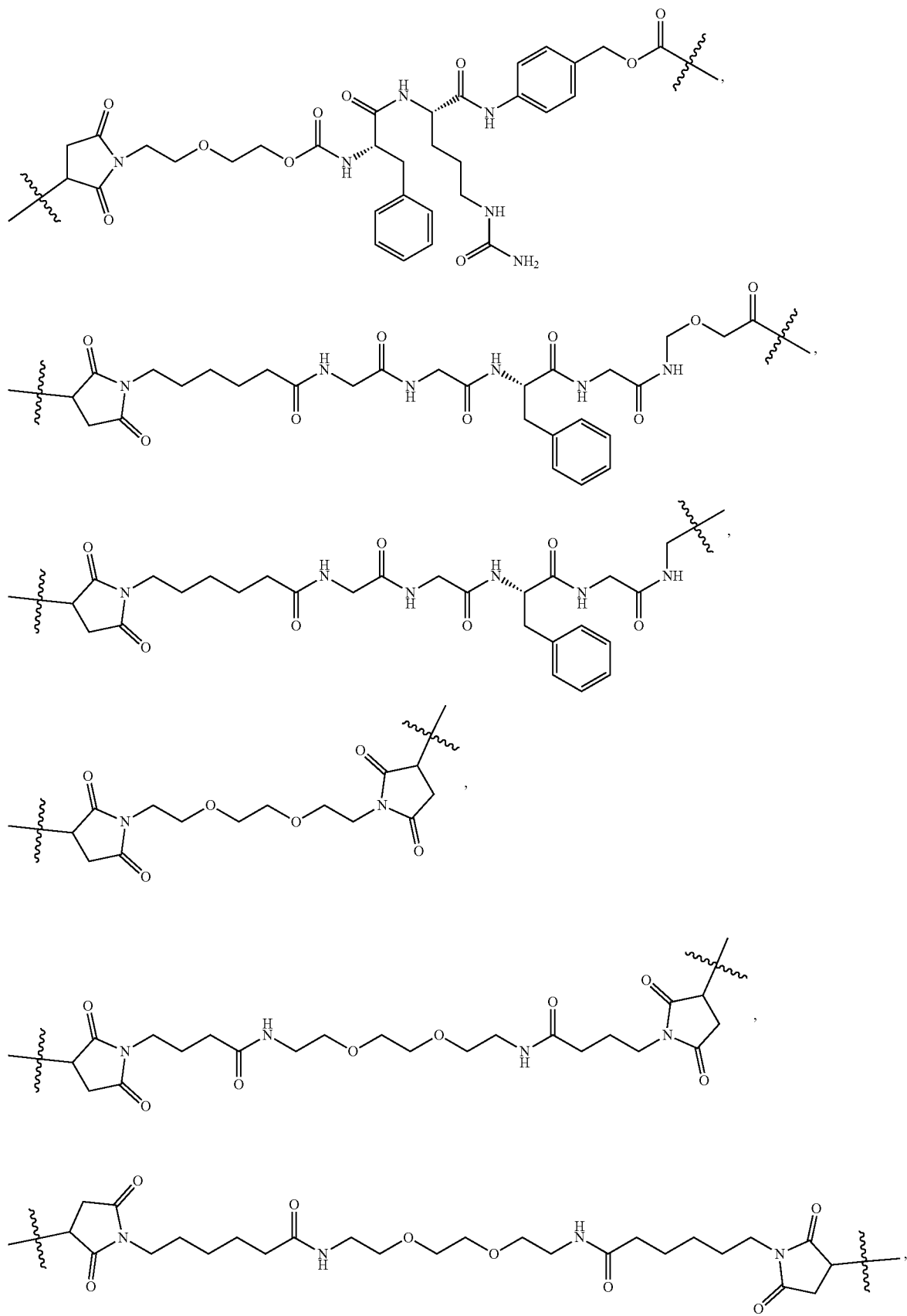

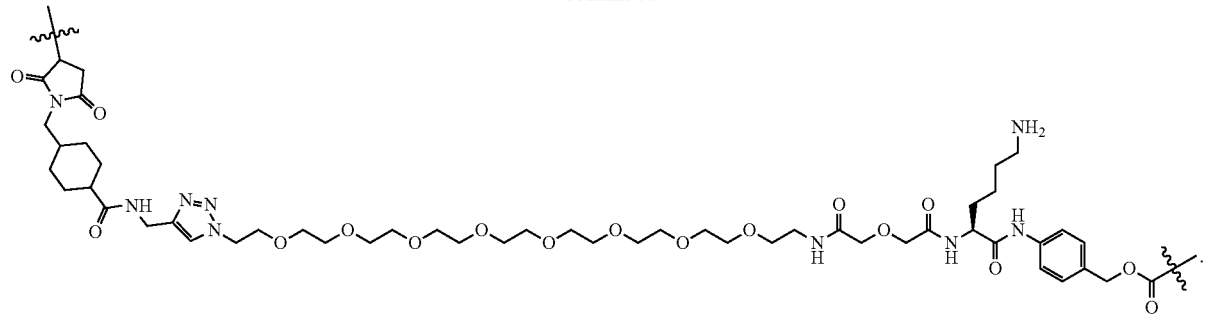 [SMILES: *C(=O)OCc1ccc(NC(=O)[C@H](CCCCN)NC(=O)COCC(=O)NCCOCCOCCOCCOCCOCCOCCOCCOCCn2cc(CNC(=O)C3CCC(CN4C(=O)CC(*)C4=O)CC3)nn2)cc1]

Further, the antibody or functional binding fragment thereof includes a monoclonal antibody, a polyclonal antibody, an antibody fragment, Fab, Fab', Fab'-SH, F(ab')$_2$, Fv, single chain Fv ("scFv"), a diabody, a linear antibody, a bispecific antibody, a multispecific antibody, a chimeric antibody, a humanized antibody, a fully human antibody, or a fusion protein containing an antigen-binding fragment of antibody; preferably, the antibody is a humanized monoclonal antibody or a fully human antibody.

Furthermore, the antibody is an IgG antibody or a functional binding fragment thereof, preferably, the antibody is an IgG$_1$, IgG$_2$, IgG$_3$, or IgG$_4$ antibody.

Further, the active drug is a cytotoxic molecule, a cell differentiation factor, a stem cell trophic factor, a steroids drug, a drug for treating an autoimmune disease, an anti-inflammatory drug or a drug for treating an infectious disease.

More further, the cytotoxic molecule includes, but is not limited to, a tubulin inhibitor or a DNA damaging agent; preferably, the tubulin inhibitor includes a cytotoxic molecule of dolastatins and auristatins, a cytotoxic molecule of maytansines; the DNA damaging agent includes calicheamicins, duocarmycins, pyrrolobenzodiazepine (PBD) a derivative of anthramycin, camptothecins and derivatives thereof, and SN-38; further preferably, the cytokine molecule of auristatins includes MMAE, MMAF, and a derivative thereof; and the cytotoxic molecule of maytansines includes DM1, DM4, and a derivative thereof; and further preferably, the cytotoxic molecule includes the following molecules:

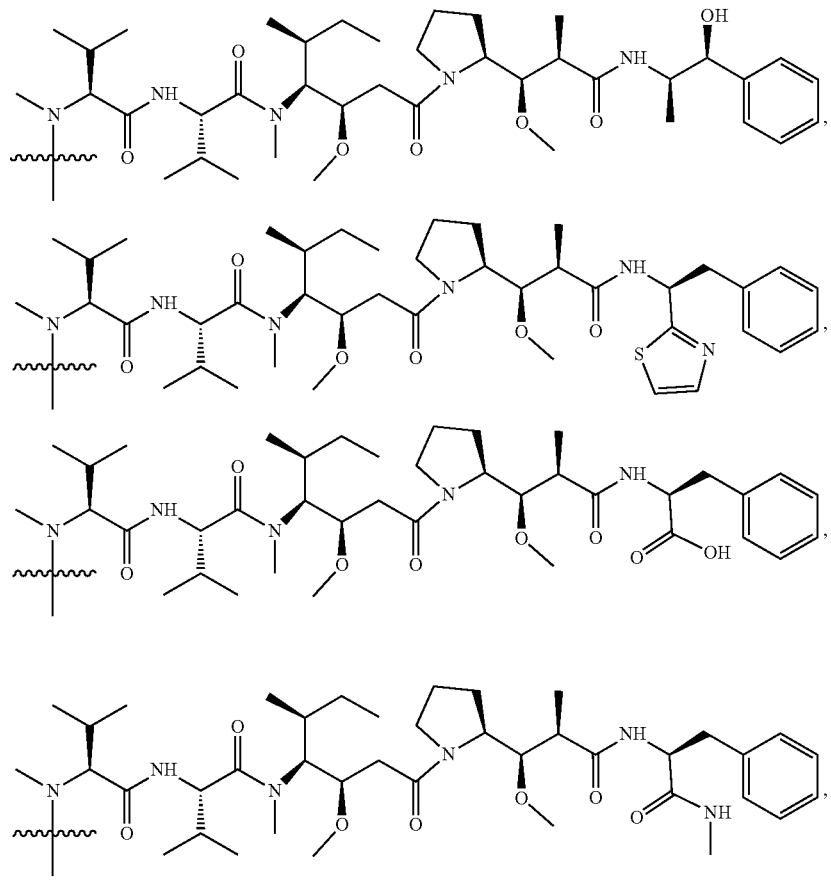

-continued
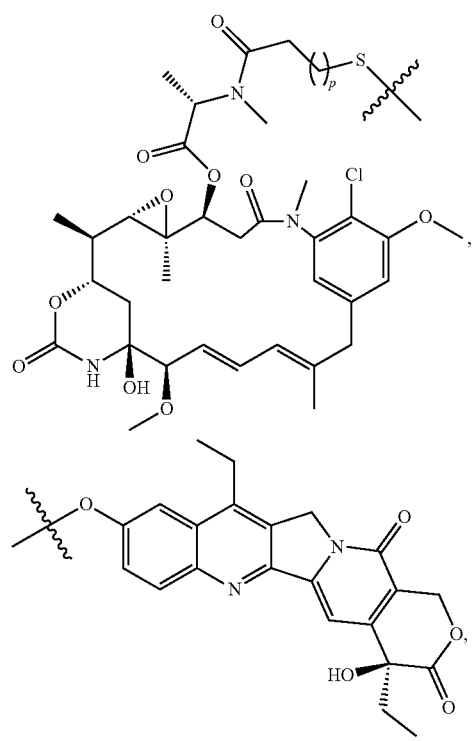
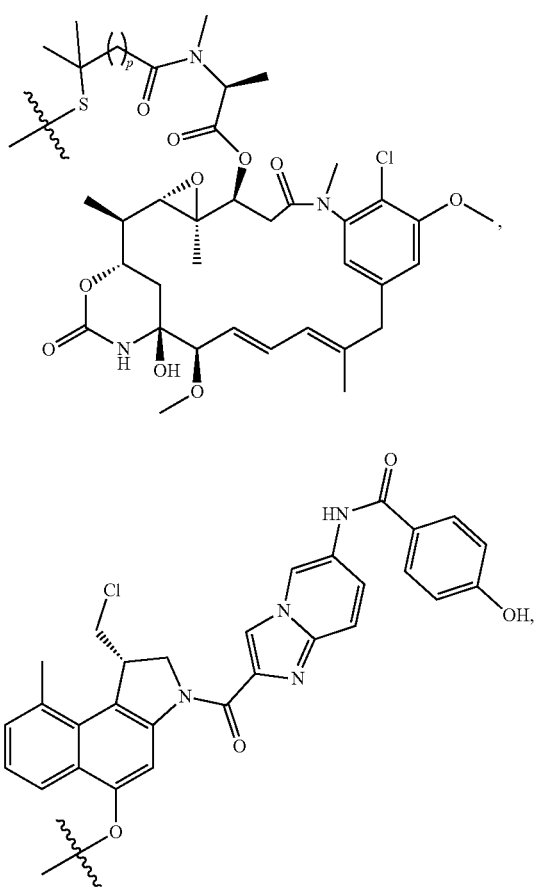
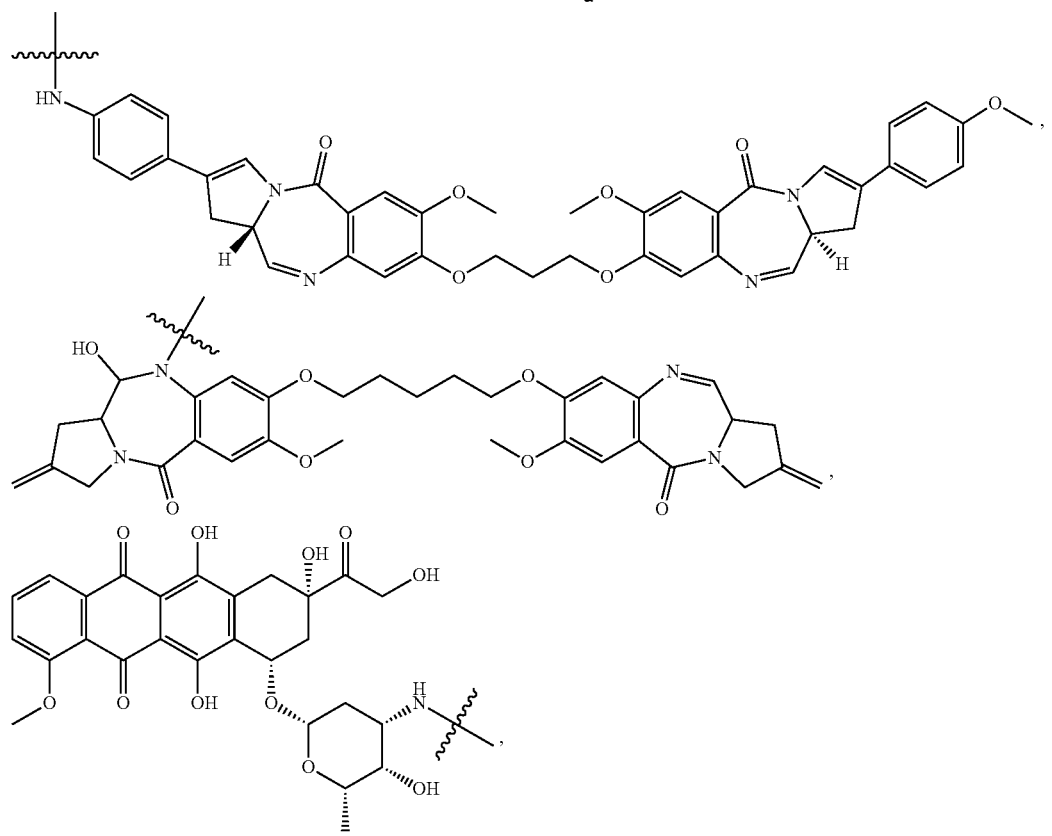

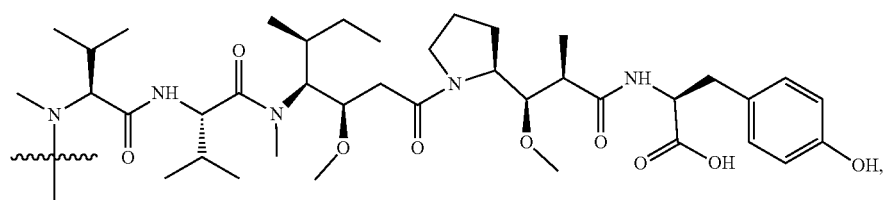
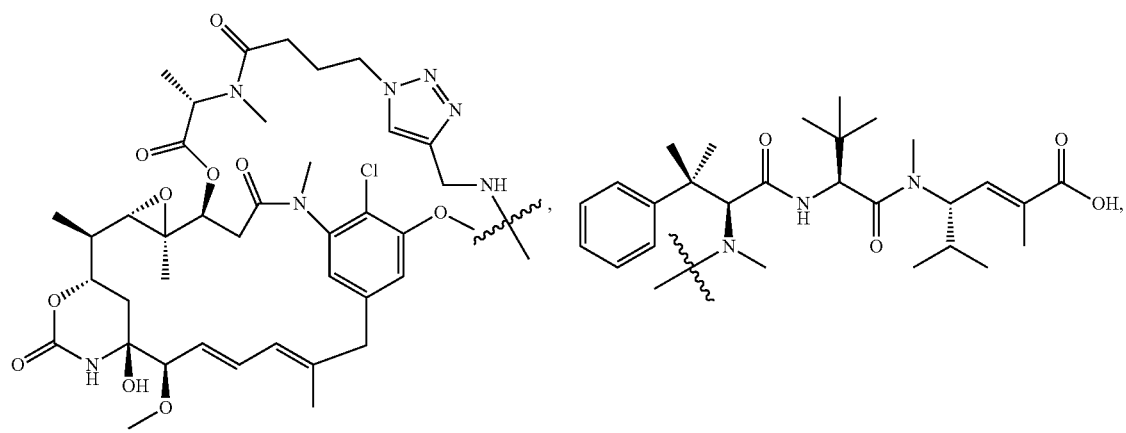
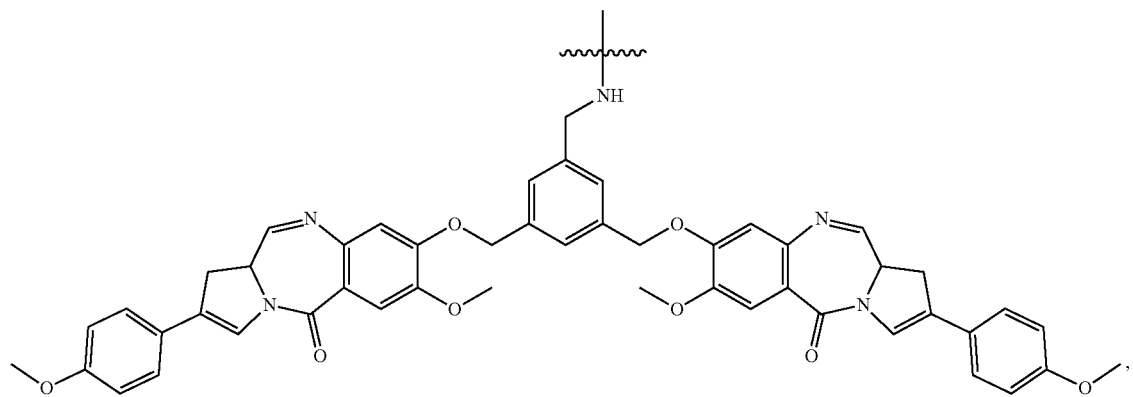
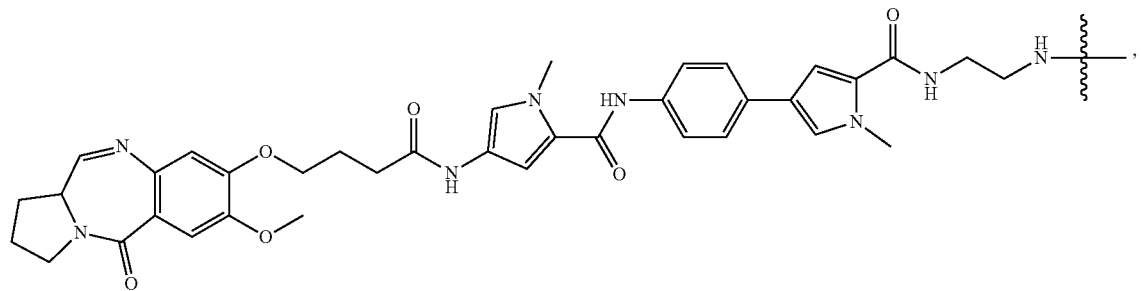

-continued
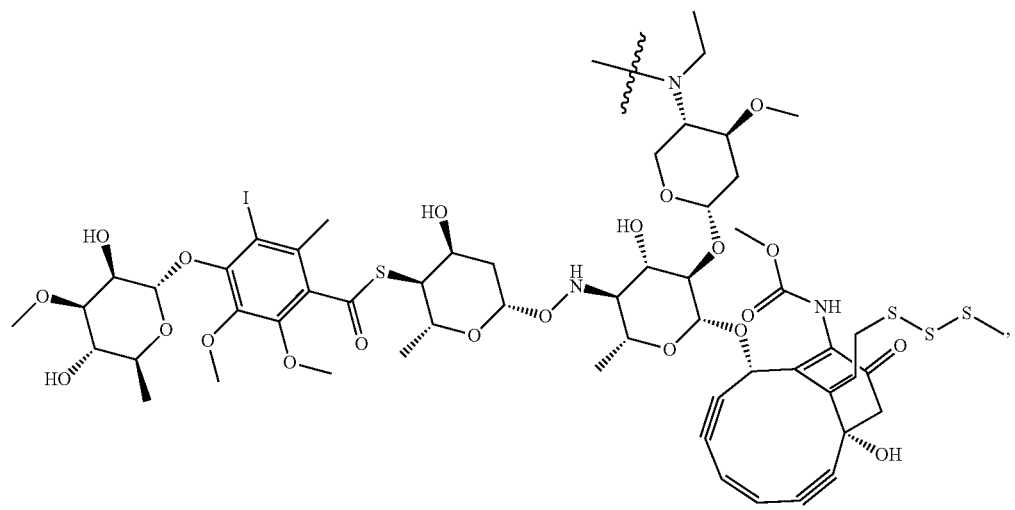
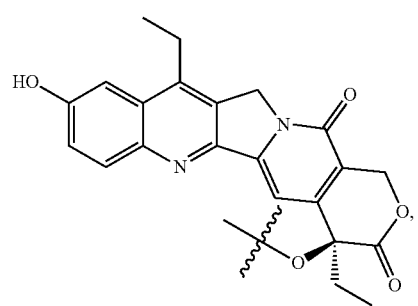
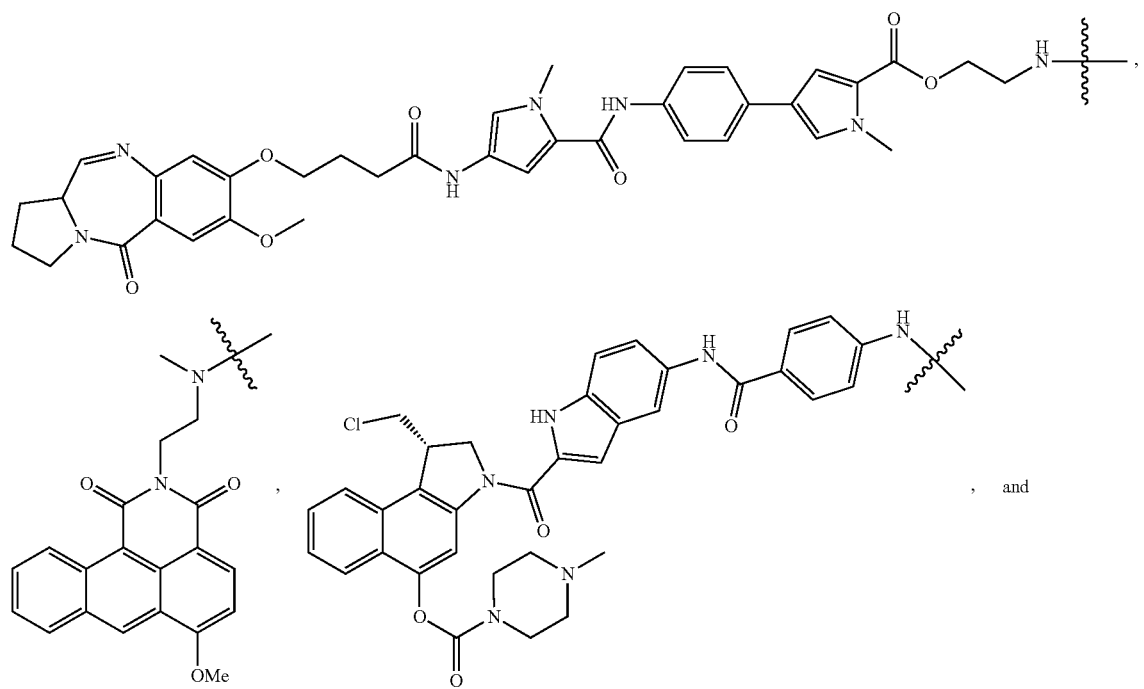
, and

-continued
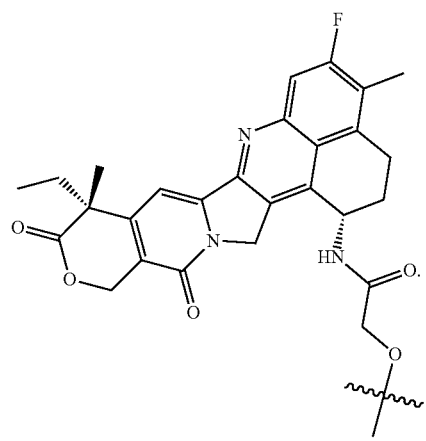 [SMILES: *OCC(=O)N[C@H]1CCc2c(C)c(F)cc3nc4c(c1c23)Cn1c-4cc2c(c1=O)COC(=O)[C@]2(C)CC]
Further, the structures of the antibody-drug conjugate are represented as follows:

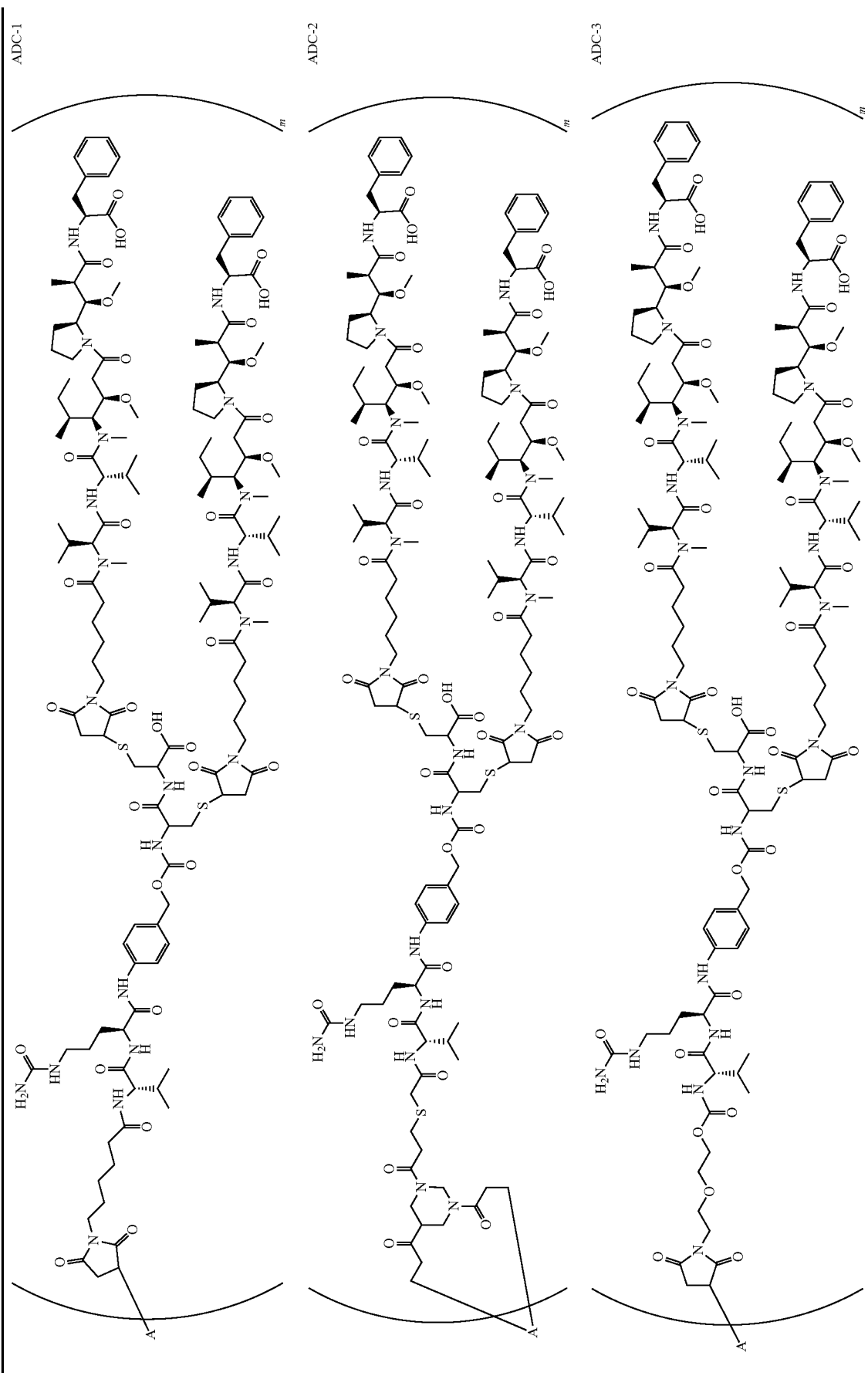

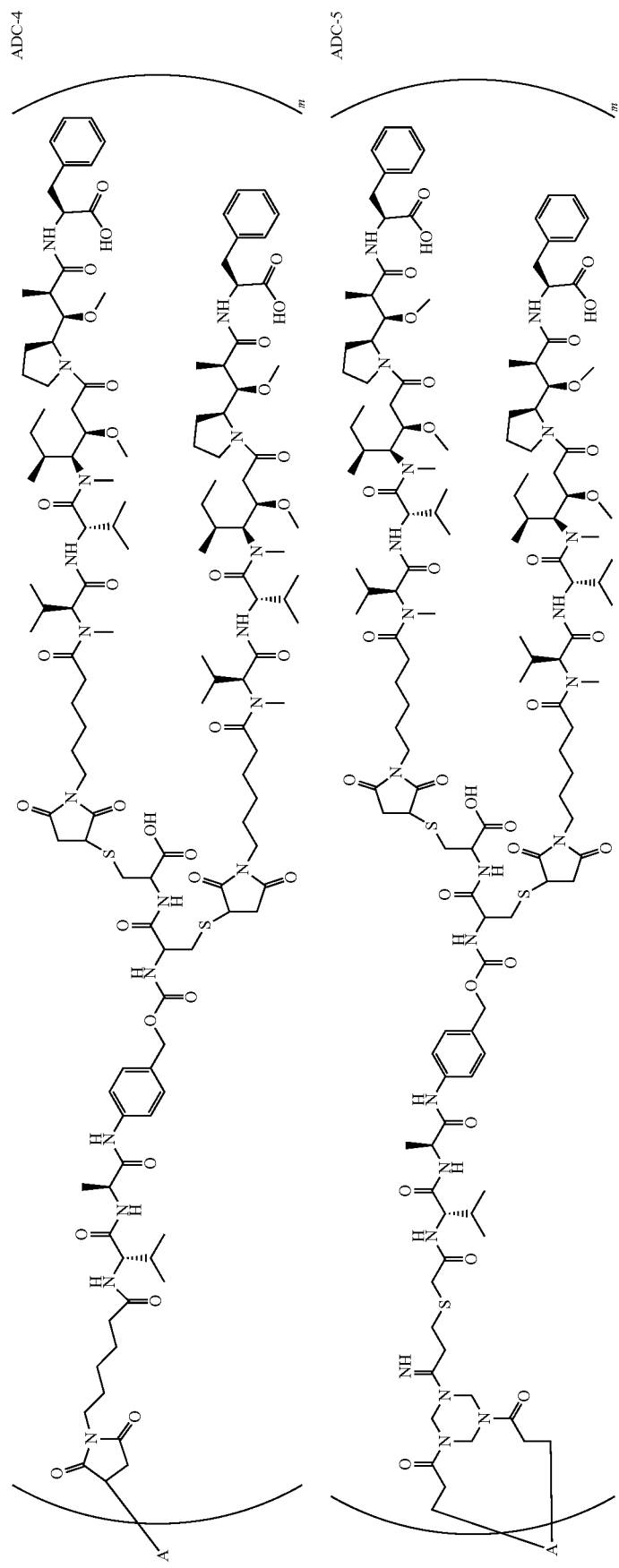

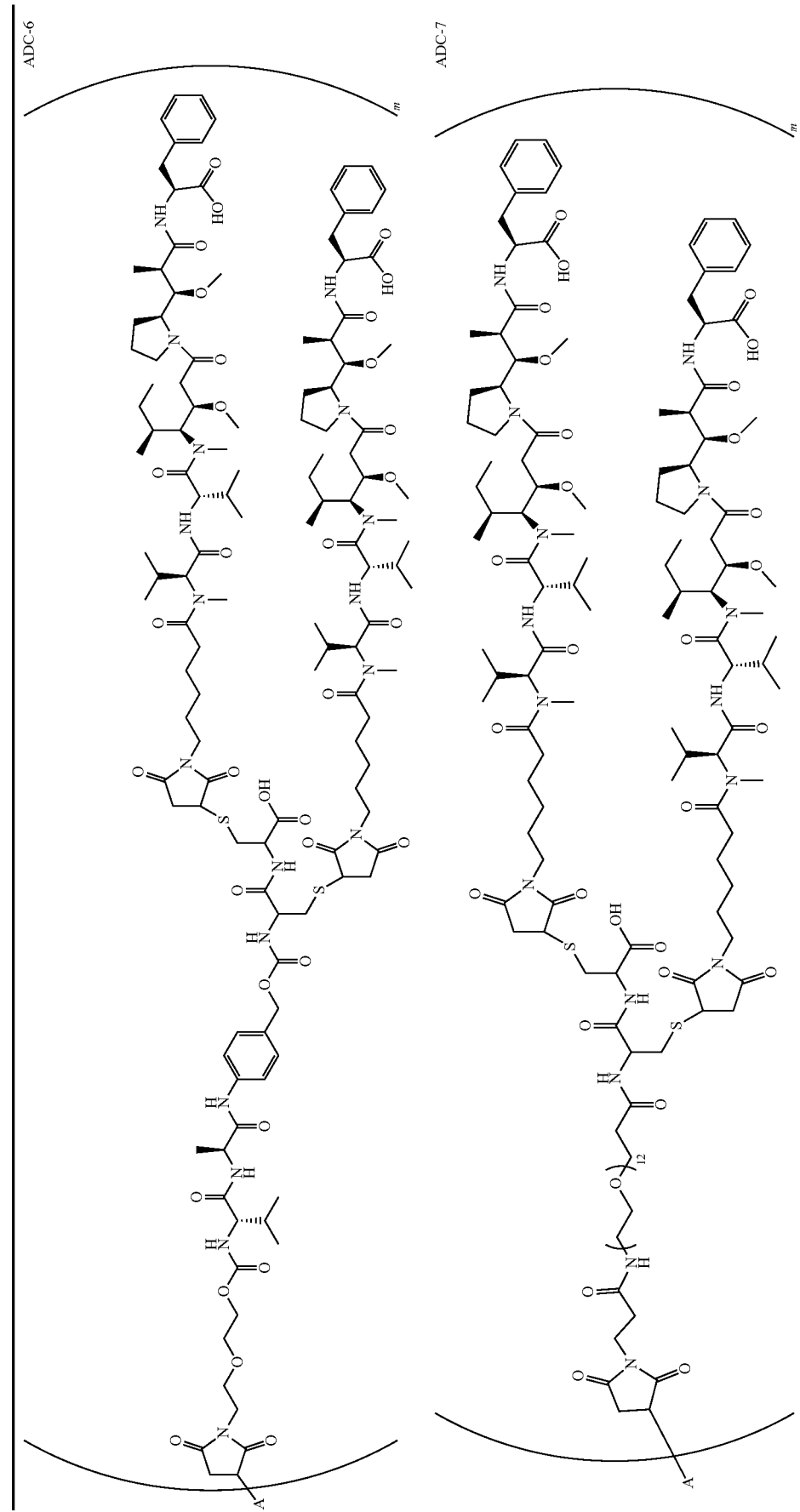

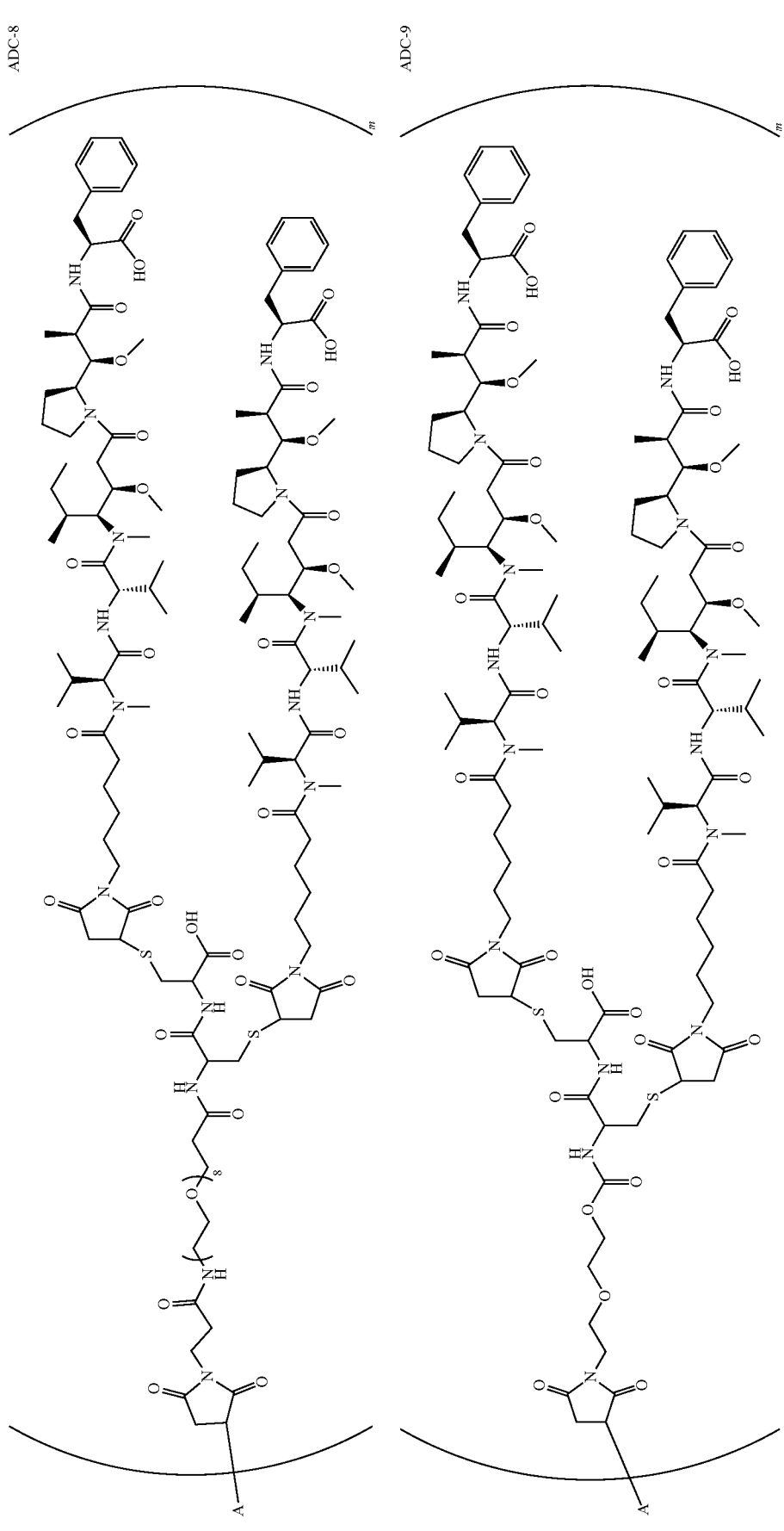

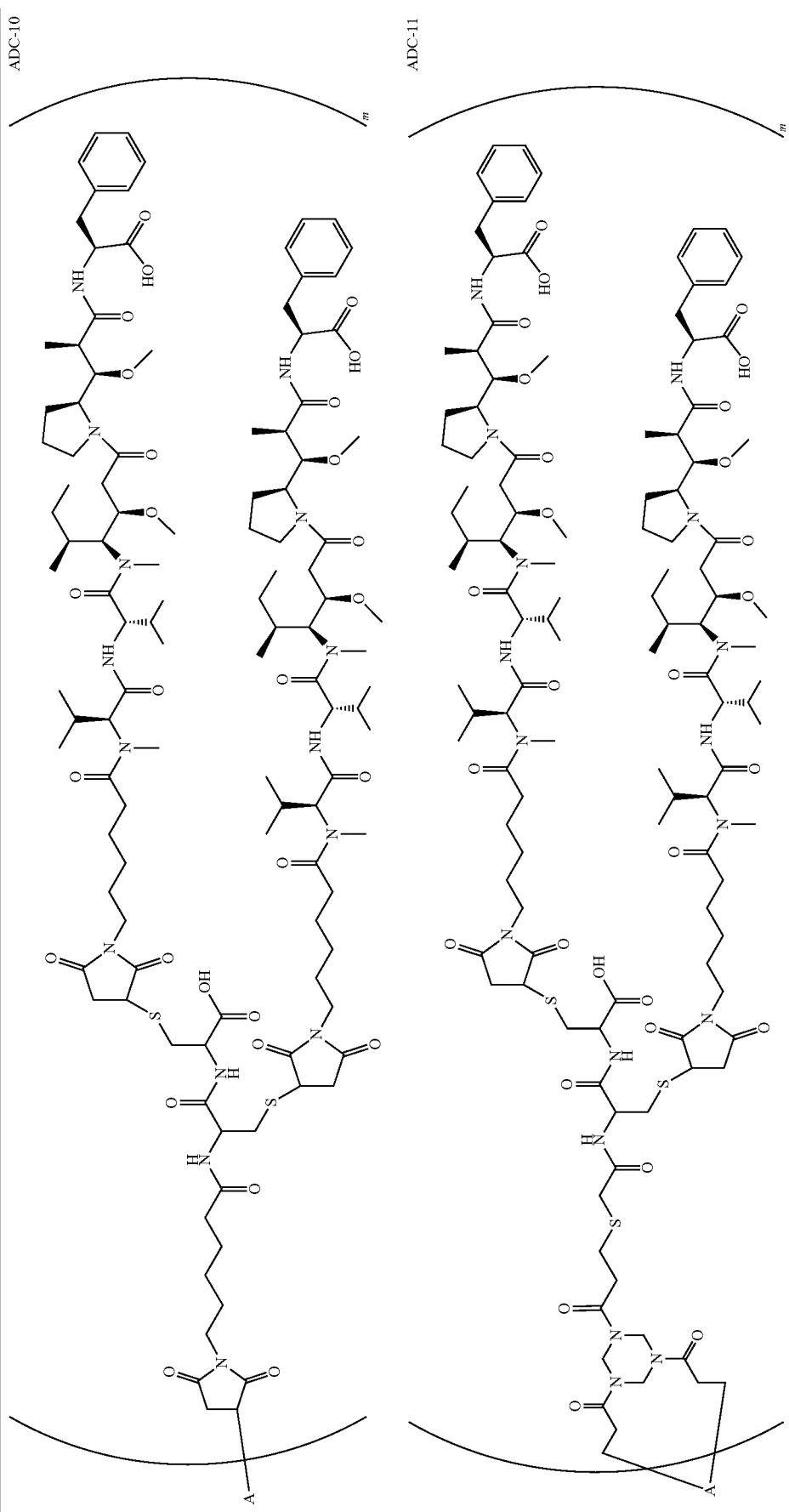

-continued
ADC-12
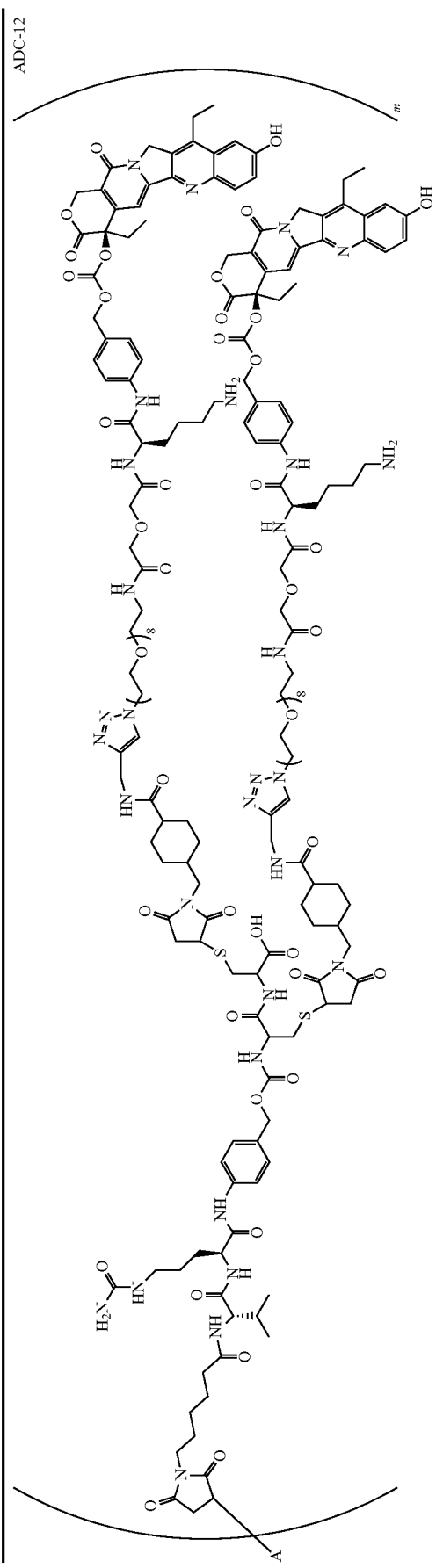
ADC-13
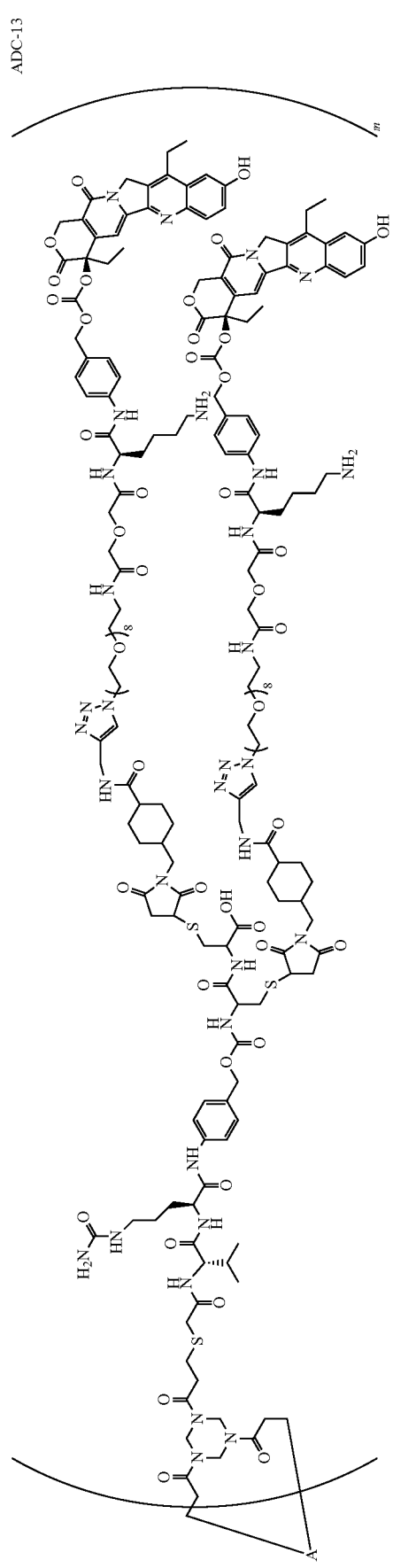

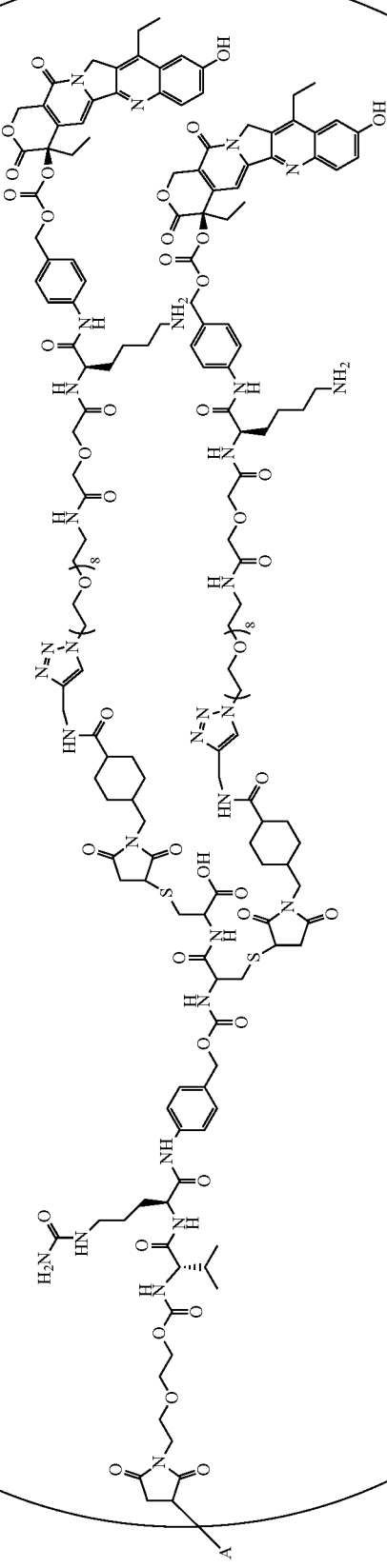
ADC-14
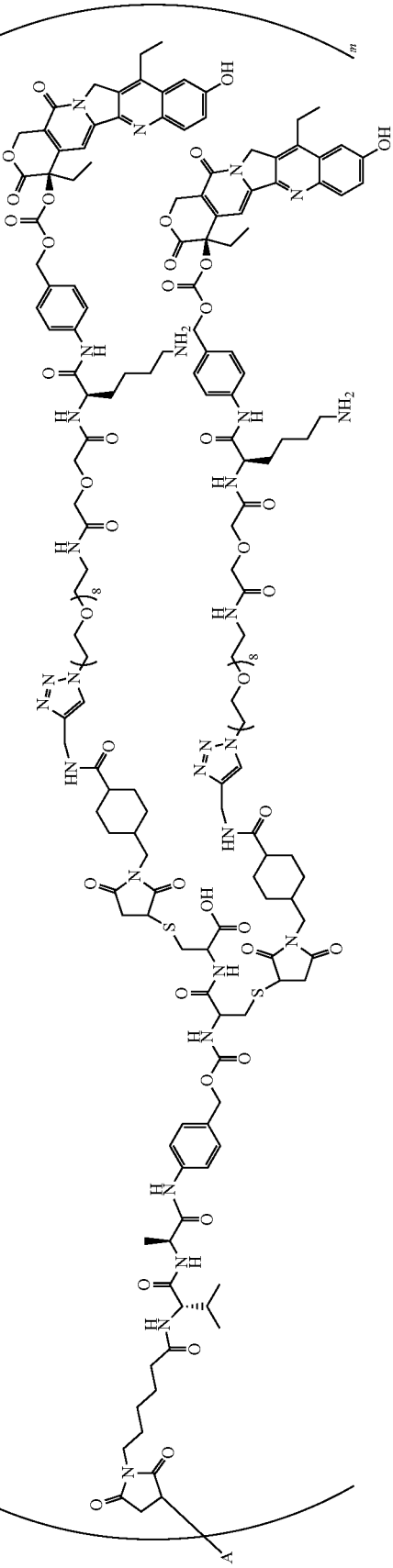
ADC-15

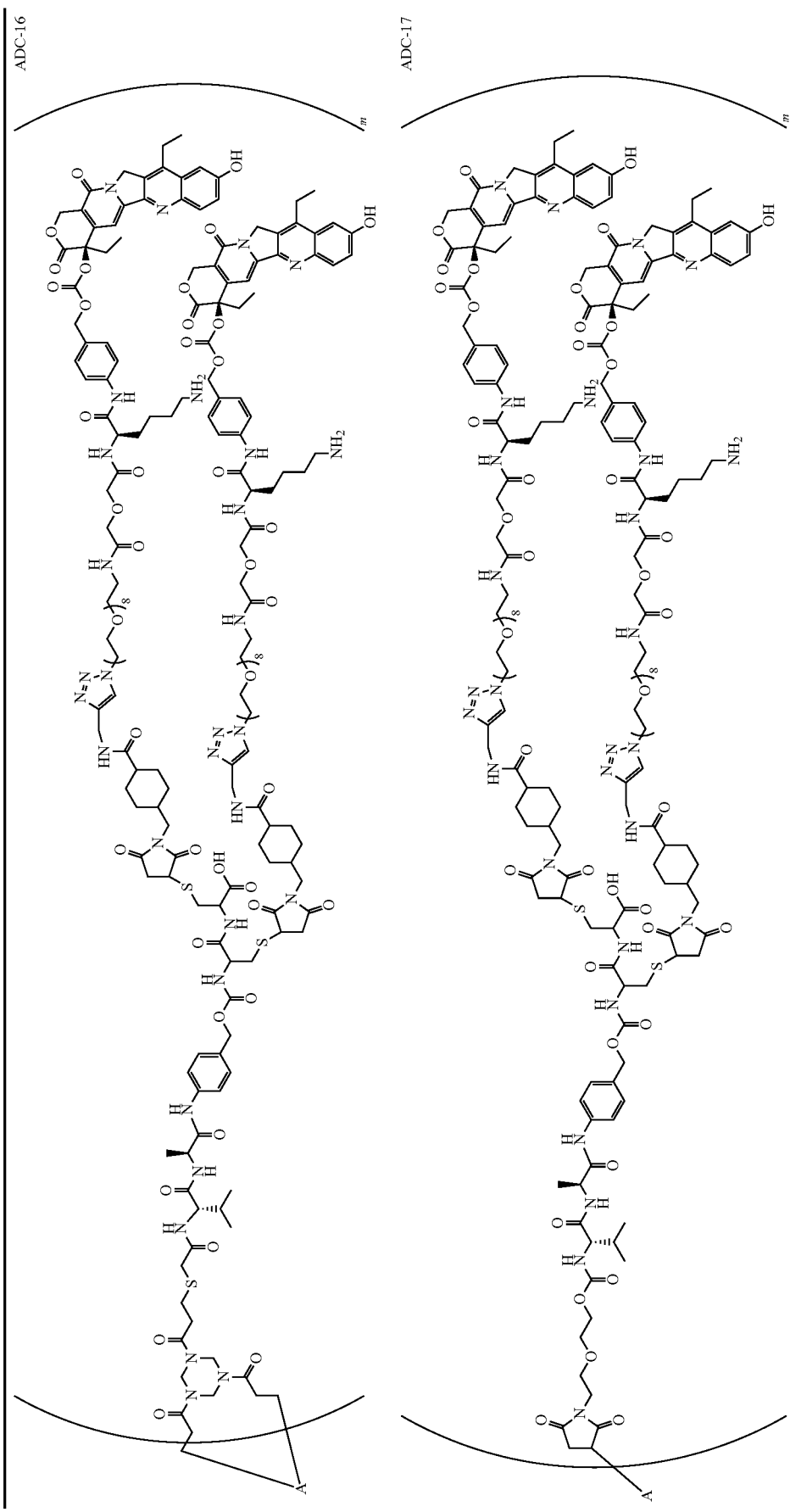

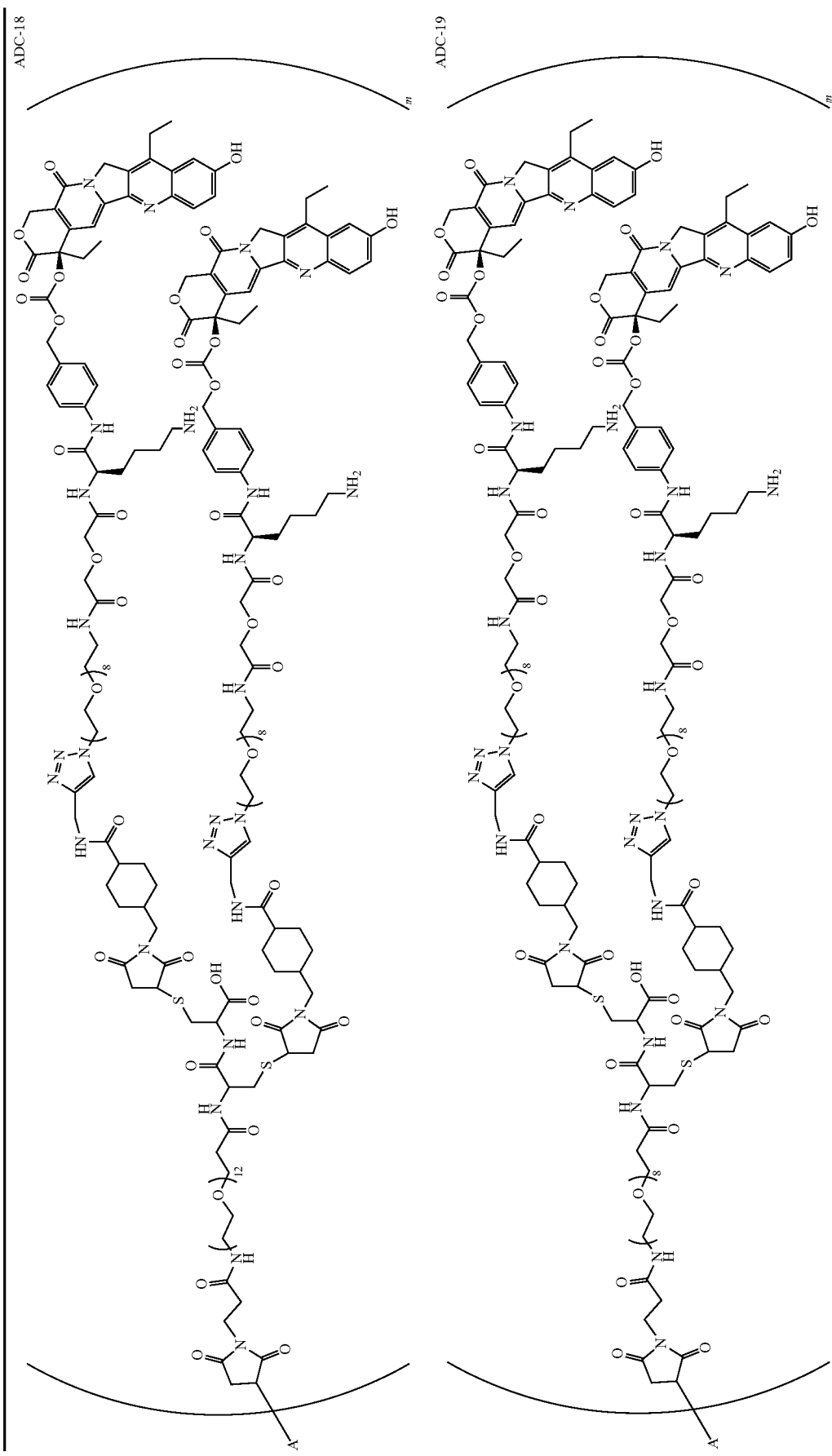

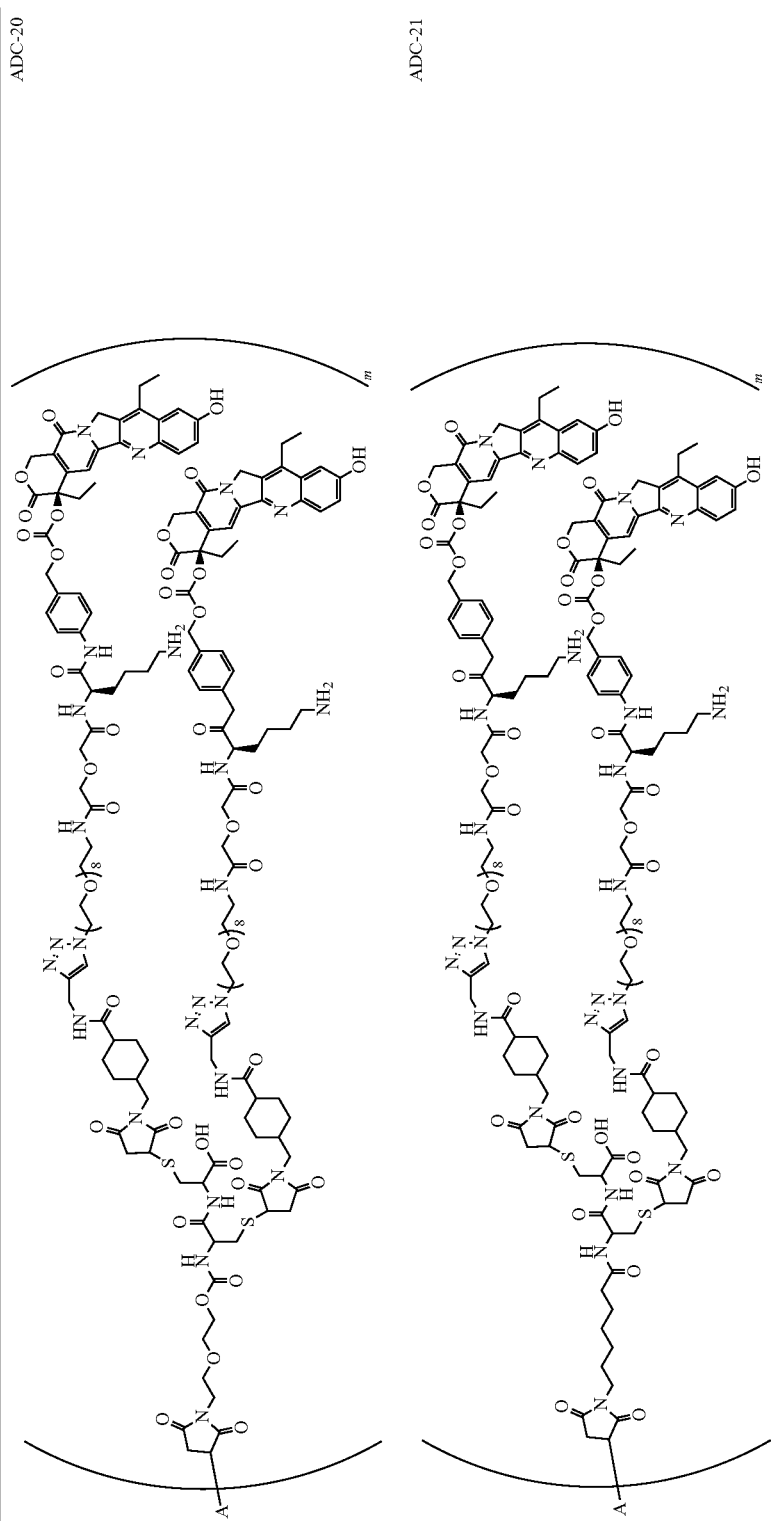

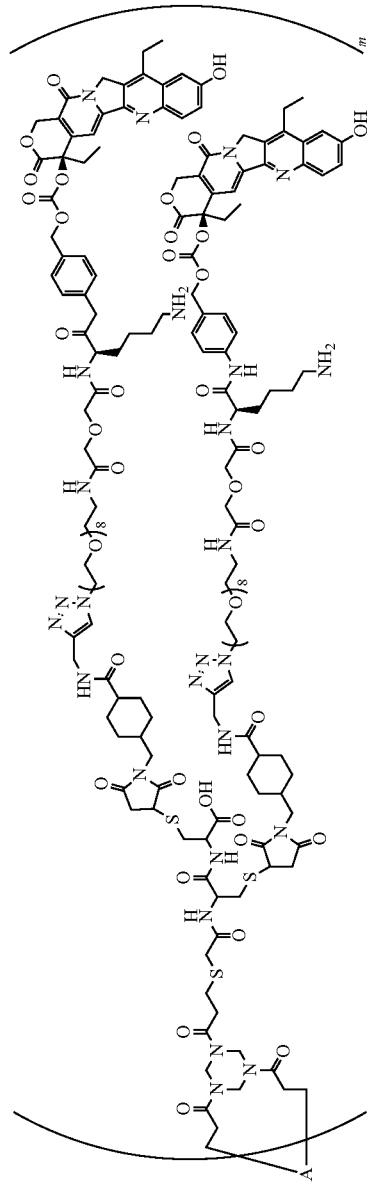
ADC-22
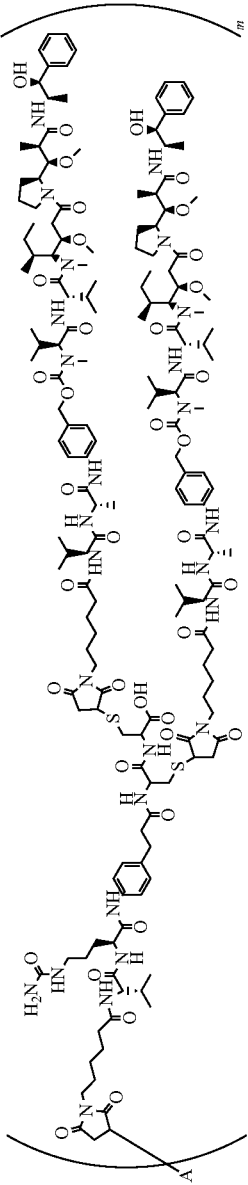
ADC-23
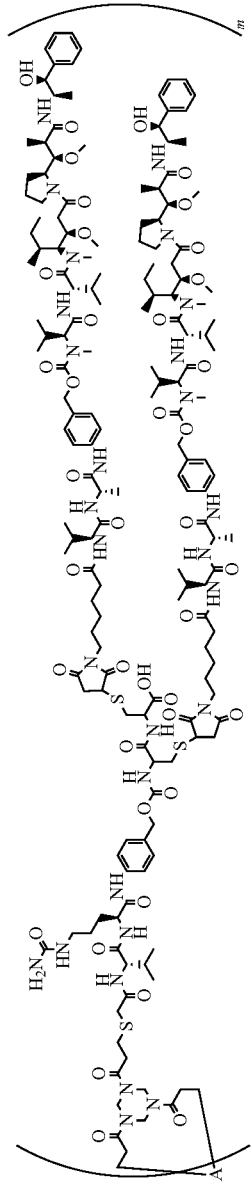
ADC-24

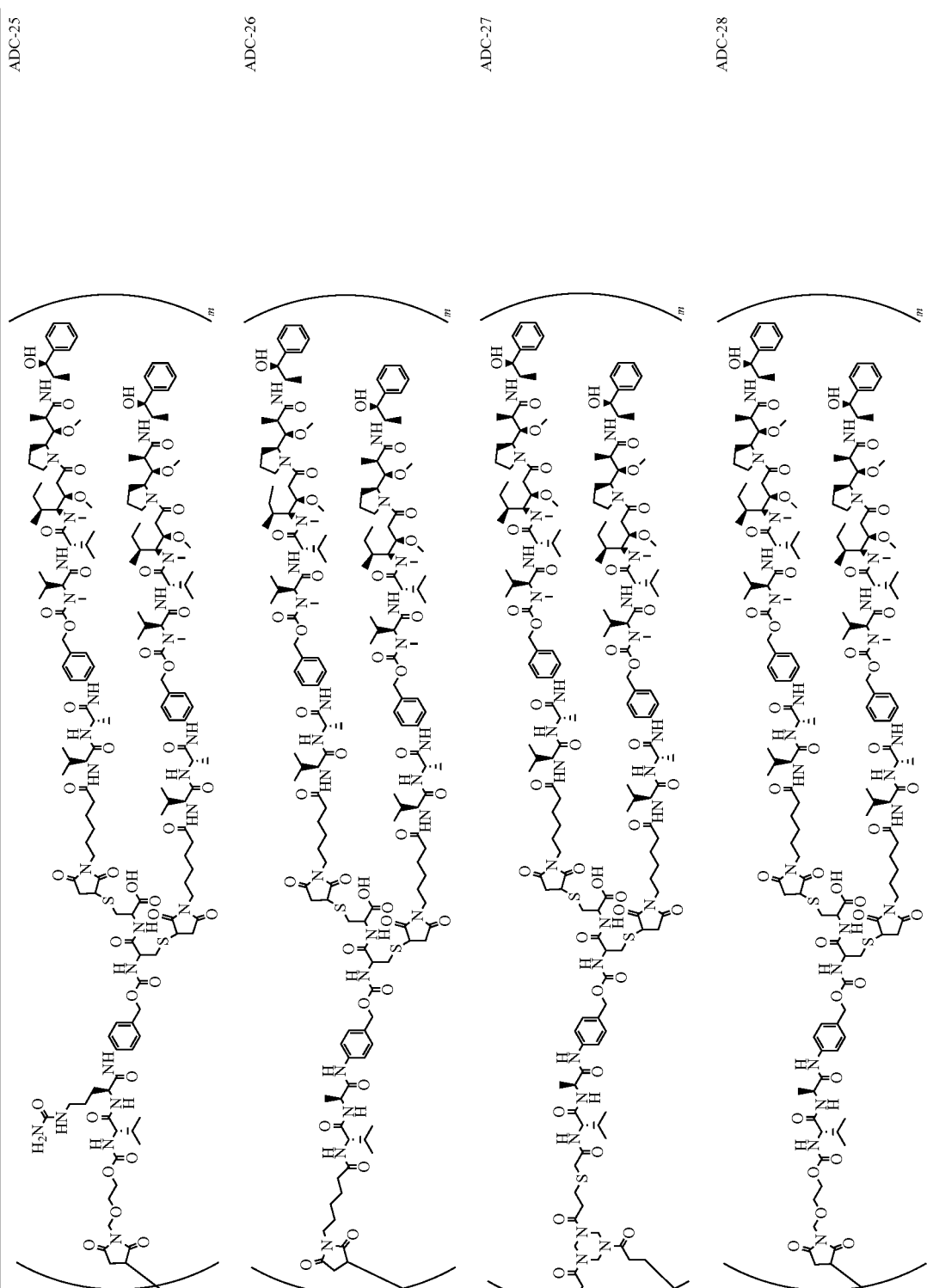

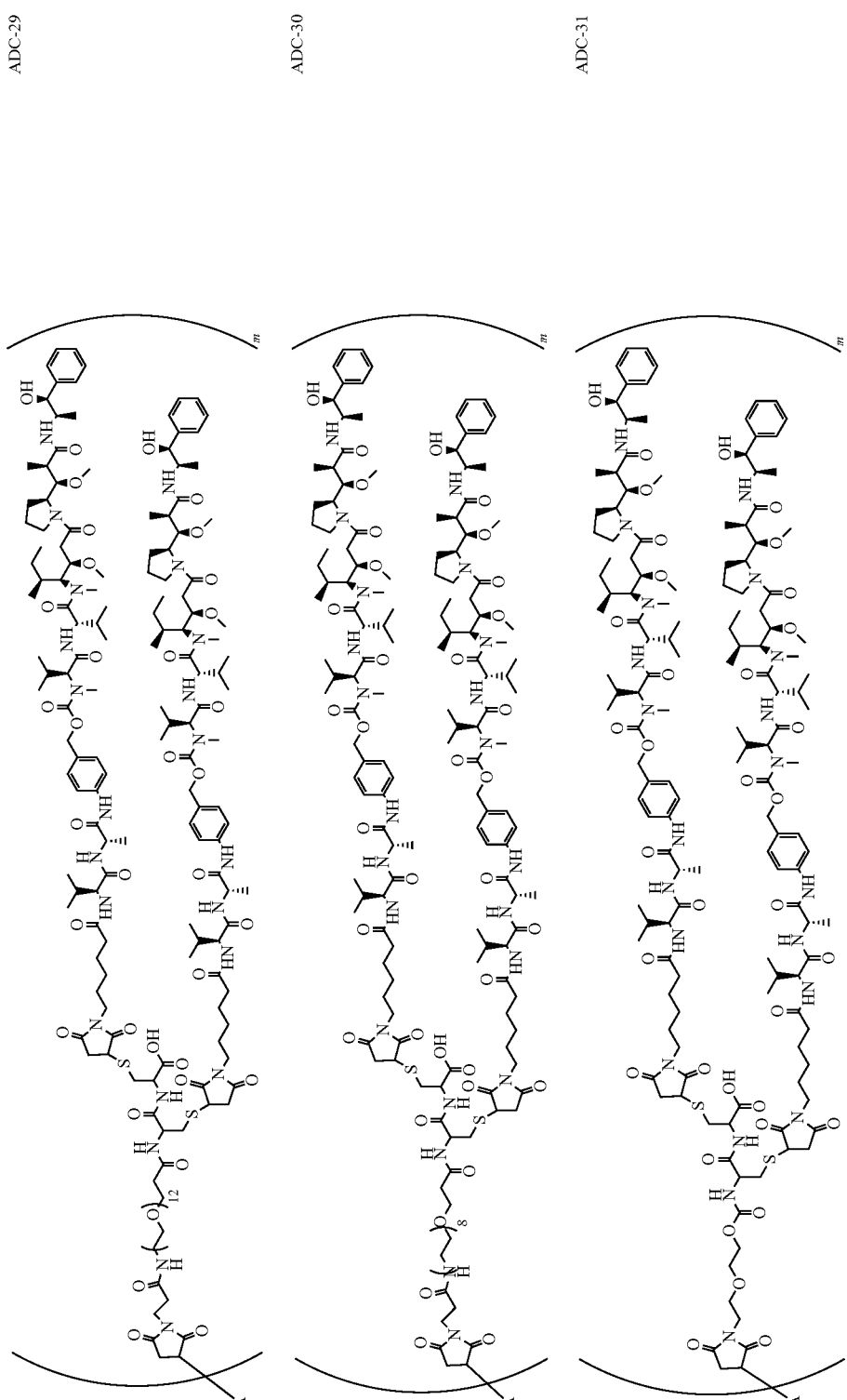

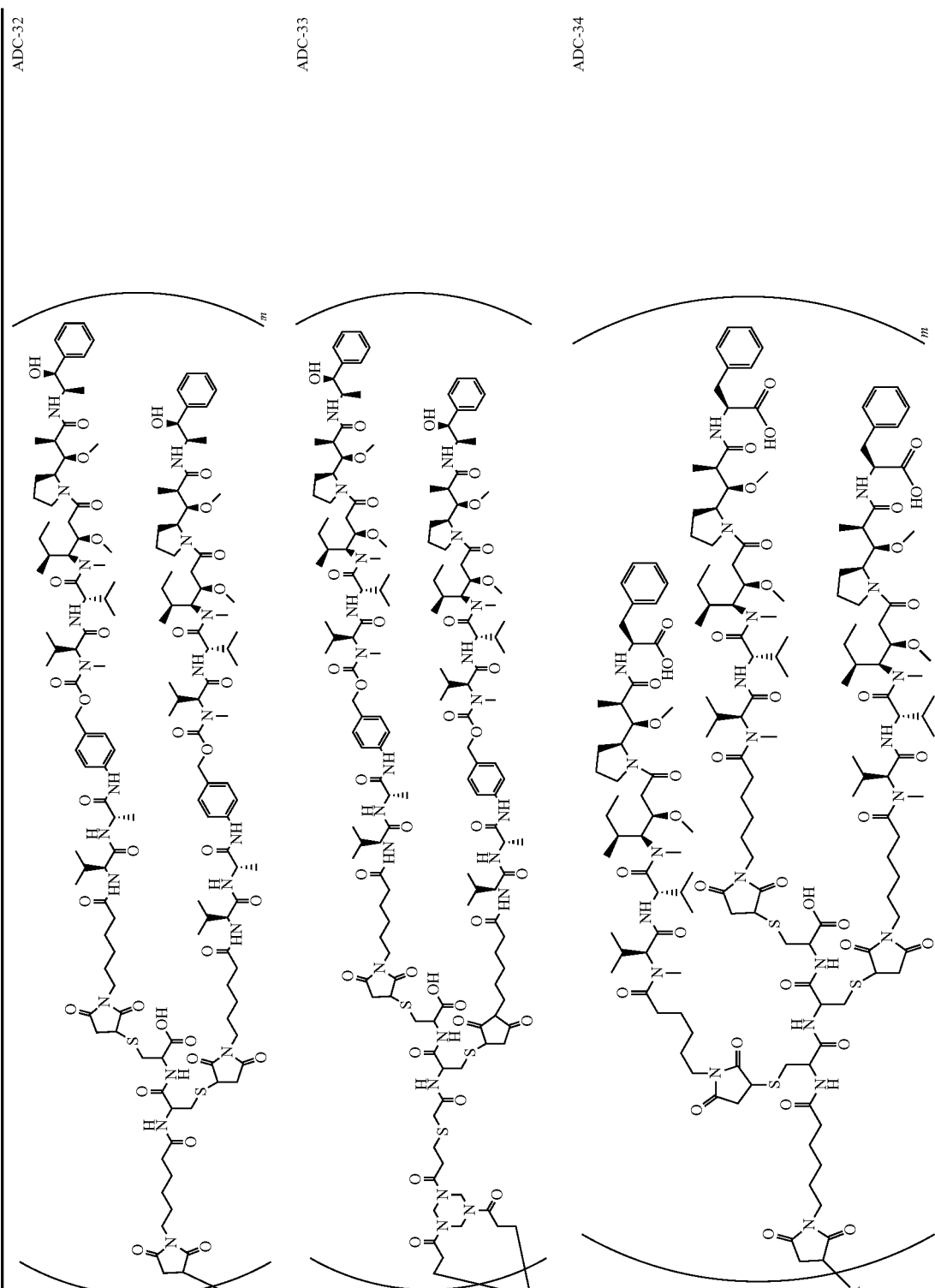

wherein,
A is an antibody or a functional binding fragment thereof; and
m is selected from 1, 2, 3, 4, 5, 6, 7, and 8.

The present disclosure also provides a pharmaceutical composition comprising an effective amount of the antibody-drug conjugate of any one of the above, or a pharmaceutically acceptable salt or solvate thereof, together with a pharmaceutically acceptable excipient.

The present disclosure also provides the use of the antibody-drug conjugate of any of the above in the preparation of a medicament for treating cancer.

The present disclosure provides an antibody-drug conjugate (ADC) using one or more cysteine or derivatives thereof as linkers to couple one or more drugs at the limited binding sites of an antibody, making it easy to produce ADCs with higher drug payload. In theory, since ADCs with higher payload can be produced, drugs for coupling may be selected from a larger range, so that drugs with lower toxicity may be used to prepare ADC products, thereby obtaining ADC products with a wide therapeutic window. In addition, since a plurality of drugs may be coupled to one binding site, the ADC products obtained by the method of the present disclosure have better uniformity in the case of same DAR value. Moreover, the amount of antibody required for production may be greatly reduced, thereby lowering the cost. Moreover, it is unexpectedly found the amount of antibody required for production may be greatly reduced, thereby lowering the cost. Compared with the antibody-drug conjugates coupled only one drug, the antibody-drug conjugates produced by the method of the present disclosure have the same inhibition or killing effect on tumor cells while using fewer drugs for coupling to the same site.

DETAILED DESCRIPTION

Definitions

Various terms related to different parts of the specification are used throughout the specification and claims. Unless otherwise indicated, such terms are given the ordinary meaning in the art. Other specifically defined terms should be understood in a manner consistent with the definitions provided herein.

As used herein, the terms "a", "an", and "the" are used according to standard practice and mean one or more, unless the context indicates otherwise. Thus, for example, "an antibody-drug conjugate" includes a combination of two or more antibody-drug conjugates and the like.

It should be understood that the word "comprise/include/contain" is used in the specification, in addition, similar terms such as "consisting of . . . " and/or "substantially consisting of . . . " is also provided.

Although numerical ranges and parameter approximations are shown in the broad scope of the present disclosure, the numerical values shown in the specific examples have been recorded as accurate as possible. However, any numerical value may contain certain errors inherently due to the standard deviations present in the respective measurements. In addition, all ranges disclosed herein should be understood as encompassing any and all subranges. For example, the recorded range of "1 to 10" should be considered as encompassing any and all subranges between the minimum 1 and the maximum 10 (including the endpoints); that is, all subranges starting with a minimum of 1 or greater, such as 1 to 6.1, and subranges ending at a maximum of 10 or less, such as 5.5 to 10, are included. In addition, any reference that is referred to as "incorporated herein" should be understood as being incorporated in its entirety.

"$-\xi-$" as used in the present disclosure refers that a group containing "$-\xi-$" is linked to other group by a chemical bond.

The linking unit and the linker in the present disclosure may be used interchangeably; active unit, drug, and poison in the present disclosure may be used interchangeably.

The term "antigen" in the present disclosure refers to any molecule that elicits an immune response or is capable of being bound by an antibody or an antigen binding molecule. The immune response may involve antibody production or activation of specific immunocompetent cells or both. Those skilled in the art will readily appreciate that any macromolecule, including almost all proteins or peptides, can act as an antigen. Generally, the antigen may be expressed endogenously, i.e., expressed by genomic DNA, or it may be expressed recombinantly, or it may be chemically synthesized. The "antigen" to which the present disclosure relates refers specifically to those tumor-associated antigens which are well known in the art and may be prepared by well-known antibody preparation methods in the art. To develop effective cell-level targets for cancer diagnosis and treatment, researchers have sought to find transmembrane or other tumor-associated polypeptides. These targets are capable of being specifically expressed on the surface of one or more cancer cells while with little or no expression on the surface of one or more non-cancer cells. Typically, such tumor-associated polypeptides are overexpressed on the surface of cancer cells with respect to the surface of non-cancer cells. Identification of such tumor-associated factors can greatly enhance the specific targeting characteristics of antibody-based treatment of cancer. Tumor-associated antigens include, but are not limited to, tumor-associated antigens (1)-(36) listed below. For convenience, antigen-related information well known in the art is indicated below, including name, other names, and Genbank accession number. Nucleic acid and protein sequences corresponding to tumor-associated antigens may be found in public databases such as Genbank. Tumor-associated antigens targeted by corresponding antibodies include all amino acid sequence variants and homologs, having at least 70%, 80%, 85%, 90%, or 95% homology to the actual confirmed sequence, or possessing completely identical biological properties and characteristics with referred tumor-associated antigen sequences. Tumor associated antigens (1)-(37) are as follows:

(1) BMPR1B (bone morphogenetic protein receptor-1B, Genbank accession No. NM_001203);

(2) E16 (LAT1, SLC7A5, Genbank accession No. NM_003486);

(3) STEAP (six transmembrane epithelial antigen of prostate 1, Genbank accession No. NM_012449);

(4) 0772P (CA125, MUC16, Genbank accession No. AF361486);

(5) MPF (MPF, MSLN, SMR, megakaryocyte potentiating factor, mesothelin, Genbank accession No. NM_005823);

(6) Napi3b (NAPI-3B, NPTIIb, SLC34A2, solute carrier family 34 (sodium phosphate) member 2, type II sodium-dependent phosphate transporter 3b, Genbank accession No. NM_006424);

(7) Sema 5b (FLJ10372, KIAA1445, Mm.42015, SEMA5B, SEMAG, brain signaling protein 5b Hlog, sema domain, seven thrombospondin repeats (type 1 and type 1-like), transmembrane domain (TM) and short cytoplasmic domain, (brain signaling protein) 5B, Genbank accession No. AB040878);

(8) PSCA hlg (2700050C12Rik, C530008016Rik, RIKEN cDNA 2700050C12, RIKEN cDNA 2700050C12 gene, Genbank accession No. AY358628);

(9) ETBR (endothelin type B receptor, Genbank accession No. AY275463);

(10) MSG783 (RNF124, hypothetical protein FLJ20315, Genbank accession No. NM_017763);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of the prostate 2, six transmembrane prostate protein, Genbank accession No. AF455138);

(12) TrpM4 (BR22450, FLJ20041, TRPM4, TRPM4B, transient receptor potential cation channel, subfamily M, member 4, Genbank accession No. NM_017636);

(13) CRIPTO (CR, CR1, CRGF, CRIPTO, TDGF1, teratoma-derived growth factor, Genbank accession No. NP_003203 or NM_003212);

(14) CD21 (CR2 (complement receptor 2) or C3DR (C3d/EB virus receptor) or Hs.73792, Genbank accession No. M26004);

(15) CD79b (CD79B, CD79O, IGb (immunoglobulin-associated beta), B29, Genbank accession No. NM_000626);

(16) FcRH2 (IFGP4, IRTA4, SPAP1A (SH2 domain containing phosphatase-anchored protein 1a), SPAP1B, SPAP1C, Genbank accession No. NM_030764);

(17) HER2 (ErbB2, Genbank accession No. M11730);

(18) NCA (CEACAM6, Genbank accession No. M18728);

(19) MDP (DPEP1, Genbank accession No. BC017023);

(20) IL20Ru (IL20Ra, ZCYTOR7, Genbank accession No. AF184971);

(21) Brevican (BCAN, BEHAB, Genbank accession No. AF229053);

(22) EphB2R (DRT, ERK, Hek5, EPHT3, Tyro5, Genbank accession No. NM_004442);

(23) ASLG659 (B7h, Genbank accession No. AX092328);

(24) PSCA (prostate stem cell antigen precursor, Genbank accession No. AJ297436);

(25) GEDA (Genbank accession No. AY260763);

(26) BAFF-R (B cell activating factor receptor, BLyS receptor 3, BR3, Genbank accession No. AF116456);

(27) CD22 (B cell receptor CD22-B isotype, Genbank accession No. AK026467);

(28) CD79a (CD79A, CD79u, immunoglobulin-associated alpha, which is capable of covalently interacting with Ig (CD79B) and form a complex with IgM molecules on the surface, transduct B cell-specific proteins involved in B cell differentiation signals, Genbank accession No. NP_001774.1);

(29) CXCR5 (Burkitt's Lymphoma Receptor 1, G-protein coupled receptor activated by CXCL13 chemokine, which plays a role in lymphocyte migration and humoral defense, in HIV-2 infection and possibly in AIDS, lymphoma, myeloma, and leukemia, Genbank accession No. NP_001701.1);

(30) HLA-DOB (beta subunit of the MHC class II molecule (Ia antigen), which binds to the peptide and presents it to CD4+ T lymphoid cells, Genbank accession No. NP_002111.1);

(31) P2X5 (purine receptor P2X ligand-gated ion channel 5, an ion channel gated by extracellular ATP, which may be involved in synaptic transmission and neuronal regeneration, and defects of which may lead to pathophysiological conditions of idiopathic detrusor instability, Genbank accession No. NP_002552.2);

(32) CD72 (B cell differentiation antigen CD72, Lyb-2, Genbank accession No. NP_001773.1);

(33) LY64 (lymphocyte antigen 64 (RP105), a family of type I membrane protein (LRR) rich in leucine repeats, which regulates B cell activation and apoptosis, and loss of function is associated with increased disease activity in patients with systemic lupus erythematosus, Genbank accession No. NP_005573.1);

(34) FcRH1 (Fc receptor-like protein 1, putative immunoglobulin Fc domain receptor, which comprises a C2-type Ig-like and ITAM domain, may play a role in B lymphocyte differentiation, Genbank accession No. NP_443170.1);

(35) IRTA2 (translocation-associated immunoglobulin superfamily receptor 2, putative immunoreceptor, which may play a role in B cell development and lymphoma production; genetic disorders caused by translocation occur in some B-cell malignancies, Genbank accession No. NP_112571.1);

(36) TENB2 (predicted transmembrane proteoglycan, associated with the EGF/heregulin family and follistatin of the growth factor, Genbank accession No. AF179274);

(37) Other related antigens.

The term "antibody" in the present disclosure is used in the broadest scope and encompasses various antibody structures including, but not limited to, a monoclonal antibody, a polyclonal antibody, a multispecific antibody (e.g., bispecific antibody), and an antibody fragment. Generally, an antibody may comprise at least two heavy chains and two light chains linked to each other by disulfide bonds, or antigen-binding fragments thereof. Each heavy chain comprises a heavy chain variable region and a heavy chain constant region. The heavy chain constant region contains three constant domains: CH1, CH2, and CH3. Each light chain comprises a light chain variable region and a light chain constant region. The light chain constant region contains a constant domain: CL. The heavy chain variable region and the light chain variable region may be further subdivided into hypervariable regions, termed complementarity determining regions (CDRs), interspersed with more conserved regions, referred to as framework regions (FR). Each heavy chain variable region and light chain variable region comprises three CDRs and four FRs, arranged from amino terminus to carboxy terminus in the following order: FR1, CDR1, FR2, CDR2, FR3, CDR3, FR4. The variable regions of the heavy chain and light chain contain a binding domain that interacts with the antigen. The constant region of Ab can mediate binding of immunoglobulins to host tissues or factors, including various cells of the immune system (e.g., effector cells) and the first component (C1q) of the classical complement system. Unless otherwise indicated, the term "antibody" in the present disclosure encompasses an intact immunoglobulin or an antigen-binding fragment thereof that competes with the intact antibody for specific binding. The antigen-binding fragment may be produced by recombinant DNA techniques or by enzymatic or chemical cleavage of an intact antibody. The antigen-binding fragments include Fab, Fab', F(ab')$_2$, Fv, a domain antibody (dAb), a fragment including a complementarity determining region (CDR), a single chain antibody (scFv), a chimeric antibody, a bivalent antibody, a trivalent antibody, a tetravalent antibody, and a polypeptide that contains at least a fragment of an immunoglobulin that is sufficient to confer specific antigen binding to the polypeptide. The term "antibodies" in the present disclosure also include a naturally occurring and a non-naturally occurring (recombinantly produced) antibodies, a human and a non-human antibodies, a monospecific antibody, a multispecific antibody (including a bispecific antibody), immunoglobulin, a synthetic antibody, a tetrameric antibody comprising two heavy and two light chain molecules, an antibody light chain monomer, an antibody heavy chain monomer, an antibody light chain dimer, an antibody heavy chain dimer, an antibody light chain-antibody heavy chain pairs, an intracellular antibody (see, e.g., Stocks, (2004) Drug Discovery Today 9(22): 960-66), an antibody fusion compound (this term encompasses an antibody-drug conjugate and sometimes refers to herein as "an antibody conjugate"), a heteroconjugate antibody, a single domain antibody, a monovalent antibody, a single chain antibody or single chain Fv (scFv), a camelized antibody, an affybody, a Fab fragment, a F(ab')$_2$ fragment, disulfide-linked Fv (sdFv), an anti-idiotypic (anti-Id) antibody (including, for example, an anti-anti-Id antibody), a minibody, a domain antibody, a synthetic antibody (sometimes referred to herein as "an antibody mimic"), and an antigen-binding fragment thereof.

The term "functional fragment" in the present disclosure refers to an antibody fragment consisting or comprising a partial sequence of a heavy or light variable chain from which the antibody is derived. The partial sequence is capable of retaining the same binding specificity as the antibody from which it is derived and sufficient affinity, preferably at least equal to 1/100 of the affinity of the antibody from which it is derived, more preferably at least 1/10. Such a functional fragment comprises a minimum of 5 amino acids, preferably 10, 15, 25, 50 and 100 contiguous amino acids of the antibody sequence from which it is derived.

The term "humanized antibody" refers to an antibody comprising a CDR region derived from a non-human antibody, and the other portion of the antibody is derived from one (or several) human antibody (antibodies). Moreover, in order to retain binding affinity, some residues of the backbone (referred to as FR) may be modified (Jones et al., Nature, 321:522-525, 1986; Verhoeyen et al., Science, 239: 1534-1536, 1988; Riechmann et al., Nature, 332: 323-327, 1988). A humanized antibody or a fragment thereof according to the present disclosure may be prepared by techniques known to those skilled in the art (for example, as described in references: Singer et al., J. Immun. 150: 2844-2857, 1992; Mountain et al., Biotechnol. Genet. Eng. Rev., 10: 1-142, 1992; or Bebbington et al., Bio/Technology, 10: 169-175, 1992).

The term "chimeric antibody" refers to an antibody in which the variable region sequence is derived from one species and the constant region sequence is derived from another species, e.g., an antibody having a variable region sequence derived from a mouse antibody and a constant region sequence derived from a human antibody. A chimeric antibody or fragment thereof according to the present disclosure may be prepared by using genetic recombination techniques. For example, the chimeric antibody may be produced by cloning recombinant DNA comprising a promoter and a sequence encoding a variable region of a non-human, in particular murine, monoclonal antibody according to the present disclosure, as well as a sequence encoding a constant region of a human antibody. The chimeric antibody of the present disclosure encoded by such a recombinant gene will be, for example, a murine-human chimera whose specificity is determined by the variable region derived from murine DNA, and whose isotype is determined by the constant region derived from human DNA. For methods of preparing chimeric antibodies, for example, reference may be made to Verhoeyn et al. (BioEssays, 8: 74, 1988).

The term "monoclonal antibody" refers to a preparation of an antibody molecule having a single molecular composition. A monoclonal antibody displays a single binding specificity and affinity for a particular epitope.

In some specific examples, the antibodies of the present disclosure include, but is not limited to: muromonab-CD3, abciximab, rituximab, daclizumab, palivizumab, infliximab, trastuzumab, etanercept, basiliximab, gemtuzumab, alemtuzumab, ibritumomab, adalimumab, alefacept, omalizumab, efalizumab, tositumomab, cetuximab, ABT-806, bevacizumab, natalizumab, ranibizumab, panitumumab, eculizumab, rilonacept, certolizumab, romiplostim, AMG-531, golimumab, ustekinumab, ABT-874, belatacept, belimumab, atacicept, anti-CD20 antibody, canakinumab, tocilizumab, atezolizumab, mepolizumab, pertuzumab, HuMax CD20, tremelimumab, ticilimumab, ipilimumab, IDEC-114, intuzumab, HuMax EGFR, aflibercept, HuMax-CD4, teplizumab, otelixuzumab, catumaxomab, anti-EpCAM antibody IGN101, adakimumab, oregovomab, dinutuximab, girentuximab, denosumab, bapineuzumab, motavizumab, efumgumab, raxibacumab, LY2469298 and veltuzumab.

The term "linker" in the present disclosure refers to a molecule having a bifunctional group or a polyfunctional group, which can react with a protein/an antibody molecule and a drug molecule, respectively, and thus serves as a "bridge" for linking a protein/an antibody with a drug molecule. According to the mechanism of drug release in cells, "linker" or "linker of an antibody-drug conjugate" may be divided into two classes: non-cleavable linker and cleavable linker.

The non-cleavable linker is a relatively stable linker whose structure is difficult to be degraded or broken in vivo. For an antibody-drug conjugate containing a non-cleavable linker, the drug release mechanism is: the conjugate binds to the antigen and then is taken by endocytosis; the antibody is hydrolyzed in the lysosome, and an active molecule composed of the small molecule drug, the linker, and amino acid residues of the antibody is released. The resulting change in the structure does not diminish the cytotoxicity of the drug. However, since the active molecule is charged (due to the amino acid residues), it cannot penetrate into adjacent cells. Therefore, such active drugs cannot kill adjacent tumor cells which do not express the target antigen (antigen-negative cells) (bystander effect) (Bioconjugate Chem. 2010, 21, 5-13). Common non-cleavable linkers are MC linkers and MCC linkers, etc.:

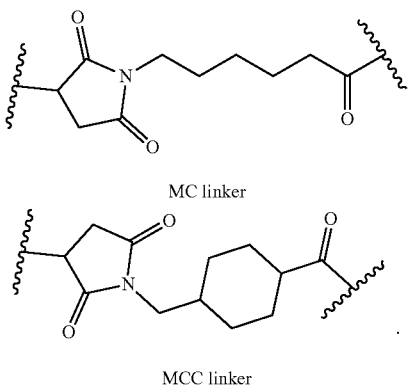

MC linker

MCC linker

A cleavable linker, as the name implies, may be cleaved in the target cells and release the active drug (the small molecule drug itself). A cleavable linker may be divided into two main classes: chemically labile linker and enzyme-labile linker.

A chemically labile linker may be selectively cleaved due to different plasma and cytoplasmic properties. Such properties include pH, glutathione concentration, and the like.

A pH-sensitive linker, is often referred to an acid-labile linker. Such a linker is relatively stable in the neutral environment of blood (pH 7.3-7.5), but will be hydrolyzed in slightly acidic endosomes (pH 5.0-6.5) and lysosomes (pH 4.5-5.0). Most of the first generation of antibody-drug conjugates used this type of linker, such as hydrazone, carbonate, acetal, ketals. Antibody-drug conjugates using this type of linker typically have a shorter half-life (2-3 days) due to the limited stability of the acid-labile linker in plasma. This short half-life limits the use of the pH-sensitive linker in new generation of antibody-drug conjugates to some extent.

A glutathione-sensitive linker, is also known as a disulfide linker. Drug release is caused by the difference between the high concentration (in millimolar range) of intracellular glutathione and the relatively low concentration of glutathione (micromolar range) in the blood. This is especially the case for tumor cells, in which low oxygen content result in enhanced reductase activity, thus resulting in higher glutathione concentration. Disulfide bond is thermodynamically stable and therefore has better stability in plasma.

An enzyme-labile linker, such as a peptide linker, is capable of controlling drug release better. The peptide linker is capable of being efficiently cleaved by a protease in lysosomes such as Cathepsin B or plasmin (the content of such enzyme is increased in some tumor tissues). This peptide linkage is believed to be very stable in the plasma circulation because the extracellular inappropriate pH as well as serum protease inhibitors generally make the protease to be inactivated outside the cell. In view of the high plasma stability and good intracellular cleavage selectivity and effectiveness, enzyme-labile linkers are widely used as cleavable linkers for antibody-drug conjugates. Typical enzyme-labile linkers are vc linkers and the like.

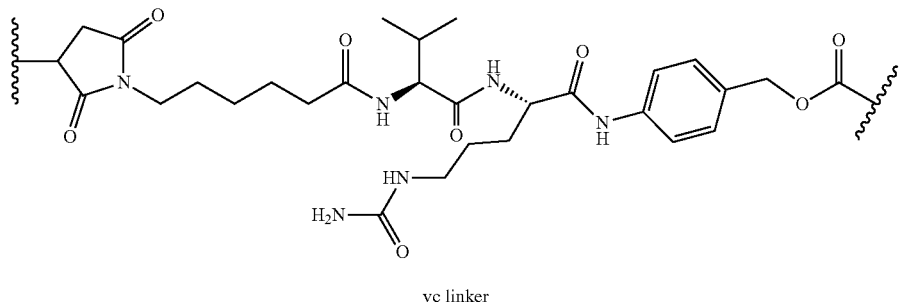 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

vc linker

A suicide linker is typically chimeric between a cleavable linker and an active drug, or itself a part of the cleavable linker. The mechanism of the suicide linker is that when the cleavable linker is broken under suitable conditions, the suicide linker can spontaneously perform structure rearrangement to release the active drug linked thereto. Common suicide linkers are such as p-aminobenzyl alcohols (PABs).

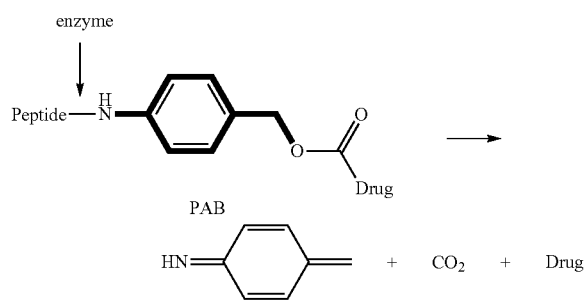

The term "active drug" in the present disclosure broadly refers to any compound having desired biological activity and a reactive functional group for producing the conjugate of the present disclosure. The desired biological activity includes an ability of diagnosing, curing, alleviating, treating, preventing diseases in humans or other animals. As novel drugs are continuously discovered and developed, these new drugs should also be incorporated in the drugs of the present disclosure. Specifically, the drugs include, but are not limited to, a cytotoxic drug, a cell differentiation factor, a stem cell trophic factor, a steroids drug, a drug for treating an autoimmune disease, an anti-inflammatory drug or a drug against an infectious disease. More specifically, the drugs include, but are not limited to, a tubulin inhibitor or a DNA, RNA damaging agent. Preferably, the active drugs involved in the present disclosure include, but are not limited to, the following:

(a) erlotinib, bortezomib, fulvestrant, sutent, letrozole, imatinib mesylate, PTK787/ZK222584, oxaliplatin, 5-fluorouracil, folinic acid, rapamycin, lapatinib, lonafanib, sorafenib, gefitinib, AG1478, AG1571, thiotepa, cyclophosphamide, busulfan, improsulfan, piposulfan, benzodopa, carboquone, meturedopa, uredopa, ethyleneimine, altretamine, triethylene melamine, triethylene phosphoramide, triethylene thiophosphoramide, trimethylol melamine, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatine, sarcodictyin, spongistatin, chlorambucil, chlornaphazine, cholophosphamide, estramustine, ifosfamide, dichloromethyl diethylamine, melphalan, novembichin, phenesterine, prednimustine, trofosfamide, uracil mustard, carmustine, chlorozotocin, fotemustine, lomustine, nimustine, ranimnustine, calicheamicin, calicheamicin γ1, calicheamicin ω1, dynemicin, dynemicin A, clodronate, esperamicin, neocarzinostatin chromophore, aclacinomysin, actinomycin, authrarmycin, azaserine, bleomycin, actinomycin C, carabicin, carminomycin, carzinophillin, chromomycin, dactinomycin, daunorubicin, detorubicin, 6-diazo-5-oxo-L-norleucine, adriamycin, morpholino adriamycin, cyanomorpholino adriamycin, 2-pyrrolino-adriamycin, liposomal adriamycin, deoxyadriamycin, epirubicin, esorubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aldophosphamide glycoside, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, etoglucid, gallium nitrate, hydroxyurea, lentinan, lonidamine, maytansine, ansamitocin, mitoguazone, mitoxantrone, mopidanmol, nitraerine, pentostatin, phenamet, pirarubicin, losoxantrone, 2-ethyl hydrazide, procarbazine, polysaccharide-k, razoxane, rhizomycin, sizofiran, spirogermanium, tenuazonic acid, triaziquone, 2,2',2''-trichlorotriethylamine, T-2 toxin, verracurin A, roridin A, and anguidine, urethane, vindesine, dacarbazine, mannomustine, dibromomannitol, mitolactol, pipobroman, dry cytosine, arabinoside, cyclophosphamide, thiotepa, paclitaxel, albumin engineering nanoparticle preparation of paclitaxel, docetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, mitoxantrone, teniposide, edatraxate, daunomycin, aminopterin, xeloda, ibandronate, CPT-11, topoisomerase inhibitor RFS 2000, difluoromethylornithine, retinoic acid, capecitabine, or any pharmaceutically acceptable salts, solvates or acids thereof;

(b) monokine, lymphokine, traditional polypeptide hormone, parathyroid hormone, thyroxine, relaxin, prorelaxin, glycoprotein hormone, follicle stimulating hormone, thyroid stimulating hormone, luteinizing hormone, liver growth factor, fibroblast growth factor, prolactin, placental lactogen, tumor necrosis factor-α, tumor necrosis factor-β, müllerian inhibiting substance, mouse gonadotropin-related peptide, inhibin, activin, vascular endothelial growth factor, thrombopoietin, erythropoietin, an osteoinductive factor, interferon, interferon-α, interferon-β, interferon-γ, colony stimulating factor ("CSF"), macrophage-CSF, granulocyte-macrophage-CSF, granulocyte-CSF, interleukin (IL), IL-1, IL-1α, IL-2, IL-3, IL-4, IL-5, IL-6, IL-7, IL-8, IL-9, IL-10, IL-11, IL-12, tumor necrosis factor, TNF-α, TNF-β, polypeptide factor, LIF, kit ligand, or any combination thereof;

(c) diphtheria toxin, botulinum toxin, tetanus toxin, dysentery toxin, cholera toxin, amanitin, amanitin derivatives, α-amanitin, pyrrolobenzodiazepine, pyrrolobenzodiazepine derivatives, tetrodotoxin, brevetoxin, ciguatoxin, ricin, AM toxin, microtubulin lysin, geldanamycin, a compound of maytansines, calicheamicin, daunorubicin, adriamycin, methotrexate, vindesine, SG2285, dolastatin, an analogue of dolastatin, auristatin, cryptophycin, camptothecin, a derivative and a metabolite of camptothecin, rhizomycin, a derivative of rhizomycin, CC-1065, an analogue or a derivative of CC-1065, duocarmycin, enediyne antibiotics, esperamicin, epothilone, azonafide, aplidin, toxoid, or any combination thereof;

(d) an affinity ligand, wherein the affinity ligand is a substrate, an inhibitor, a stimulant, a neurotransmitter, a radioisotope, or any combination thereof;

(e) a radioactive label, 32P, 35S, a fluorescent dye, an electron dense reagent, an enzyme, biotin, streptavidin, digitoxin, hapten, an immunogenic protein, a nucleic acid molecule having a sequence complementary to the target, or any combination thereof;

(f) an immunomodulatory compound, an anticancer agent, an antiviral agent, an antibacterial agent, an antifungal agent, and an antiparasitic agent, or any combination thereof;

(g) tamoxifen, raloxifene, droloxifene, 4-hydroxytamoxifen, trioxifene, naloxifene, LY117018, onapristone or toremifene;

(h) 4(5)-imidazole, aminoglutethimide, megestrol acetate, exemestane, letrozole or anastrozole;

(i) flutamide, nilutamide, bicalutamide, leuprolide, goserelin or troxacitabine;

(j) an aromatase inhibitor;

(k) a protein kinase inhibitor;

(l) a lipid kinase inhibitor;

(m) an antisense oligonucleotide;

(n) a ribozyme;

(o) a vaccine; and (p) an anti-angiogenic agent.

In some embodiments of the present disclosure, the "active drug" is selected from the group consisting of: maytansines, V-ATPase inhibitors, pro-apoptotic agents, Bel2 inhibitors, McL1 inhibitors, HSP90 inhibitors, IAP inhibitors, mTOr inhibitors, microtubule stabilizers, microtubule destabilizers, auristatins, dolastatins, MetAP (methionine aminopeptidase), nuclear output inhibitors of protein CRM1, DPPIV inhibitors, proteasome inhibitors, inhibitors of the phosphoryl transfer reaction in mitochondria, protein synthesis inhibitors, kinase inhibitors, CDK2 inhibitors, CDK9 inhibitors, kinesin inhibitors, HDAC inhibitors, DNA damaging agents, DNA alkylating agents, DNA intercalating agents, DNA minor groove binders, DHFR inhibitors, as well as dolastatin peptides, vitamin A precursors, and folic acid.

In some embodiments of the present disclosure, the "active drug" is a cytotoxic drug (e.g., an antimetabolite, an antitumor antibiotic, an alkaloid), an immunopotentiator or a radioisotope. Preferably, the drug may be selected from the group consisting of amanitins, anthracyclines, baccatins, camptothecins, cematotins, colchicines, colcimids, combretastatins, cryptophycins, discodermolides, docetaxel, doxorubicin, echinomycins, eleutherobins, epothilones, estramustines, lexitropsins, maytansines, methotrexate, netropsins, puromycins, rhizoxins, taxanes, tubulysins, or vinca alkaloids. More preferably, the drug may be selected from the group consisting of MMAD (Monomethyl auristatin D) and derivatives thereof, MMAE (Monomethyl auristatin E) and derivatives thereof, MMAF (Monomethyl auristatin F) and derivatives thereof, Merdensine derivative M1, Mertansine derivative M4, Duocarmycine and derivatives thereof, Calicheamicin and derivatives thereof, PBDA (Pyrrolobenzodiazepines), Doxorubicin, Vinca Alkaloids, Metrotrexate, Vinblastine, Daunorubicin and derivatives thereof, tubulinsins and derivatives thereof.

In some specific examples, the "active drug" is maytansine or maytansinoids. Maytansine inhibits cell proliferation by inhibiting tubulin forming microtubule (Science 1975, 189, 1002-1005; U.S. Pat. No. 5,208,020). Maytansinoids are derivatives of maytansine. Both maytansine and maytansinoids are highly cytotoxic, but they have significant limitations in the clinical application of cancer therapy, mainly due to the low tumor selectivity of these molecules. However, this high cytotoxicity has made them the preferred drug moieties for antibody-drug conjugates. Listed below are maytansine, maytansinoids, and three molecular structures of maytansinoids that are often utilized in antibody-drug conjugate applications.

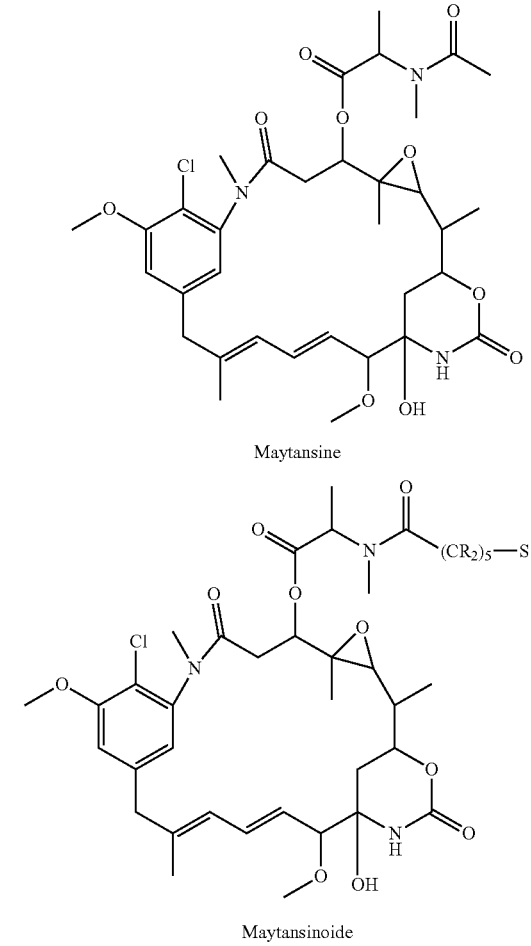

Maytansine

Maytansinoide

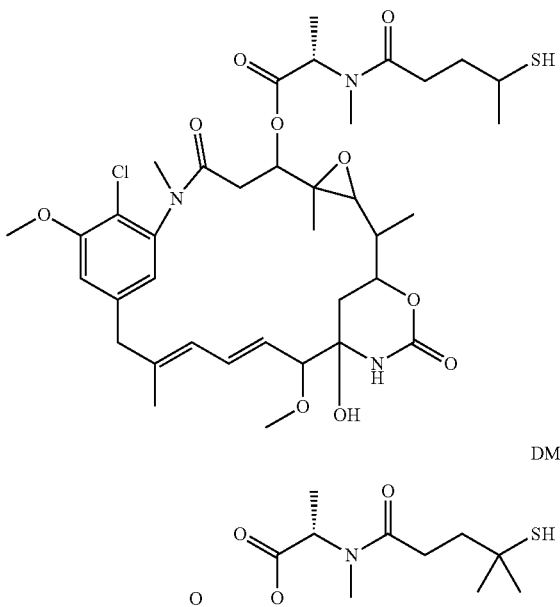

DM3

DM4

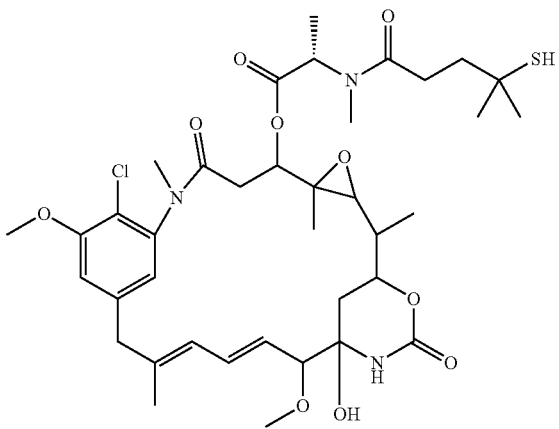

The main raw material for synthesis of maytansinoids is maytansinol, which is mainly obtained by hydrolysis of ansamitocins. Ansamitocins may be obtained by fermentation. Ansamitocins derivatives (WO 2012/061590) and alanyl maytansinol (US 2012/0121615) are also reported as drug for antibody-drug conjugates.

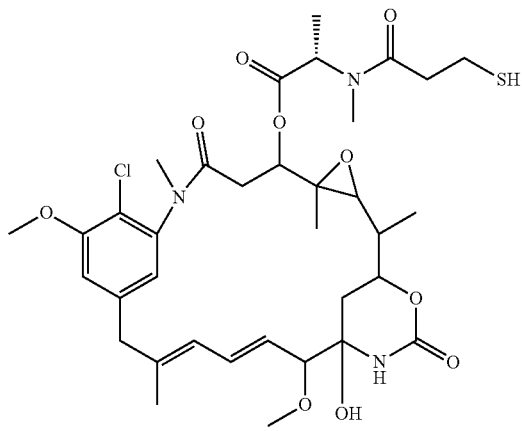

DM1

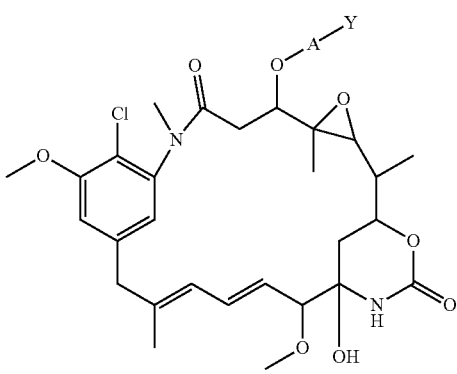

A is C=O, (C=O)NR', and (C=O)O
Y is a substituent group
Ansamitocin derivatives

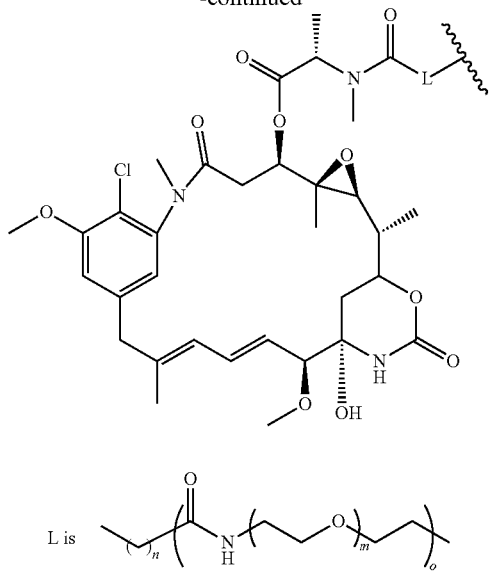

Alaninyl maytansinol

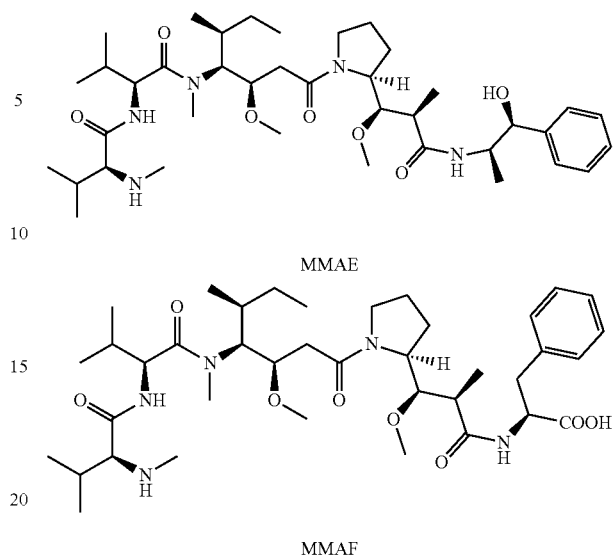

MMAE

MMAF

In some specific examples, the "active drug" is auristatins. The auristatins are analogs of dolastatin 10 which is a bioactive polypeptide isolated from a marine mollusc sea hare (U.S. Pat. No. 7,498,298). Dolastatin 10 inhibits tubulin polymerization by binding to tubulin (the same binding region as vincristine). Dolastatin 10, auristatin PE, and auristatin E are all linear polypeptides containing four amino acids (three are unique among the dolastatins compounds) and a C-terminal amide group. Two representative auristatins, monomethyl auristatin E (MMAE) and monomethyl auristatin F (MMAF), both are the preferred drug moieties for antibody-drug conjugates.

In some specific examples, the "active drug" is Tubulysins. Tubulysins are a class of natural products extracted from myxobacteria, which can effectively inhibit the polymerization of tubulin and thus having an anti-mitosis activity. Among Tubulysins, Tubulysin D has the best activity. Tubulysin D is a tetrapeptide compound that contains O-acyl/N,O-acetal functional groups in its structure and therefore it is unstable under both acidic and basic conditions. US 2011/0021568 and US 2013/0224228, respectively, disclose series of analogues of Tubulysin, in which the above-mentioned labile functional groups are removed while the high cell viability is retained.

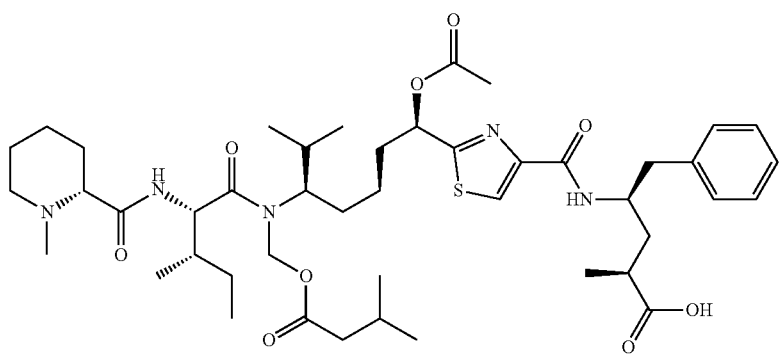

Tubulysin D

In some specific examples, the "active drug" is calicheamicins. Calicheamicins are anti-tumor antibiotics that cause apoptosis by binding to the minor groove of the DNA and promoting the cleavage of the double-helix DNA at a specific site. Calicheamicins have a high activity at the sub-picmole level in vitro while a low therapeutic index, which precludes its clinical applications. However, this high activity makes them ideal candidates for antibody-drug conjugates (such as gemtuzumab and Inotuzumab Ozogamicin).

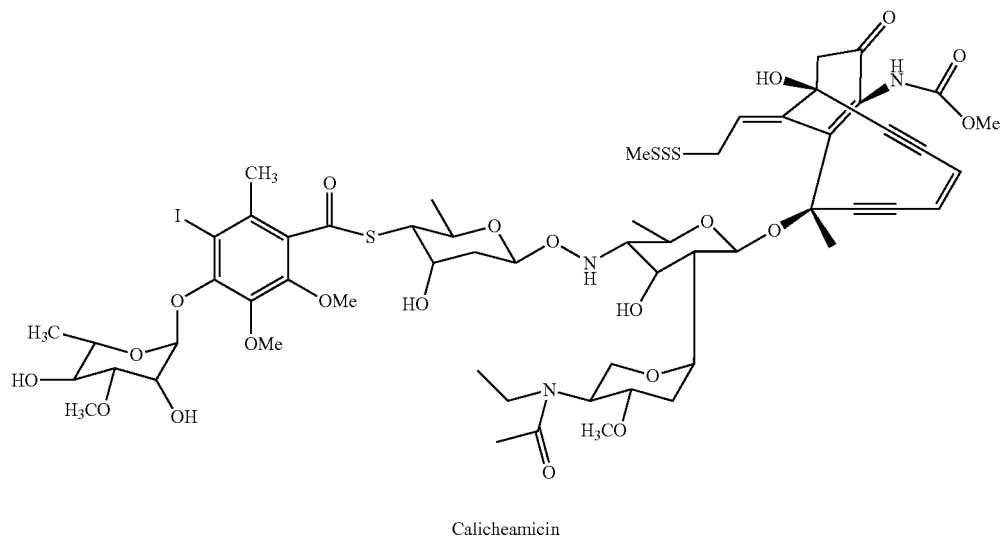

Calicheamicin

In some specific examples, the "active drug" doxorubicins. Doxorubicin is used as a chemotherapy drug because it can be intercalated into DNA double helix structure to block DNA replication. However, due to the low cytotoxicity of doxorubicins (for human-derived cancer cell lines, the median inhibitory concentration is 0.1-0.2 micromolar, whereas the cytotoxic drugs for antibody-drug conjugates usually have an activity level of sub-nanomolar), it is not widely use in antibody-drug conjugates.

propapyrroloind-4-one (CPI) derivatives. These compounds are potent agents for DNA minor groove binding and alkylating. Cyclopropabenzindol-4-one (CBI) analogues have a more stable chemical structure, higher biological activity, and are easier to be synthesized as compared with their parent compounds containing natural CPI alkylated subunits. A representative CBI derivative is phenolic hydroxyl protected derivative CBI (see figure below) with weakened prodrug toxicity and enhanced water solubility.

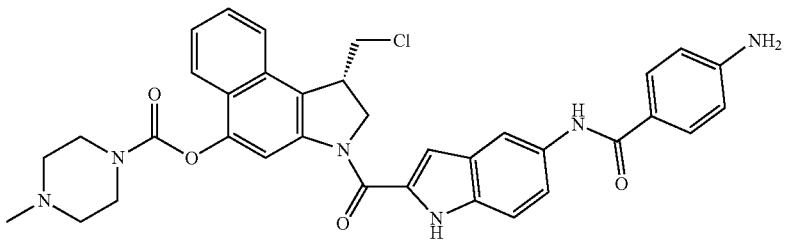

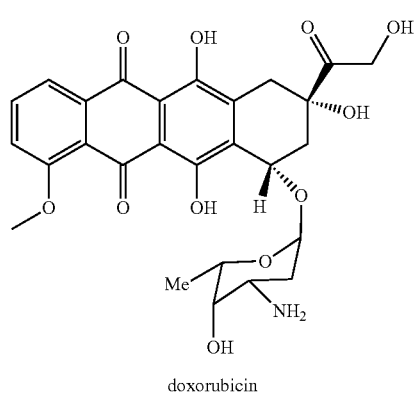 [SMILES: COc1cccc2c1C(=O)c1c(O)c3c(c(O)c1C2=O)C[C@@](O)(C(=O)CO)C[C@@H]3OC1CC(N)C(O)C(C)O1]

doxorubicin

In some specific examples, the "active drug" is benzodipyrroles (duocarmycins, CC-1065, etc.) and other cyclo- In some specific examples, the "active drug" is pyrrolo[2,1-c][1,4]benzodi-azepines (PBDs) or PBD dimers. The PBD is a class of natural products produced by *Streptomyces*, and its unique feature is the ability to form non-twisted covalent additions in the DNA minor groove, specifically at the purine-guanine-purine sequence. The use of PBD as a small molecule for targeting DNA sequences and as a novel anticancer and antibacterial drug has attracted increasing interest (Biochemistry 2008, 47, 11818-11829). A flexible carbon chain is used to link the C8/C8' hydroxyl groups of the two PBD units, and the resulting dimer has enhanced biological activity (WO 2011/130616). PBD dimer is believed that it may generate sequence-selective DNA damage, such as reversed 5'-Pu-GATC-Py-3' interstrand cross-linking, resulting in its biological activity. These compounds have been proven to be highly potent cytotoxic drugs and may be used as candidates for antibody-drug conjugates.

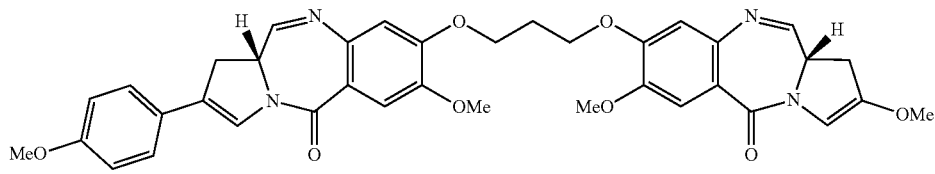

SG2201

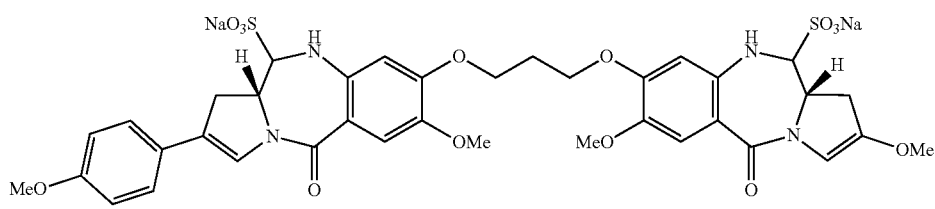

SG2285

In other specific examples, the "active drug" is not limited to the classes mentioned above, but also includes all drugs usable for antibody-drug conjugates.

The term "pharmaceutical composition" in the present disclosure means a combination of at least one drug and optionally a pharmaceutically acceptable carrier or excipient that are combined together to achieve a particular purpose. In some embodiments, the pharmaceutical composition includes combinations that are separated in time and/or space, as long as they are capable of acting together to achieve the objectives of the present disclosure. For example, the components of the pharmaceutical composition may be administered to the subject as a whole or separately. When the components of the pharmaceutical composition are administered to a subject separately, the components may be administered to the subject simultaneously or sequentially. Preferably, the pharmaceutically acceptable carrier is water, a buffered aqueous solution, an isotonic saline solution such as PBS (phosphate buffer), glucose, mannitol, dextrose, lactose, starch, magnesium stearate, cellulose, magnesium carbonate, 0.3% glycerol, hyaluronic acid, ethanol or polyalkylene glycol such as polypropylene glycol, triglyceride and the like. The type of the pharmaceutically acceptable carrier employed depends inter alia on whether the composition according to the present disclosure is formulated for oral, nasal, intradermal, subcutaneous, intramuscular or intravenous administration. The composition according to the present disclosure may comprise a wetting agent, an emulsifier or a buffer substance as an additive.

The pharmaceutical composition, vaccine or pharmaceutical preparation of the present disclosure may be administered by any suitable route, for example, administered orally, nasally, intradermally, subcutaneously, intramuscularly or intravenously.

The term "effective amount" in the present disclosure encompasses an amount sufficient to ameliorate or prevent a symptom or condition of a medical disease. An effective amount also means an amount sufficient to allow or facilitate the diagnosis. An effective amount for a particular patient or veterinary subject can vary depending on factors such as the condition to be treated, the overall health of the patient, the methodological route and dosage of the administration, and the severity of the side effects. An effective amount may be the maximum dose or dosing regimen that avoids significant side effects or toxic effects.

EXAMPLES

The present disclosure is further illustrated below in conjunction with specific examples. It is to be understood that the examples are used to illustrate the present disclosure only, and not intended to limit the scope of the present disclosure. The experimental methods in the following examples, which do not specify the specific conditions, are usually carried out according to conventional conditions or according to the conditions recommended by the manufacturer, and reagents of unspecified origin are conventional reagents which are commercially available. All percentages, rates, ratios, or parts are by weight unless otherwise indicated.

The unit of weight by volume in the present disclosure is well known to those skilled in the art and, for example, refers to the weight of the solute in a 100 ml solution.

Unless otherwise defined, all the disciplines and sciences terms used herein have the same meanings as known by those skilled in the art. In addition, any methods and materials similar or equivalent to those recited may be applied to the methods of the present disclosure. The preferred examples and materials described herein are for illustrative purposes only.

Example 1. Preparation of Compound 1

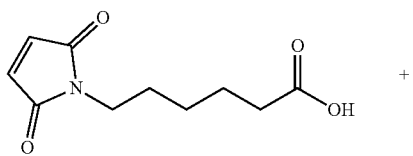

maleimido caproic acid

+

-continued

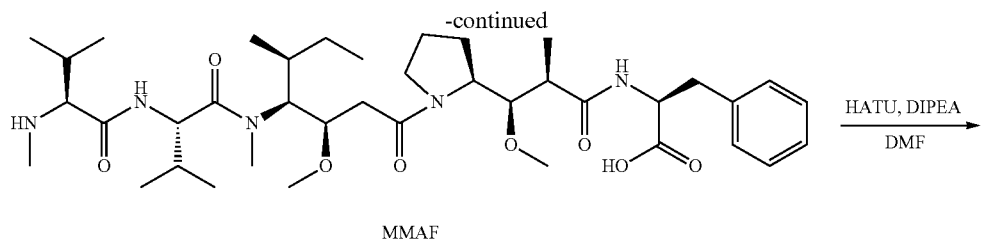

MMAF

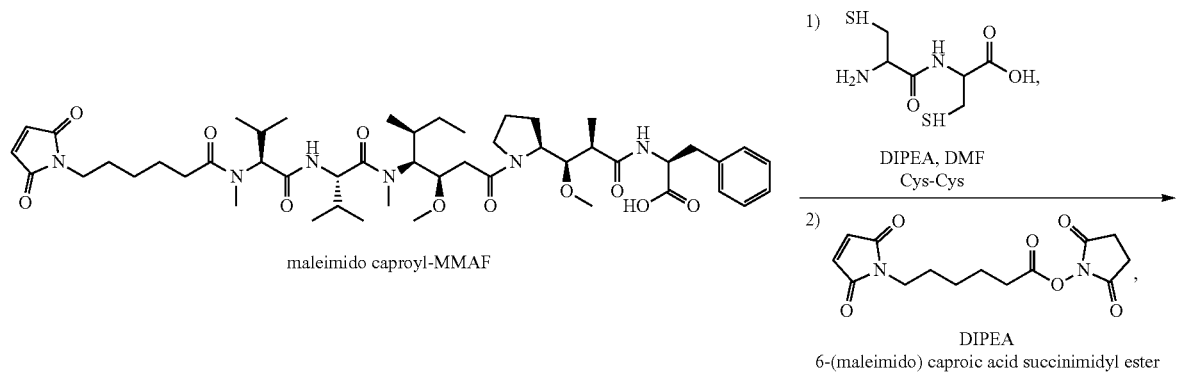

maleimido caproyl-MMAF 6-(maleimido) caproic acid succinimidyl ester

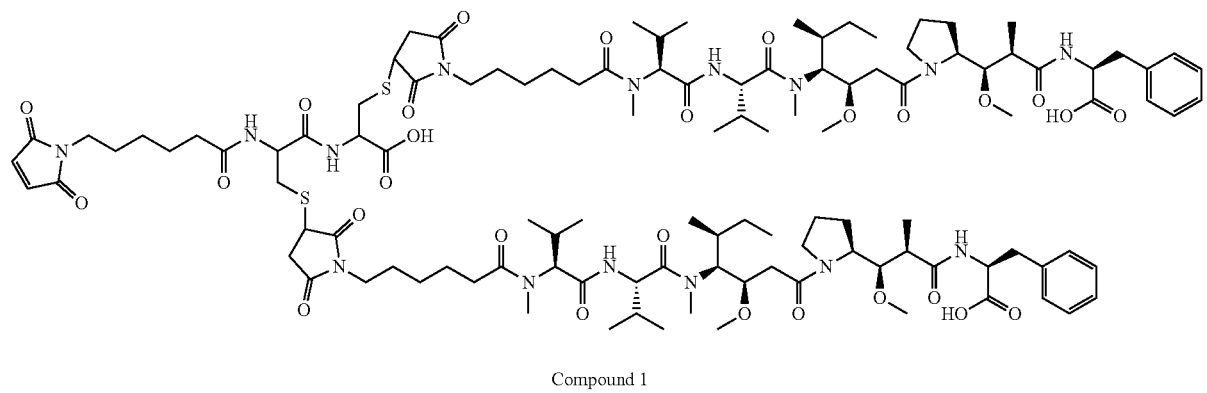

Compound 1

145.4 mg of maleimide caproic acid was dissolved in 10 mL of DMF, 244.7 mg of HATU and 226 μL of DIPEA were added and stirred at room temperature. 201.9 mg of MMAF was dissolved in 5 mL of DMF and slowly added dropwise to the above reaction system, and the mixture was stirred at room temperature for 16 h. The solvent was distilled off under reduced pressure, and purification was performed by preparative liquid chromatography to obtain 90.3 mg product (maleimidocaproyl-MMAF, Mc-MMAF), with a yield of 36%. LC-MS: $(M+H)^+$ 924.8, $(M-H)^-$ 923.2.

36.1 mg of maleimidocaproyl-MMAF was dissolved in 1.5 mL DMF, 5.6 mg Cys-Cys and 2.1 μL DIPEA were added, and the mixture was stirred at room temperature for 3 h. 1.1 mg Cys-Cys was added and the mixture was stirred at room temperature for 2 h. 17.7 mg of 6-(maleimido) caproic acid succinimidyl ester and 25 μL of DIPEA were added and the mixture was stirred at room temperature for 15 h. The solvent was distilled off under reduced pressure, and purification was performed by preparative liquid chromatography to obtain 20.0 mg of Compound 1, with a yield of 45%. LC-MS: $(M+2H)^{2+}$ 1134.1, $(M-2H)^{2-}$ 1132.2.

Example 2. Preparation of Compound 2

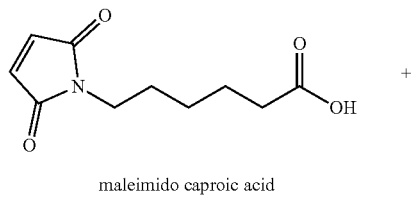

maleimido caproic acid

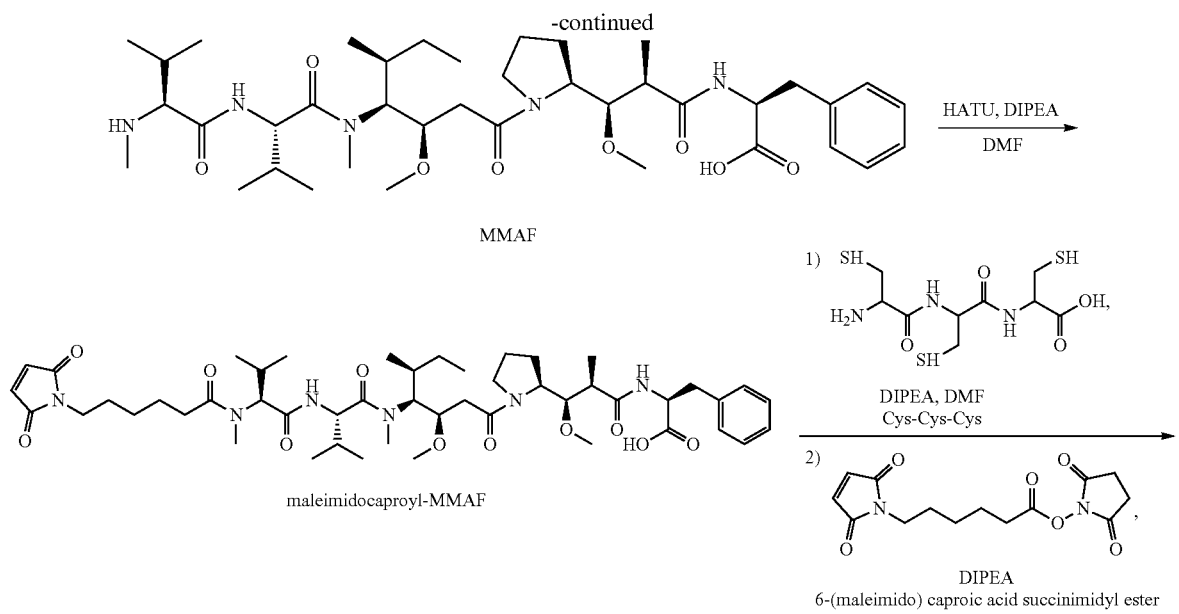

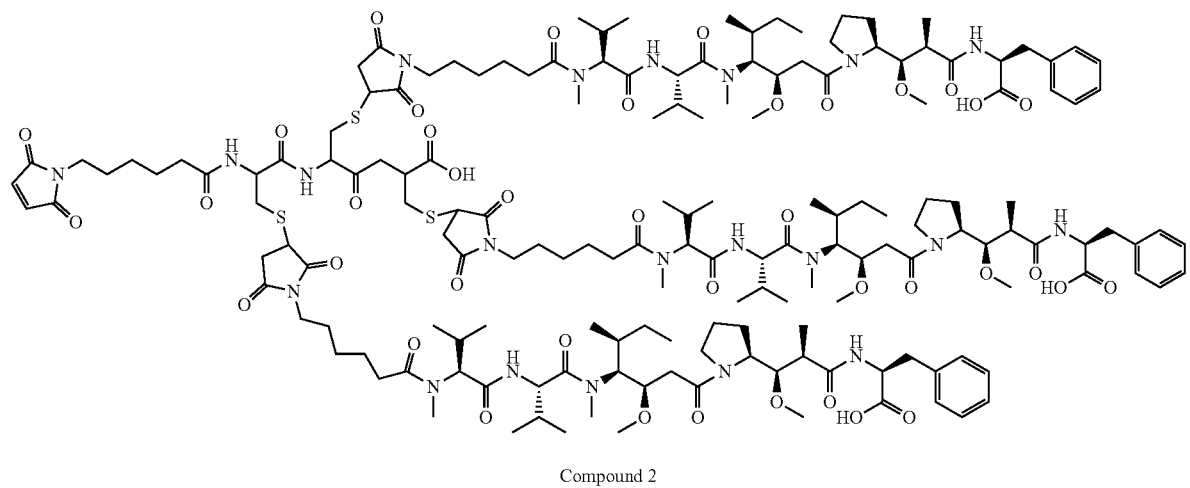

Compound 2

Maleimidocaproyl-MMAF was prepared in accordance with the method of Example 1. 40.1 mg of maleimidocaproyl-MMAF was dissolved in 1.5 mL of DMF, 4.4 mg of Cys-Cys-Cys and 2.1 μL of DIPEA were added, and the mixture was stirred at room temperature for 2 h. 1.8 mg of Cys-Cys-Cys was added, and the reaction was continued at room temperature for 2 h. 0.9 mg of Cys-Cys-Cys was added and the reaction was continued at room temperature for 2 h. 13.5 mg of 6-(maleimido)caproic acid succinimidyl ester and 21 μL of DIPEA were added and the mixture was stirred at room temperature for 15 h. The solvent was distilled off under reduced pressure and purification was performed by preparative liquid chromatography to obtain 23.1 mg of Compound 2, with a yield of 49%. LC-MS: $(M+3H)^{3+}$ 1648.4, $(M-3H)^{3-}$ 1646.3.

Example 3. Preparation of Compound 3

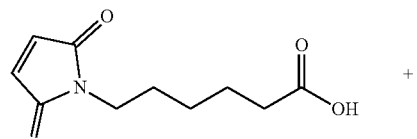

maleimido caproic acid

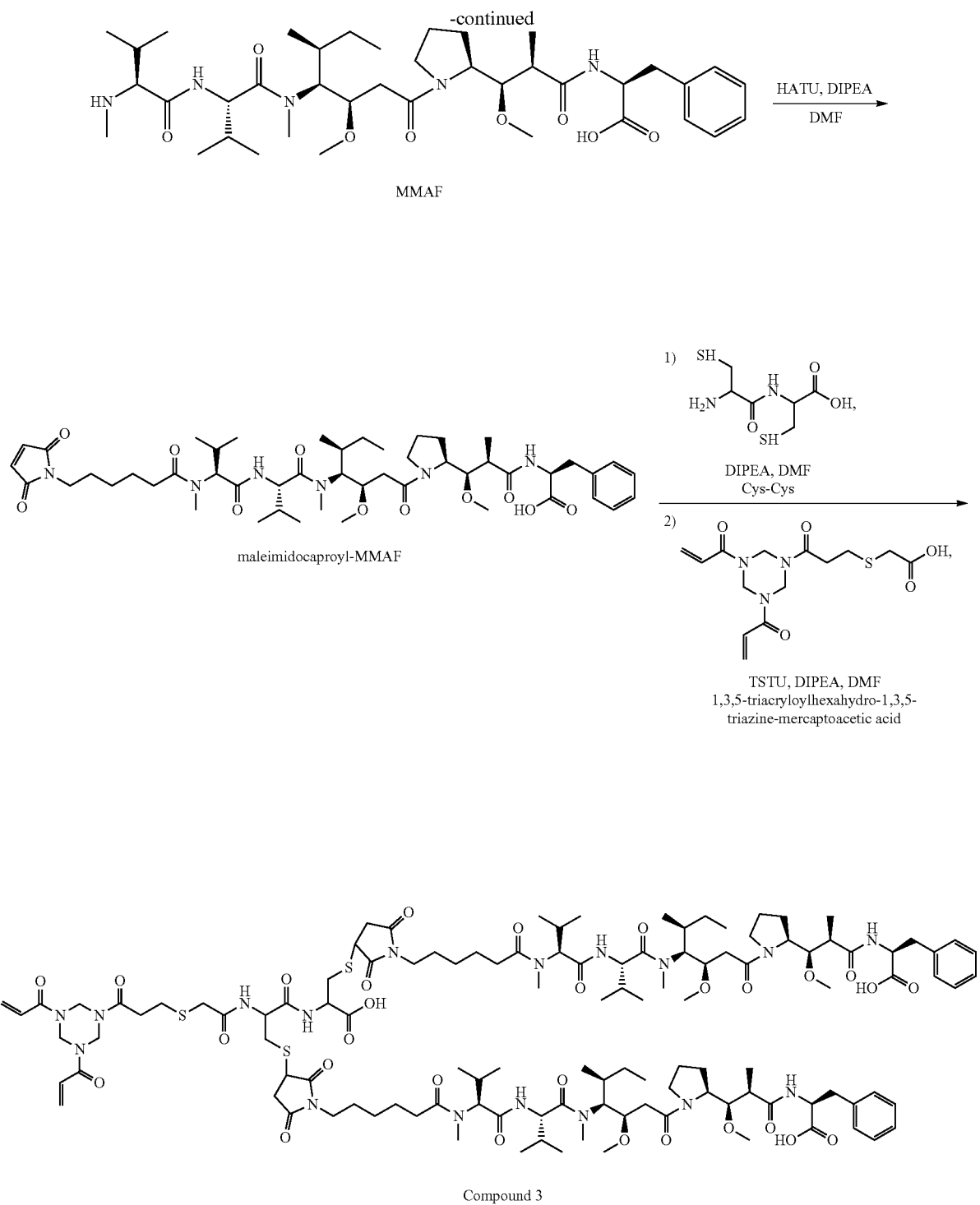

Maleimidocaproyl-MMAF was prepared in accordance with the method of Example 1. 31.6 mg of maleimidocaproyl-MMAF was dissolved in 2 mL of DMF, and then 3.9 mg of Cys-Cys and 2.9 μL of DIPEA were added, the mixture was stirred at room temperature for 4 h. 1.2 mg of Cys-Cys was added and the mixture was stirred at room temperature for 3 h. 0.8 mg of Cys-Cys was added, and the mixture was stirred at room temperature for 16 h. 12.1 mg of 1,3,5-triacryloylhexahydro-1,3,5-triazine-mercaptoacetic acid and 10.4 mg of TSTU were dissolved in 1.5 mL of DMF, and 17 μL of DIPEA was added, the mixture was stirred at room temperature for 2 h. Then the mixture was added to the above reaction system and stirred at room temperature for 5 h. The solvent was distilled off under reduced pressure, and purification was performed by preparative liquid chromatography to obtain 18.4 mg of Compound 3, with a yield of 29%. LC-MS: $(M+2H)^{2+}$ 1199.3, $(M-2H)^{2-}$ 1197.4.

Example 4. Preparation of Compound 4

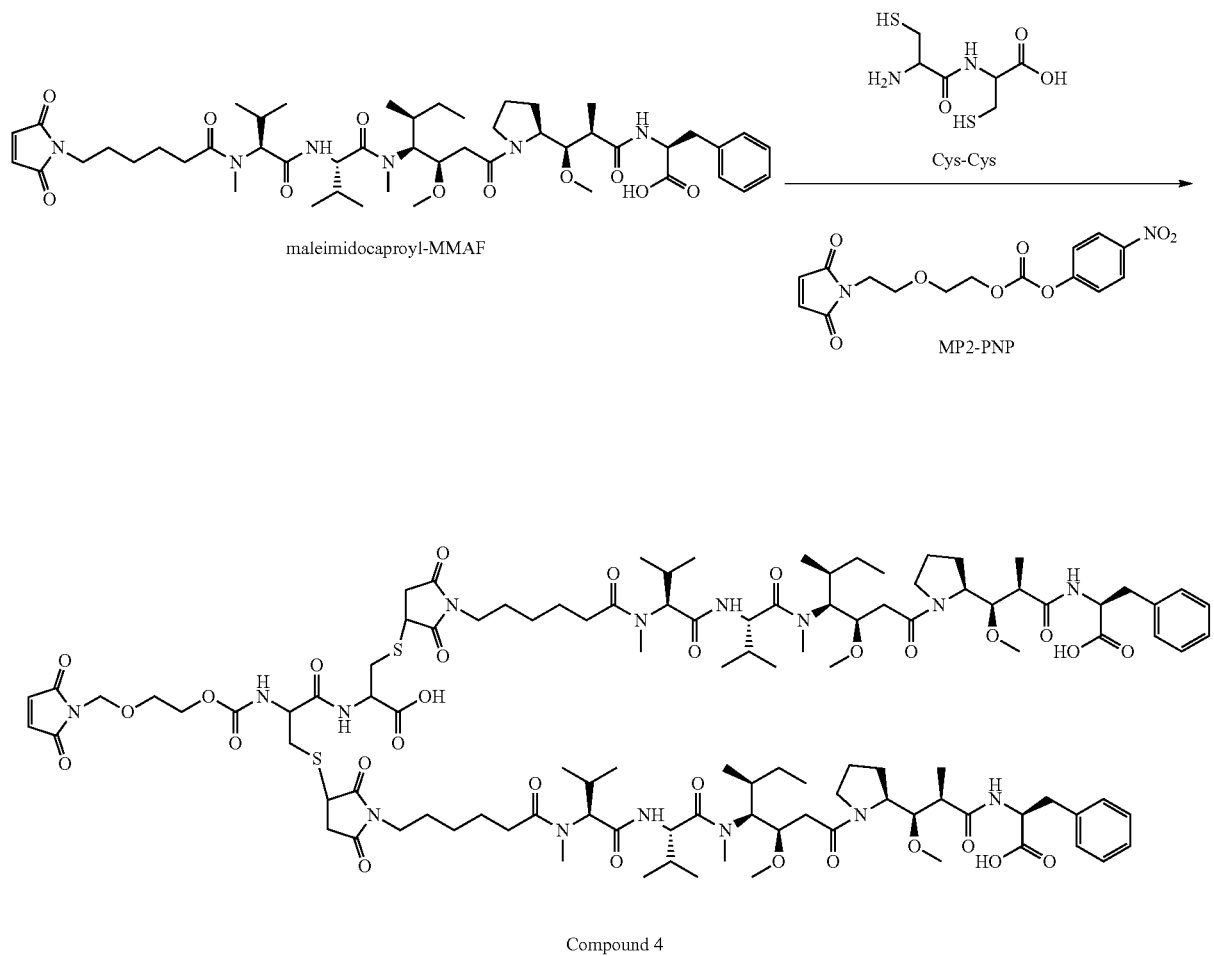

Compound 4

Maleimidocaproyl-MMAF was prepared in accordance with the method of Example 1. 55.0 mg of maleimidocaproyl-MMAF was dissolved in 1.5 mL of N,N-dimethylformamide, 11.6 mg of Cys-Cys and 4.3 µL of N,N-diisopropylethylamine were added and stirred at room temperature for 3 h. 36.1 mg of MP2-PNP (2-(2-Maleimidoethoxy)ethyl (4-nitrophenyl) carbonate) was added to the reaction system, then 51 µL N,N-diisopropylethylamine was added, and the mixture was stirred at room temperature for 15 h. The solvent was distilled off under reduced pressure, and purification was performed by preparative liquid chromatography to obtain 18.0 mg of Compound 4, with a yield of 27%. LC-MS: $(M+2H)^{2+}$ 1142.3, $(M-2H)^{2-}$ 1141.1.

Example 5. Preparation of Compound 5

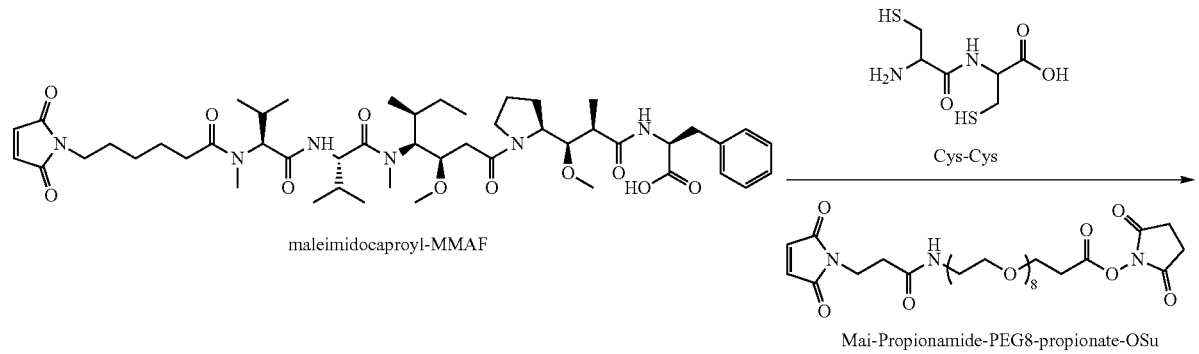

-continued

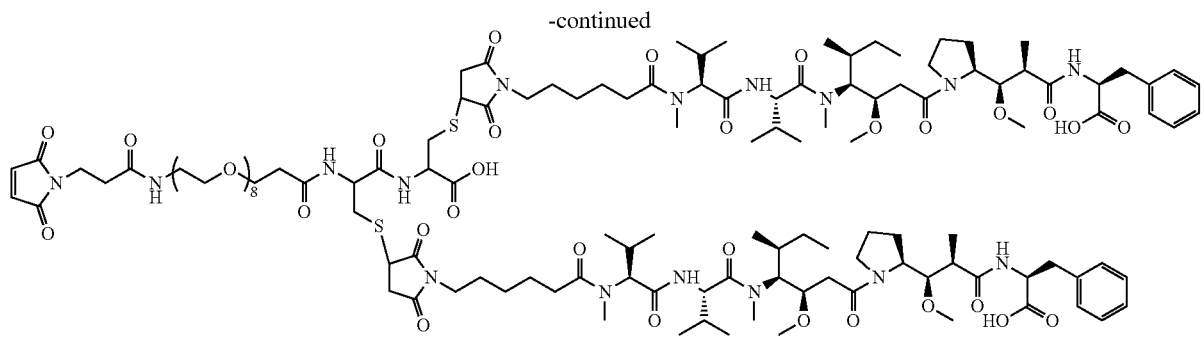

Compound 5

Maleimidocaproyl-MMAF was prepared according to the method of Example 1. 55.0 mg of maleimidocaproyl-MMAF was dissolved in 1.5 mL of N,N-dimethylformamide, 11.6 mg of Cys-Cys and 4.3 µL of N,N-diisopropylethylamine were added and stirred at room temperature for 3 h. 71.0 mg of Mal-Propionamide-PEG8-propionate-Osu was added to the reaction system, then 51 µL of N,N-diisopropylethylamine was added, and the mixture was stirred at room temperature for 15 h. The solvent was distilled off under reduced pressure, and purification was performed by preparative liquid chromatography to obtain 19.3 mg of Compound 5, with a yield of 28%, LC-MS: $(M+2H)^{2+}$ 1324.1, $(M-2H)^{2-}$ 1324.0.

Example 6. Preparation of Compound 6

91 92
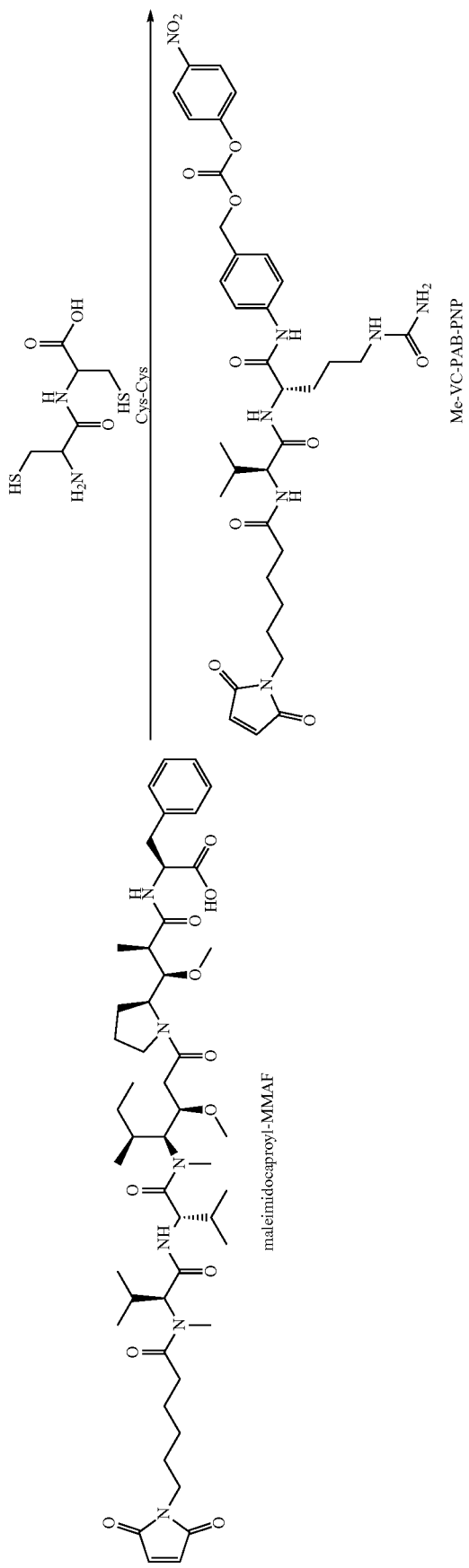
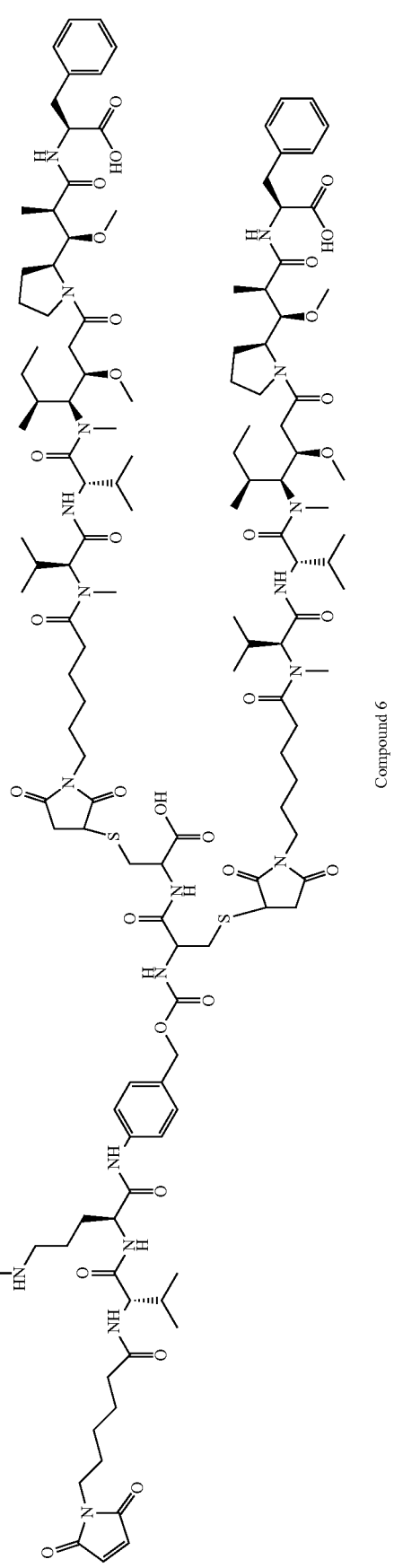

Maleimidocaproyl-MMAF was prepared in accordance with the method of Example 1. 63.0 mg of maleimidocaproyl-MMAF was dissolved in 2.0 mL of N,N-dimethylformamide, 13.3 mg of Cys-Cys and 4.8 µL of N,N-diisopropylethylamine were added, and the mixture was stirred at room temperature for 3 h. 86.6 mg of Mc-VC-PAB-PNP was added to the reaction system, and then 58 µL of N,N-diisopropylethylamine was added, and the mixture was stirred at room temperature for 15 h. The solvent was distilled off under reduced pressure, and purification was performed by preparative liquid chromatography to obtain 47.4 mg of Compound 6, with a yield of 52%, LC-MS: $(M+2H)^{2+}$ 1336.0, $(M-2H)^{2-}$ 1334.6.

Example 7. Preparation of Compound 7

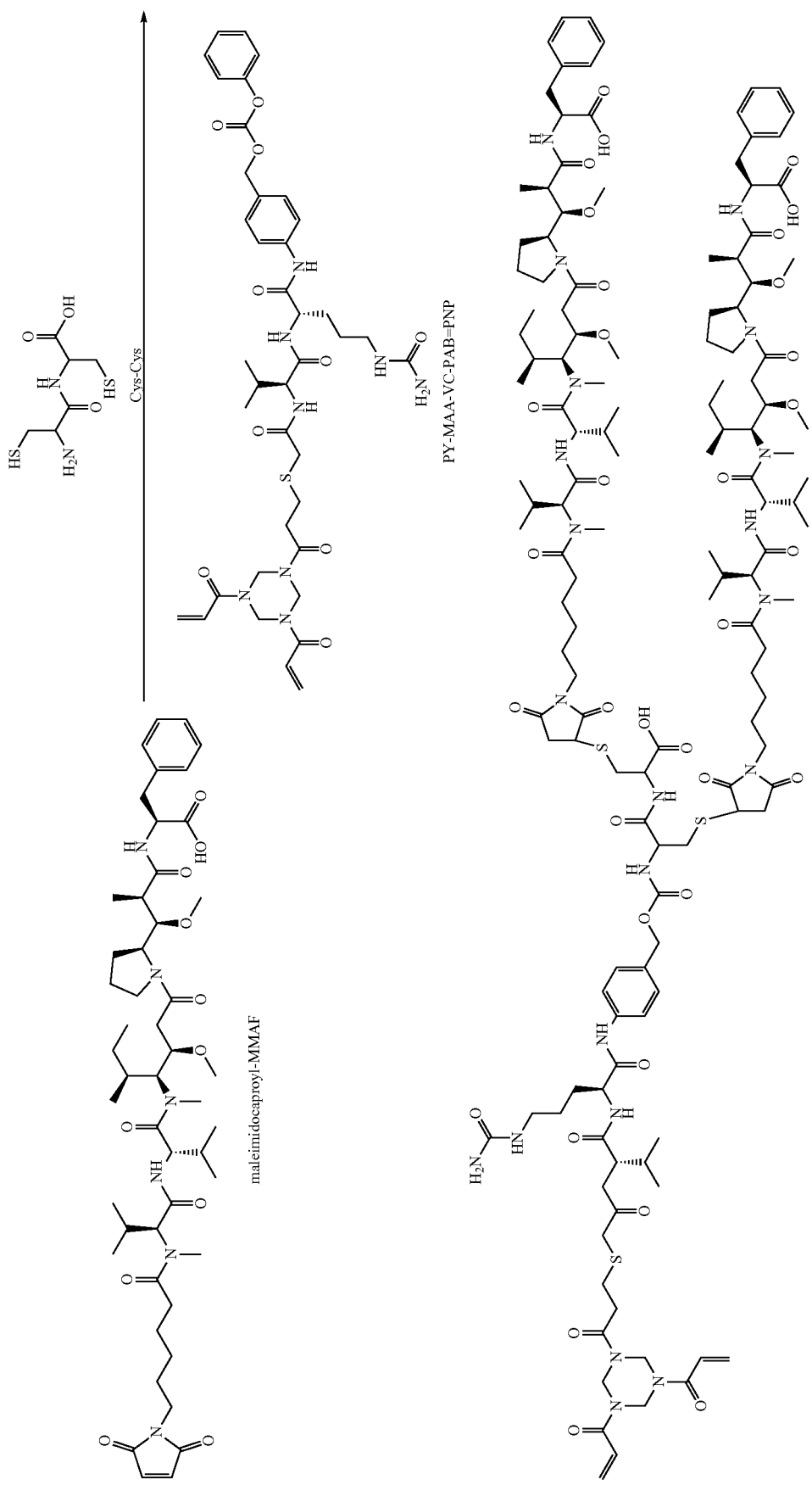

Maleimidocaproyl-MMAF was prepared in accordance with the method of Example 1. 46.6 mg of maleimidocaproyl-MMAF was dissolved in 2.0 mL of N,N-dimethylformamide, 10.9 mg of Cys-Cys and 3.6 μL of N,N-diisopropylethylamine were added, and the mixture was stirred at room temperature for 3 h. 84.4 mg of PY-MAA-VC-PAB-PNP was added to the reaction system, and then 48 μL of N,N-diisopropylethylamine was added, and the mixture was stirred at room temperature for 15 h. The solvent was distilled off under reduced pressure, and purification was performed by preparative liquid chromatography to obtain 31.0 mg of Compound 7 of, with a yield of 43%, LC-MS: $(M+2H)^{2+}$ 1401.2, $(M-2H)^{2-}$ 1399.4.

Example 8. Preparation of Antibody-Drug Conjugates (ADCs)

General methods for synthesizing the antibody-drug conjugates are as follows.

Method A: Anti-Her-2 antibody was diluted to a 10 mg/mL solution using PBS buffer (pH=7.4), 2.4 molar equivalents of TCEP was added, and the mixture was mixed with shaking for 1 hour. 5.0 molar equivalents of linker-drug was added, and the mixture was mixed with shaking and reacted for 1 h. After the completion of the reaction, the remaining small molecules were removed by ultrafiltration. The resultant was loaded into hydrophobic chromatography (HIC-HPLC) for DAR, drug distribution and naked antibody percentage analysis.

Method B: Anti-Her-2 antibody was diluted to a 10 mg/mL solution using boric acid-borax buffer (pH=9), 5 molar equivalents of TCEP was added, and the mixture was mixed with shaking for 1 hour. 6.0 molar equivalents of linker-drug was added, and the mixture was mixed with shaking and reacted for 3 h. After the completion of the reaction, the remaining small molecules were removed by ultrafiltration. The resultant was loaded into hydrophobic chromatography (HIC-HPLC) for DAR, drug distribution and naked antibody percentage analysis.

The following compounds were prepared by the above general ADC preparation methods (A is an antibody or a functional binding fragment thereof, m is 1, 2, 3, 4, 5, 6, 7 or 8).

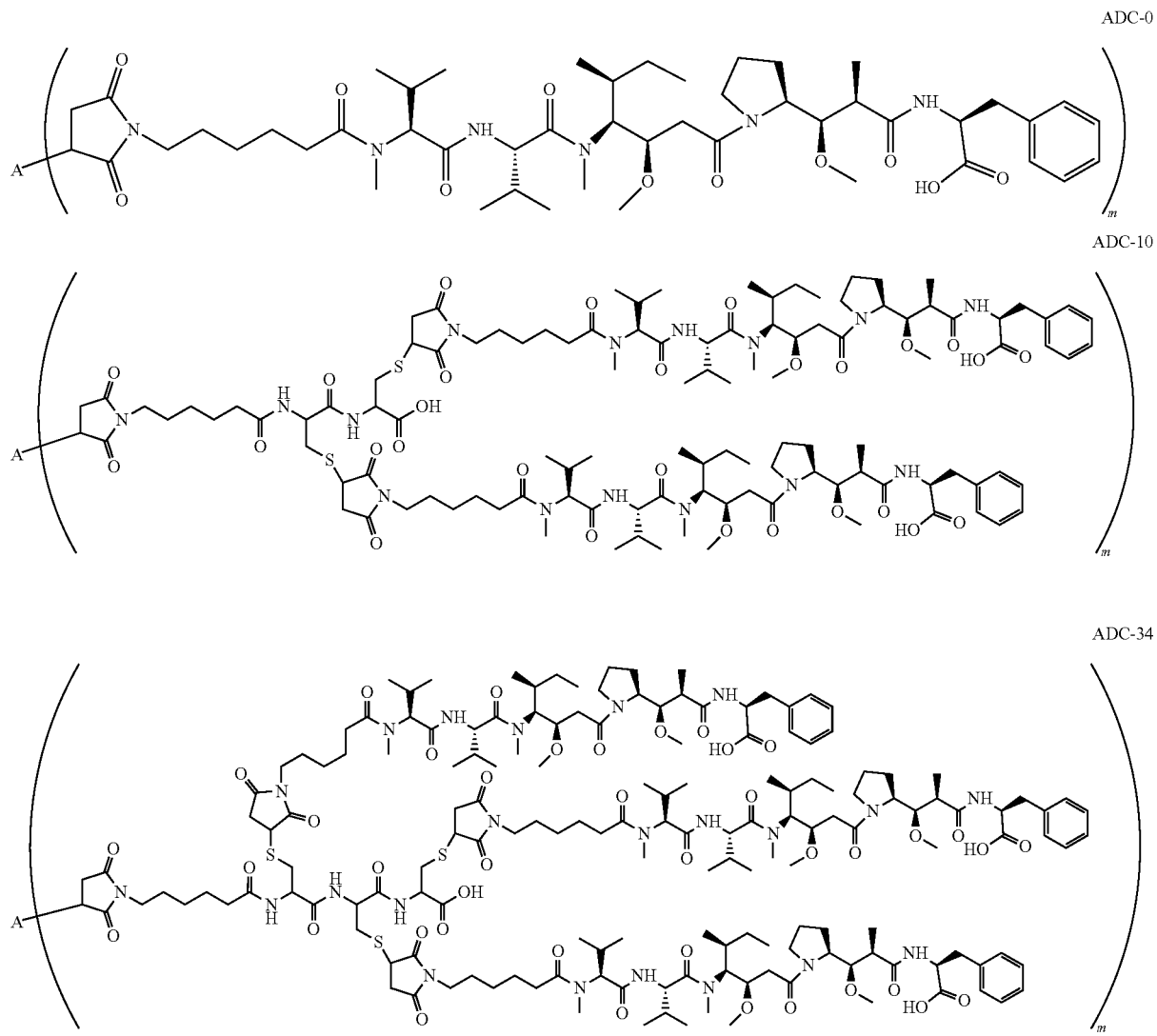

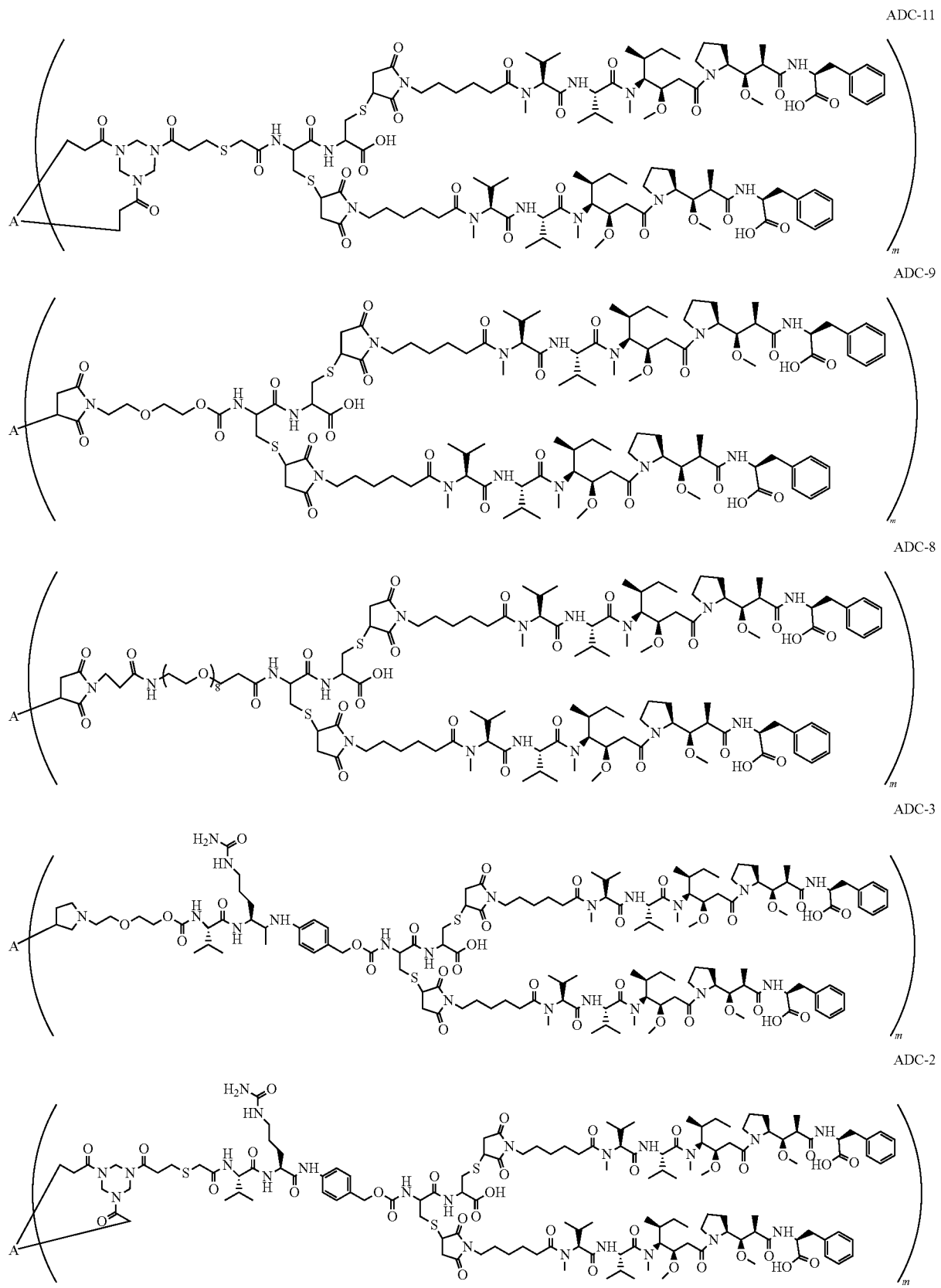

Example 9. Inhibition of ADCs on Tumor Cell Line SK-BR-3

SK-BR-3 tumor cells (human breast cancer cells) were digested and collected by centrifugation. The cells were counted and diluted to a cell suspension of $0.5\text{-}1.5 \times 10^5$ cells/mL. 100 μL cell suspension was added to each well of a 96-well plate. The plate was incubated overnight in an incubator at 37° C. with 5% $CO_2$. In the next day, ADCs with 9 corresponding concentration gradients were added, cells without ADC treatment were used as a control group. After 72 hours of culture, the Cell Counting Kit-8 (CCK-8 kit for short) was used for activity assay, and the 96-well plate after color development was used for the reading of OD value at 450 nm by a microplate reader. The Prism software was used to calculate the $IC_{50}$ based on the OD values. When the fitted curve shows an "S-curve" and $R^2 \geq 0.95$, the $IC_{50}$ value is valid and reported.

We selected ADC-0 with a DAR value of 3.87 (Comparative Example 1), ADC-0 with a DAR value of 7.18 (Comparative Example 2), ADC-10 with a DAR value of 4.3 (Comparative Example 3), and ADC-34 with a DAR value of 4.29 (Comparative Example 4) for the inhibition experiments performed on tumor cell line SK-BR-3. $IC_{50}$ values thereof are shown in Table 2.

TABLE 2

Evaluation of the inhibition experiments on tumor cell line SK-BR-3

| ADC | DAR | $IC_{50}$ ($10^{-3}$ nmol/L) | | | | $R^2$ | Maximum rate of inhibition (%) |
|---|---|---|---|---|---|---|---|
| | | ADC | ADC dosage change* | MMAF | MMAF dosage change* | | |
| Comparative Example 1 | ADC-0 | 3.87 | 5.52 | 0 | 21.3624 | 0 | 0.999 | 89.93 |
| Comparative Example 2 | ADC-0 | 7.18 | 3.55 | −35.7% | 25.489 | 19.3% | 0.996 | 83.78 |
| Comparative Example 3 | ADC-10 | 4.3 | 1.88 | −65.9% | 16.168 | −24.3% | 0.997 | 91.55 |
| Comparative Example 4 | ADC-34 | 4.29 | 0.8 | −85.5% | 10.296 | −51.8% | 1.000 | 88.09 |

*using Comparative Example 1 as a base, antibody dosage change = (Comparative Example X-Comparative Example 1)/Comparative Example 1; X represents the corresponding comparative example;
**using Comparative Example 1 as a base, MMAF dosage change = (Comparative Example X-Comparative Example 1)/Comparative Example 1; X represents the corresponding comparative example.

In Comparative Example 2, DAR value was increased to 7.18 by increasing the number of MMAF sites linked to the antibody. Compared with Comparative Example 1, when the same effect was achieved, Comparative Example 2 can effectively reduce the usage of antibody (i.e., the amount of antibody in the ADC, and if antibody loss in the synthesis process is not considered, the antibody usage is equal to the concentration of the ADC), whereas the MMAF usage is increased by 19.3%.

In Comparative Example 3, two MMAF were linked to one linker, and DAR value (4.3) was comparable to Comparative Example 1 (3.87). Compared with Comparative Example 1, when the same effect was achieved, Comparative Example 3 effectively reduced the antibody usage by 65.9%, and the MMAF usage by 24.3%.

In Comparative Example 4, three MMAF were linked to one linker, and the DAR value was comparable to that of Comparative Example 1. Compared with Comparative Example 1, Comparative Example 4 effectively reduced the antibody usage by 85.5%, and the MMAF usage by 51.8%.

From the above comparison data, ADC-10 and ADC-34 show higher activity to cells. The effect is not only due to the improved effect of ADC by increasing the number of MMAF in the antibody. It also demonstrates that, in the case of carrying the same number of MMAF, by linking multiple cytotoxic drugs to a single site, the used amount of antibody and the used amount of drugs are greatly reduced, giving an unexpected technical effect. And through the way of single connection site with multiple drugs, it can also effectively improve the uniformity of the ADC products, and promote the drug production and quality control process.

The present disclosure has been illustrated by way of specific examples. However, those skilled in the art can understand that the present disclosure is not limited to the specific examples, and various modifications and changes may be made by those of ordinary skill in the art within the scope of the present disclosure, and various technical features mentioned throughout the specification may be combined with one another without departing from the spirit and scope of the present disclosure. Such modifications and variations are within the scope of the present disclosure.

The invention claimed is:

1. An antibody-drug conjugate represented by formula (II) to formula (IV):

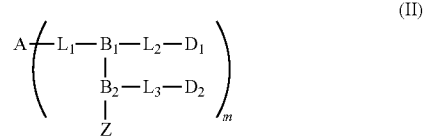

(II)

or

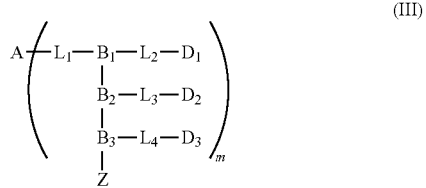

(III)

or

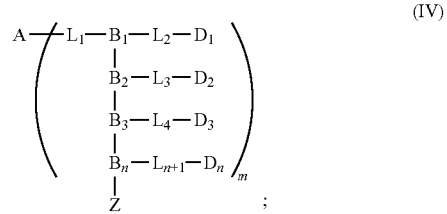

(IV)

;

wherein,

A is an antibody or a functional binding fragment thereof;

$B_1, B_2, B_3, \ldots$, and $B_n$ are respectively represented by formula (V):

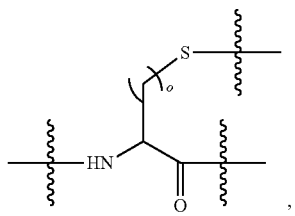

(V)

wherein p is selected from the group consisting of 1, 2, 3, 4, 5, 6, 7 and 8;

$L_1, L_2, L_3, L_4, \ldots$, and $L_{n+1}$ are each independently a linker, which may be the same or different;

$L_1$ is covalently linked to the amino terminus of $B_1$, $L_2$ and $B_1$, $L_3$ and $B_2$, $L_4$ and $B_3$, $\ldots$, $L_{n+1}$ and $B_n$ are covalently linked via a thiol group, and $L_2$ and $D_1$, $L_3$ and $D_2$, $L_4$ and $D_3$, $\ldots$, $L_{n+1}$ and $D_n$ are covalently linked;

$D_1, D_2, D_3, \ldots$, and $D_n$ are each independently an active drug, which may be the same or different;

Z is a group covalently linked to the carbonyl group of $B_1$ in formula (I), the carbonyl group of $B_2$ in formula (II), the carbonyl group of $B_3$ in formula (III) or the carbonyl group of $B_n$ in formula (IV);

n is an integer greater than or equal to 4, which represents the number of branches linking to the active drugs; and m is selected from the group consisting of 1, 2, 3, 4, 5, 6, 7 and 8;

wherein $L_2, L_3, L_4, \ldots$, and $L_{n+1}$ are selected from the group consisting of:

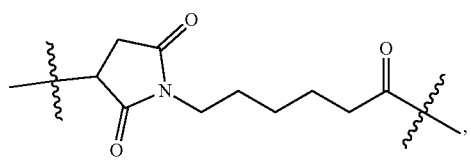

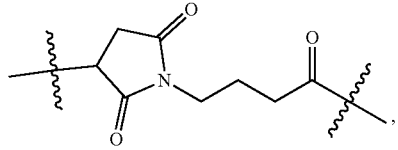

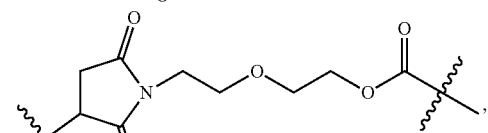

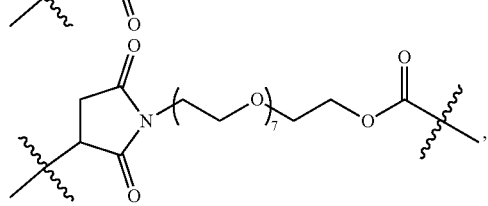

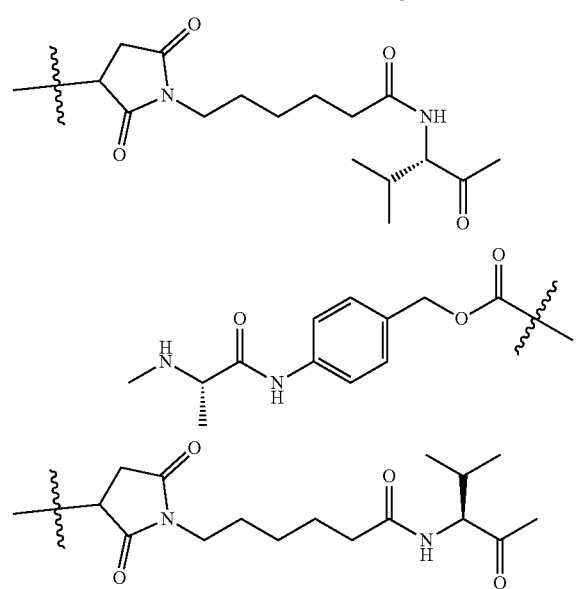

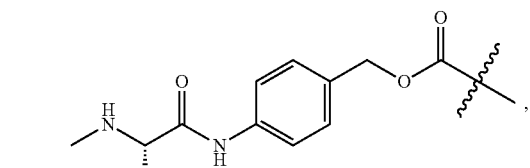

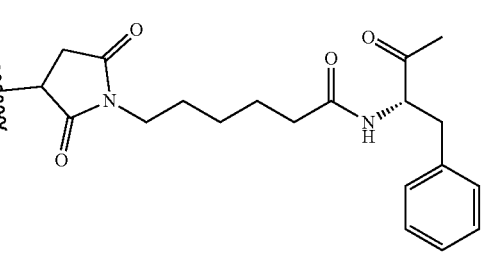

105
-continued
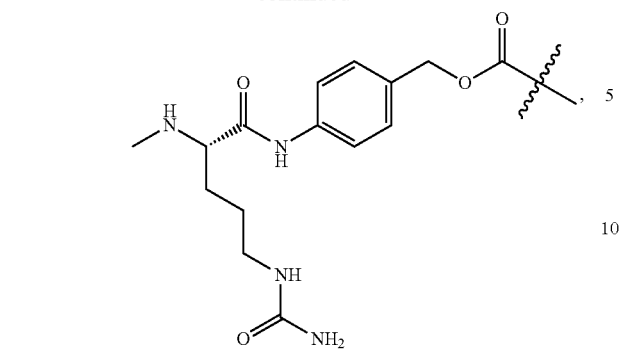
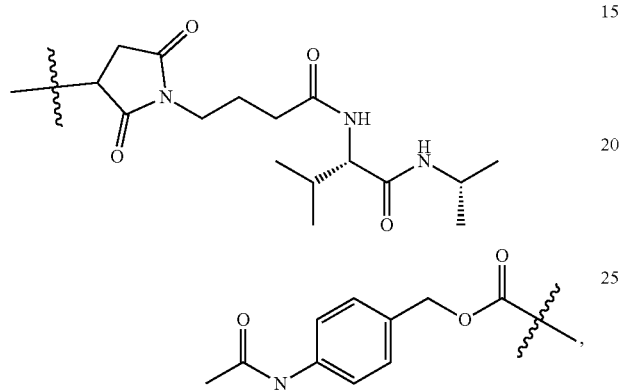
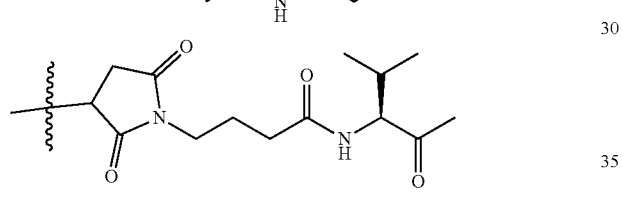
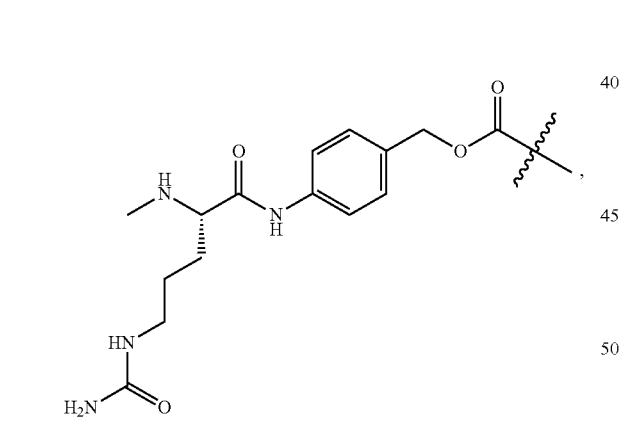
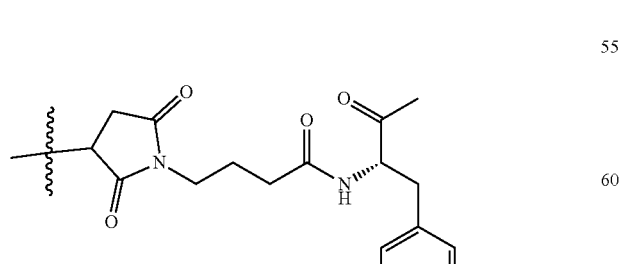
106
-continued
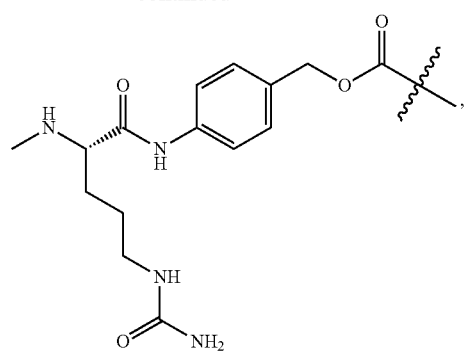
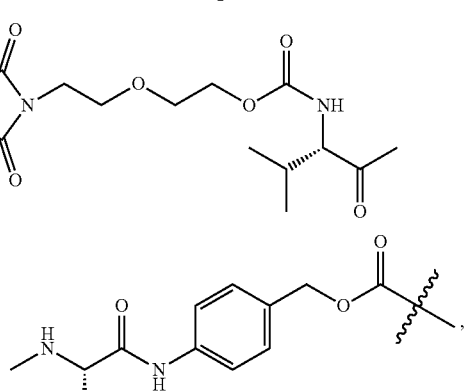
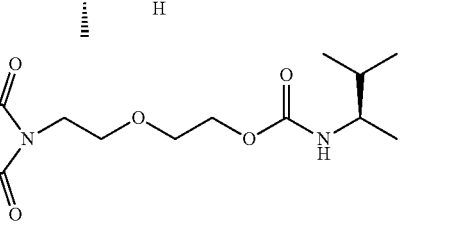
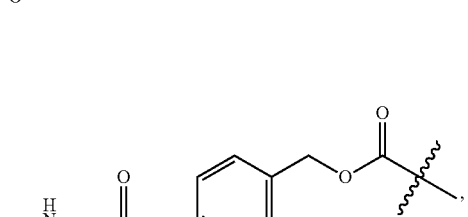
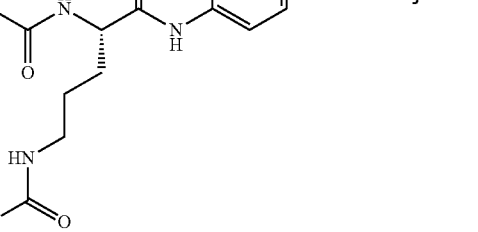
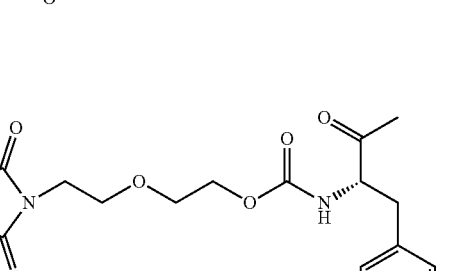

107
-continued
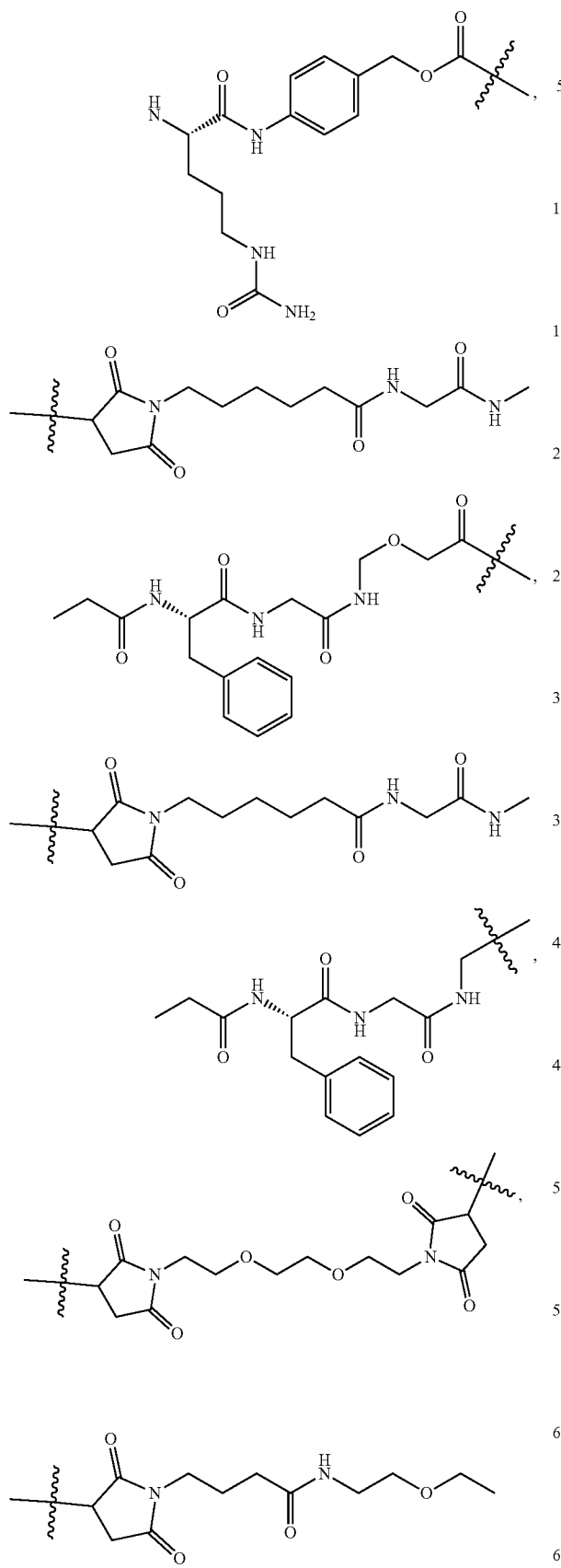
108
-continued
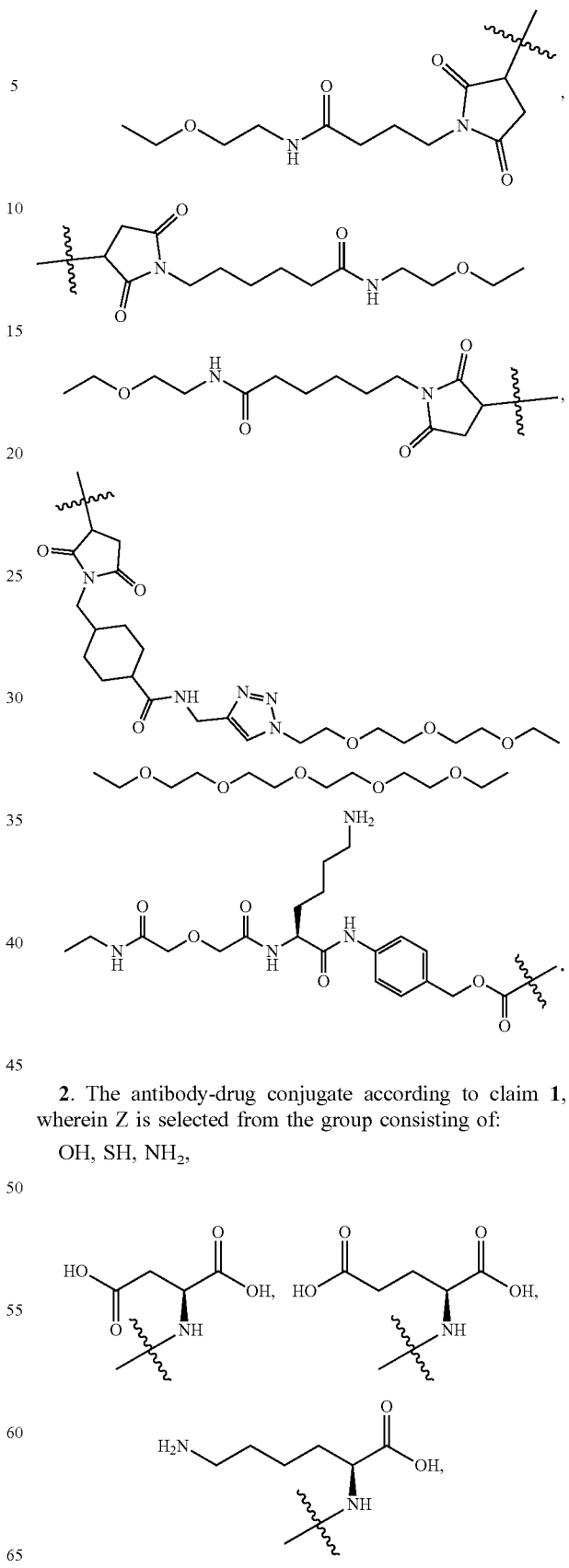
2. The antibody-drug conjugate according to claim 1, wherein Z is selected from the group consisting of:
OH, SH, NH₂,
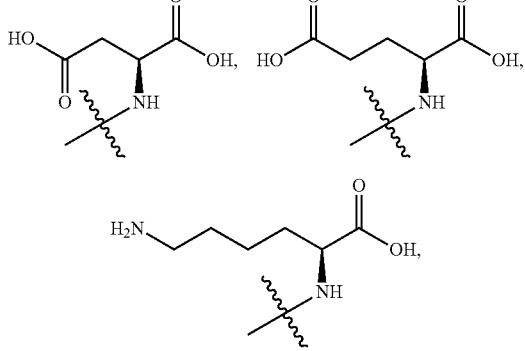

-continued

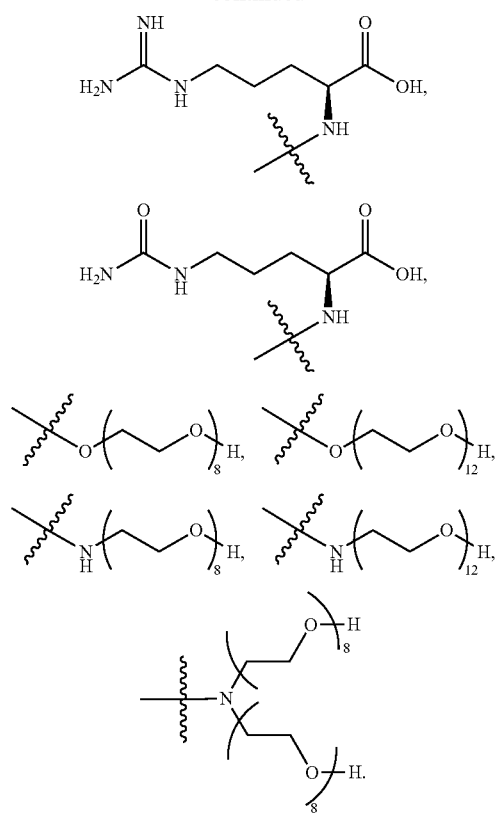

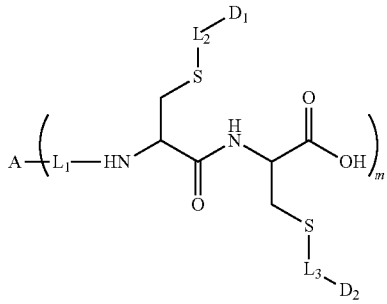

(VI-3)

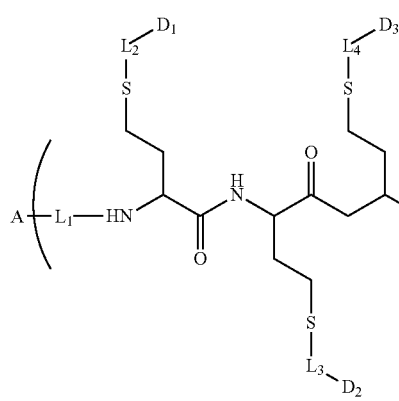

(VI-4)

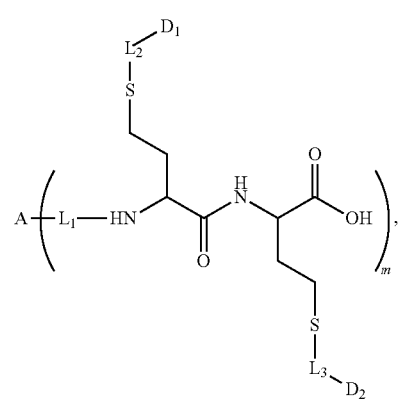

(VI-5)

3. The antibody-drug conjugate according to claim 1, which has a structure represented by formula (VI-1) to (VI-5):

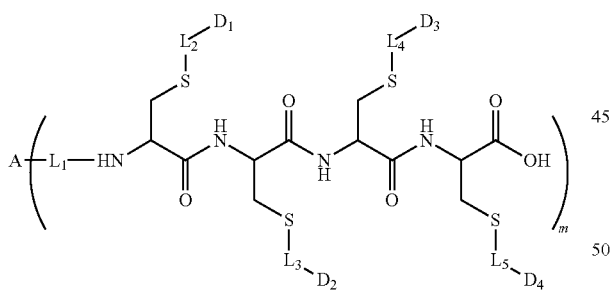

(VI-1)

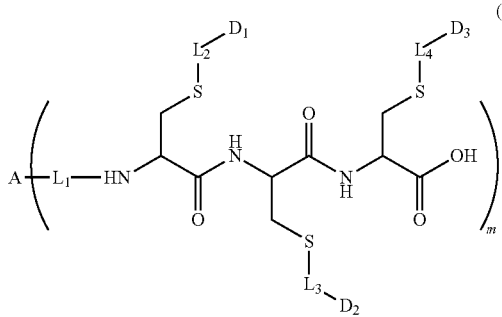

(VI-2)

wherein
A is an antibody or a functional binding fragment thereof;
$L_1$, $L_2$, $L_3$, $L_4$ and $L_5$ are each independently a linker, which may be the same or different;
$D_1$, $D_2$, $D_3$ and $D_4$ are each independently an active drug, which may be the same or different; and
m is selected from the group consisting of 1, 2, 3, 4, 5, 6, 7 and 8.

4. The antibody-drug conjugate according to claim 1, wherein $L_1$ is covalently linked to an amino residue or a thiol residue of the antibody.

5. The antibody-drug conjugate according to claim 1, wherein $L_1$, $L_2$, $L_3$, $L_4$, ..., and $L_{n+1}$ are a cleavable linker or a combination of cleavable linkers.

6. The antibody-drug conjugate according to claim 5, wherein the cleavable linker comprises a peptide linker and a polysulfide bond, and wherein
the peptide linker comprises 2 to 20 amino acids; and
the polysulfide bond contains 2 to 8 sulfur atoms.

7. The antibody-drug conjugate according to claim 1, wherein $L_1$ is selected from the group consisting of:

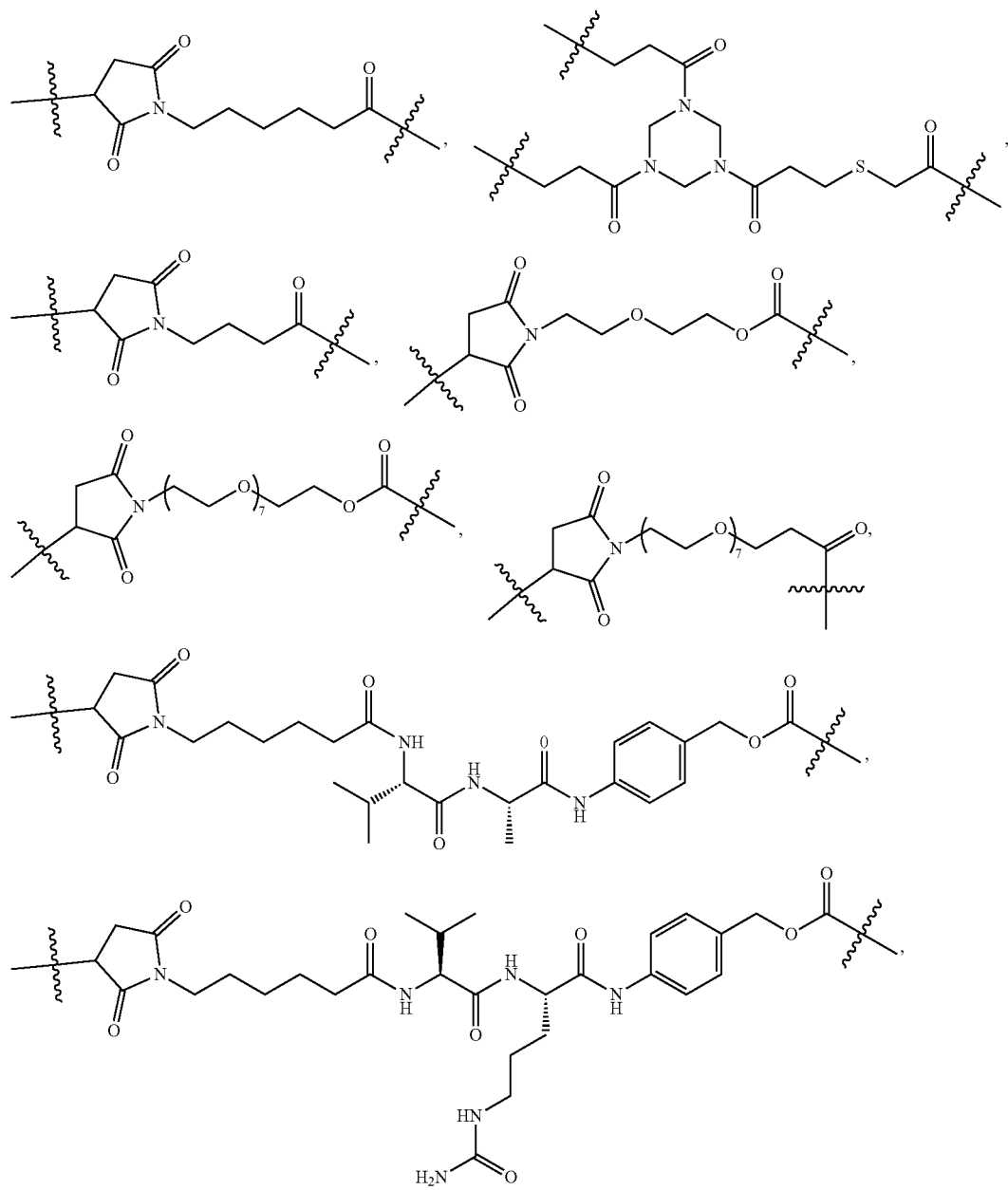
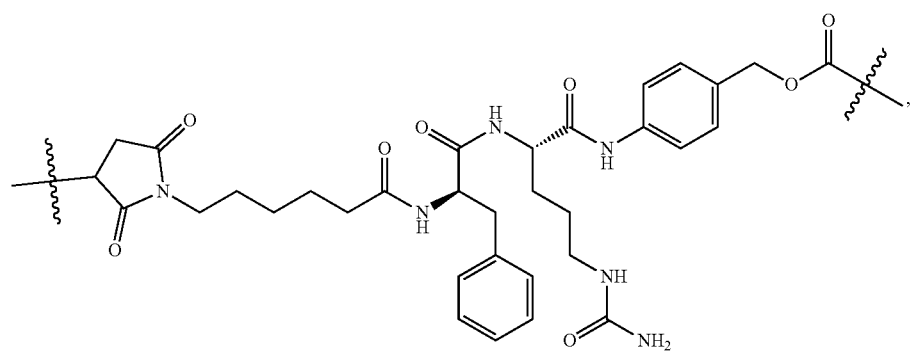

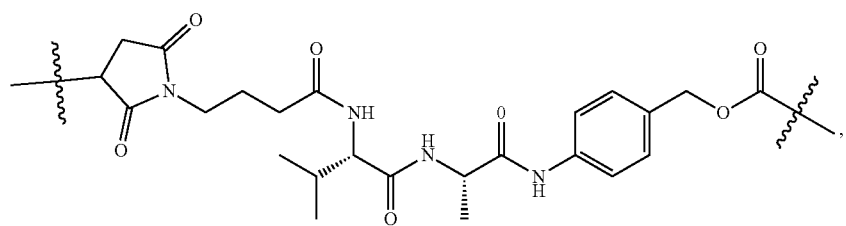
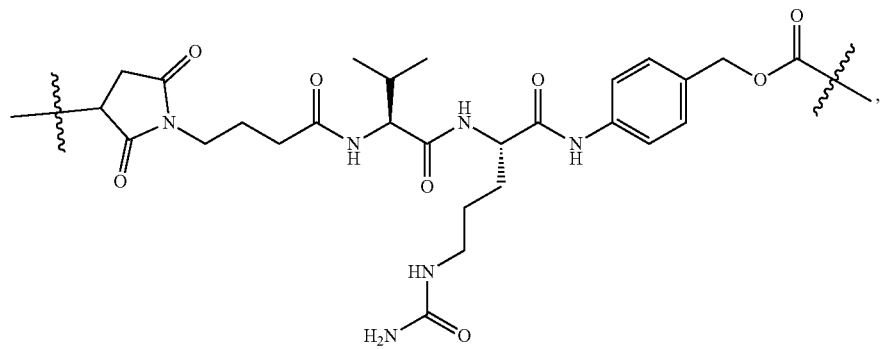
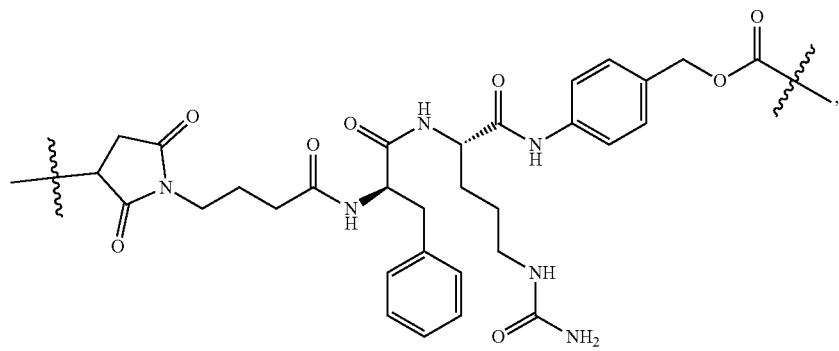
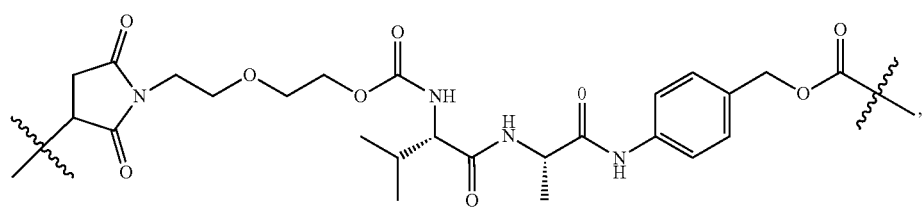
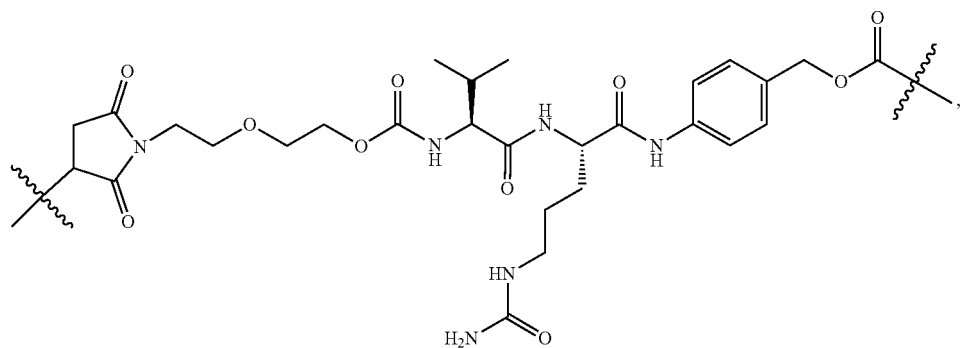

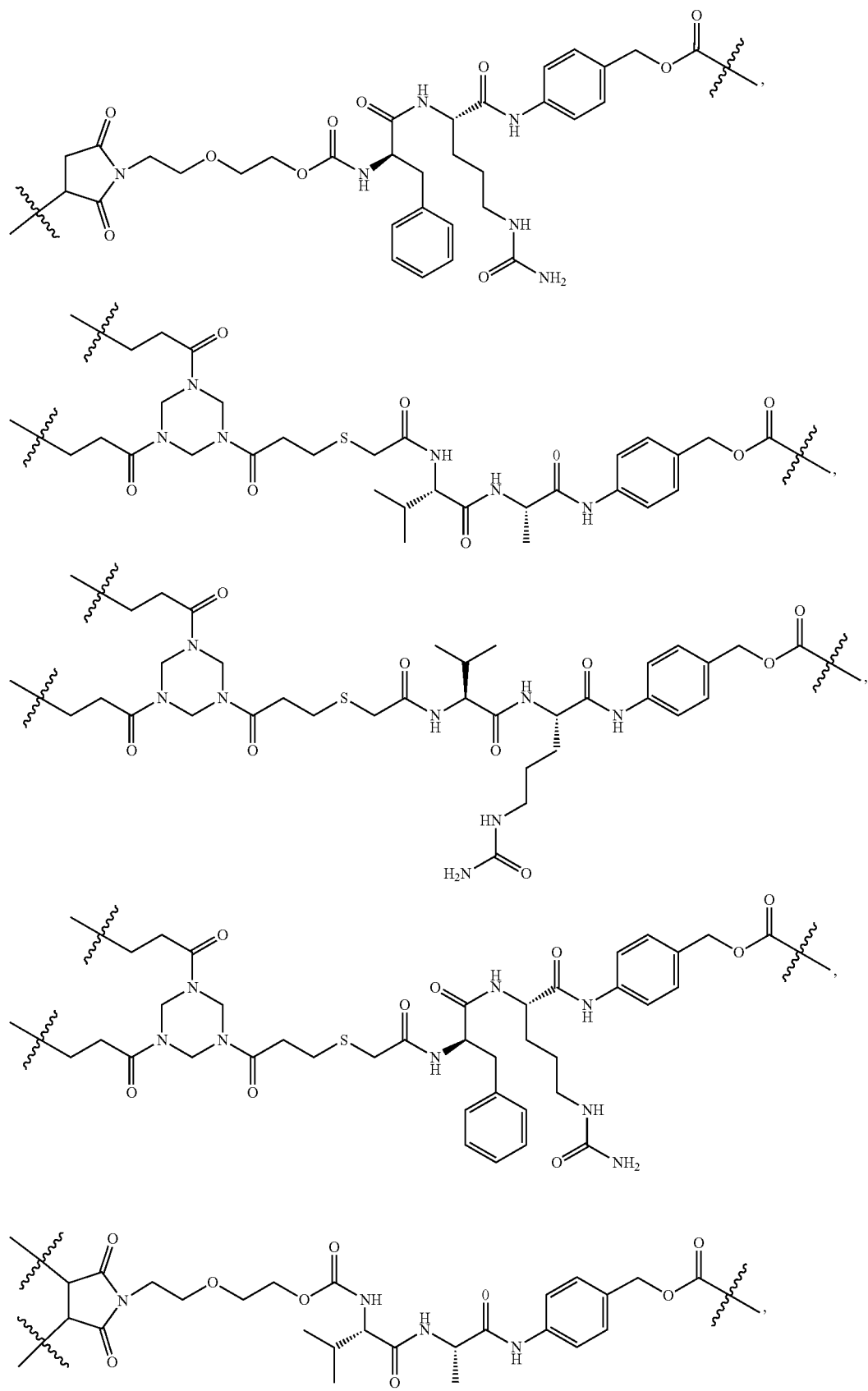

-continued
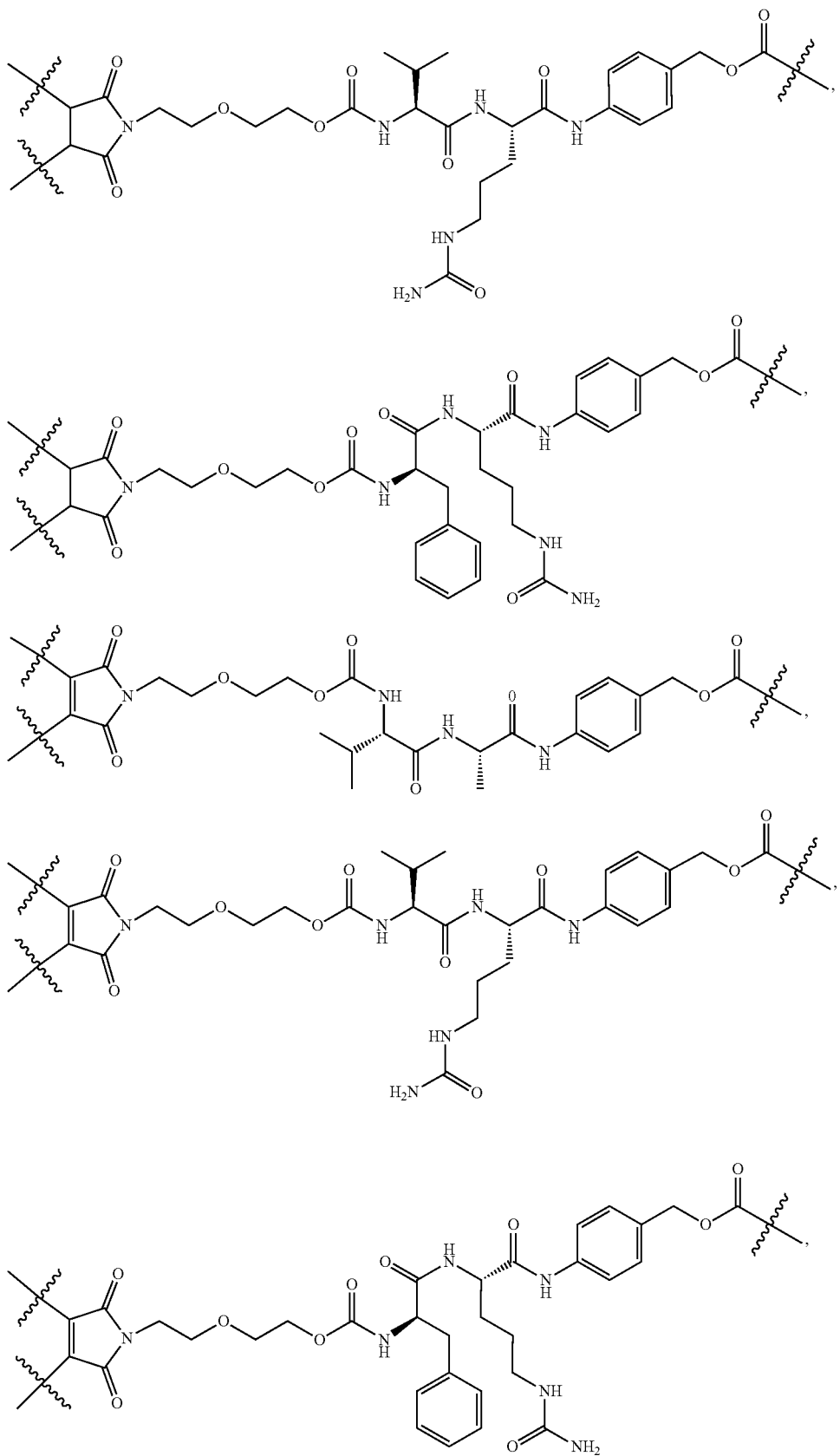

-continued
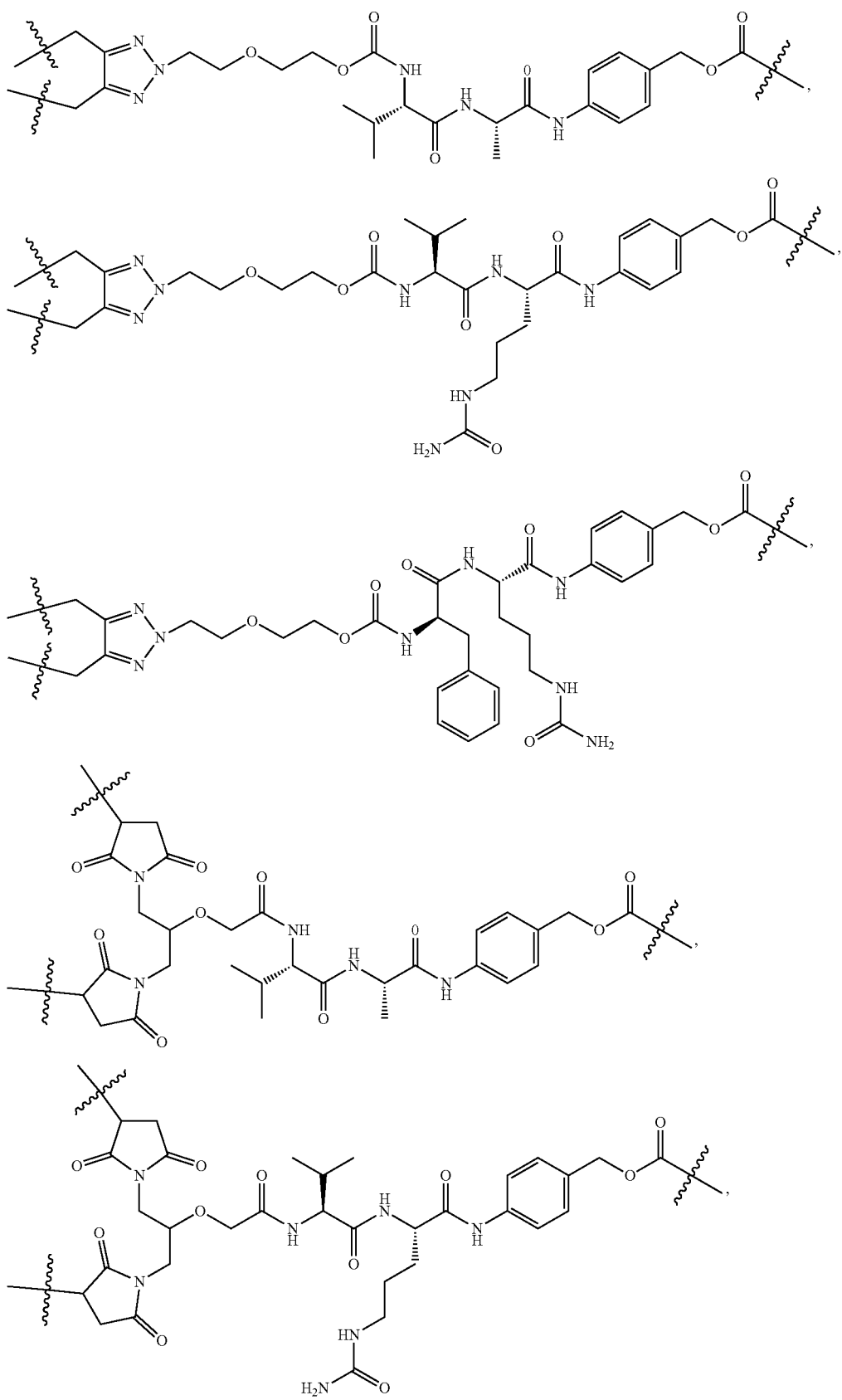

-continued
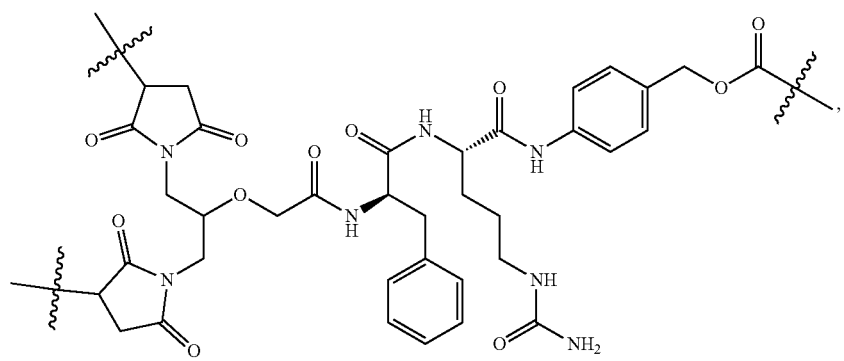
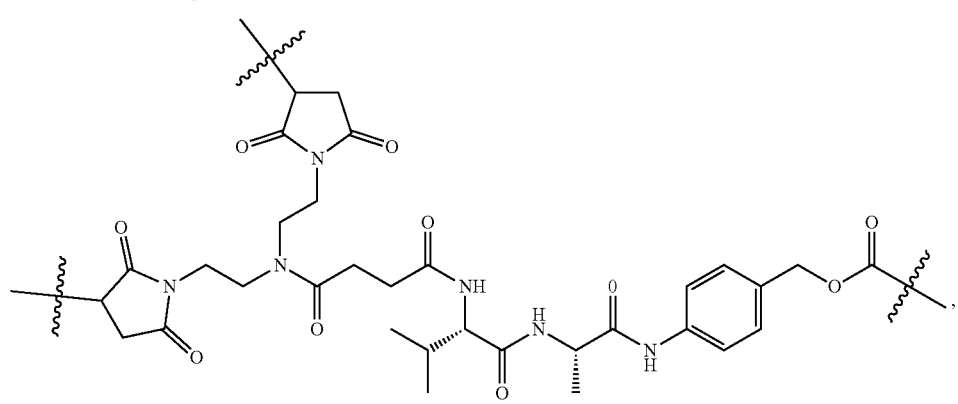
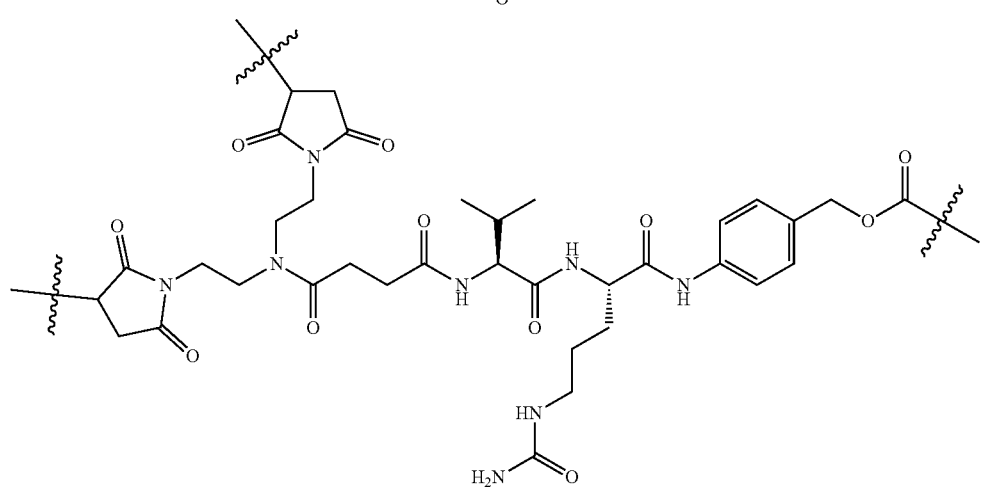 and
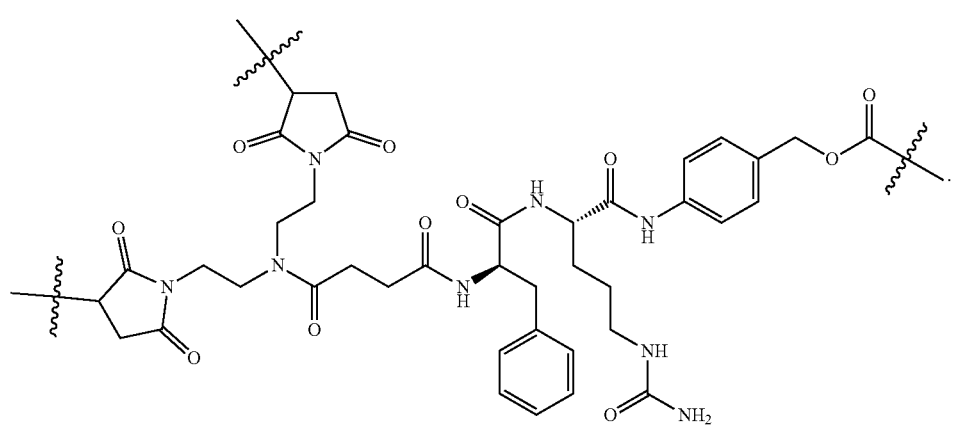 [SMILES: *C(=O)OCc1ccc(NC(=O)[C@H](CCCNC(N)=O)NC(=O)[C@@H](Cc2ccccc2)NC(=O)CCC(=O)N(CCN2C(=O)CC(*)C2=O)CCN2C(=O)CC(*)C2=O)cc1]

8. The antibody-drug conjugate according to claim 1, wherein the antibody or functional binding fragment thereof is selected from the group consisting of a monoclonal antibody, a polyclonal antibody, an antibody fragment, Fab, Fab', Fab'-SH, F(ab')$_2$, Fv, single chain Fv ("scFv"), a diabody, a linear antibody, a bispecific antibody, a multi-specific antibody, a chimeric antibody, a humanized antibody, a fully human antibody, and a fusion protein containing an antigen-binding fragment of antibody.

9. The antibody-drug conjugate according to claim 8, wherein the antibody is an IgG antibody or a functional binding fragment thereof.

10. The antibody-drug conjugate according to claim 1, wherein the active drug is selected from the group consisting of a cytotoxic molecule, a cell differentiation factor, a stem cell trophic factor, a steroids drug, a drug for treating an autoimmune disease, an anti-inflammatory drug and a drug for treating an infectious disease.

11. The antibody-drug conjugate according to claim 10, wherein the cytotoxic molecule is selected from the group consisting of a tubulin inhibitor and a DNA damaging agent.

12. The antibody-drug conjugate according to claim 1, which has a structure represented as follows:

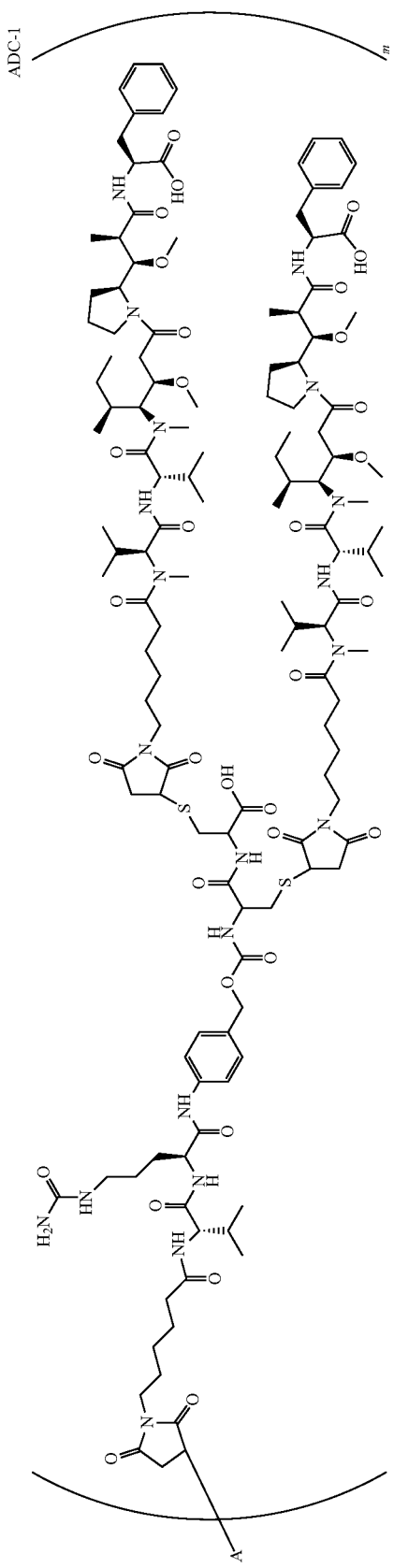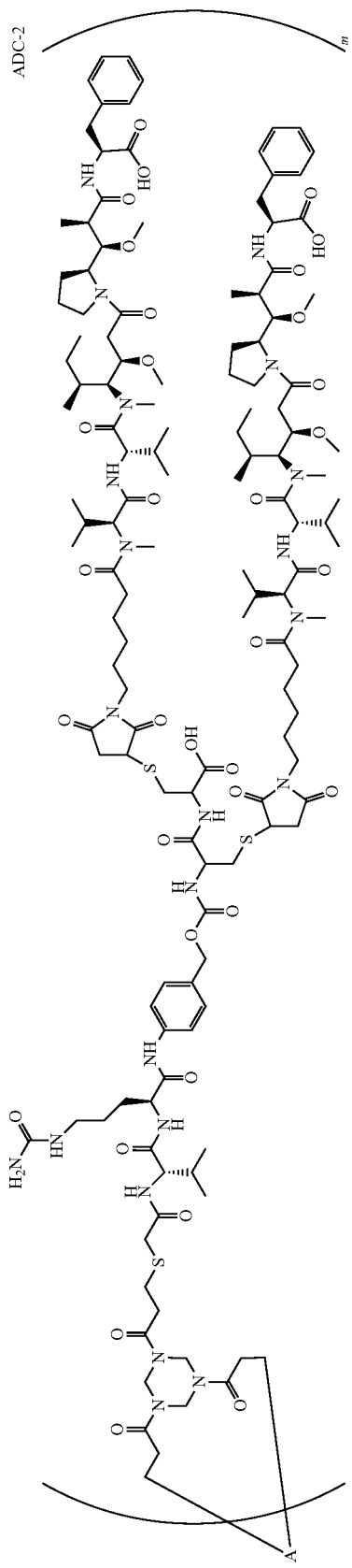

-continued
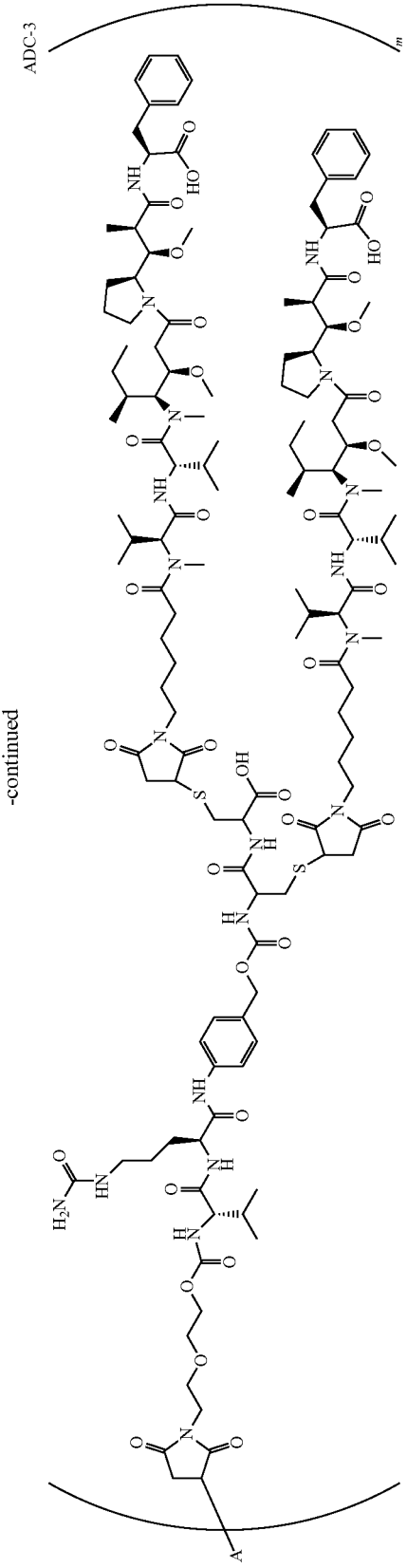
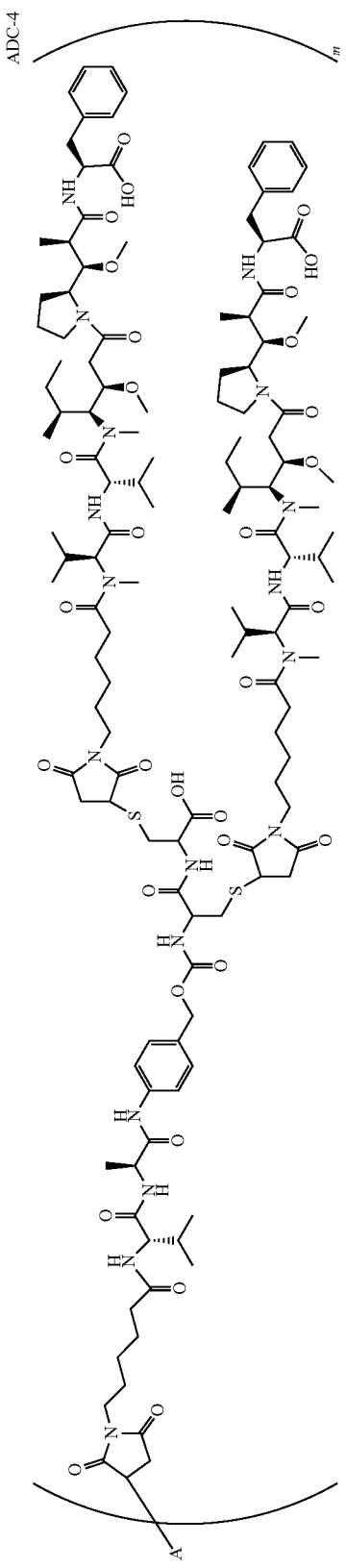

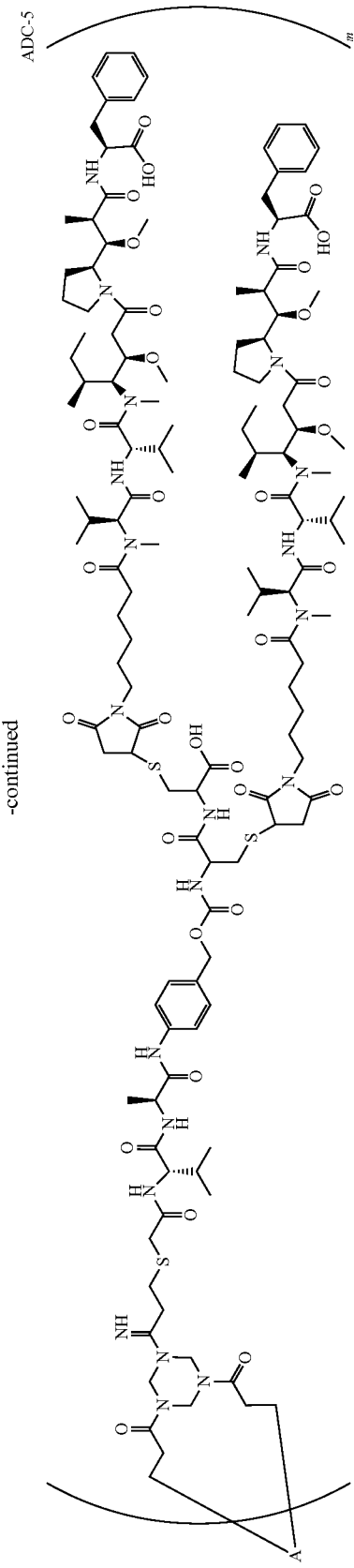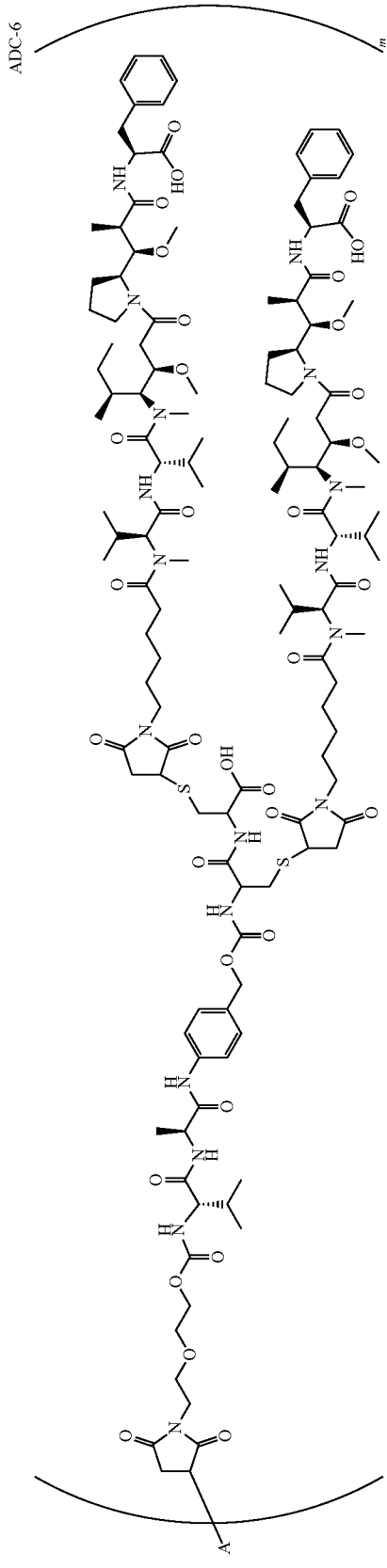

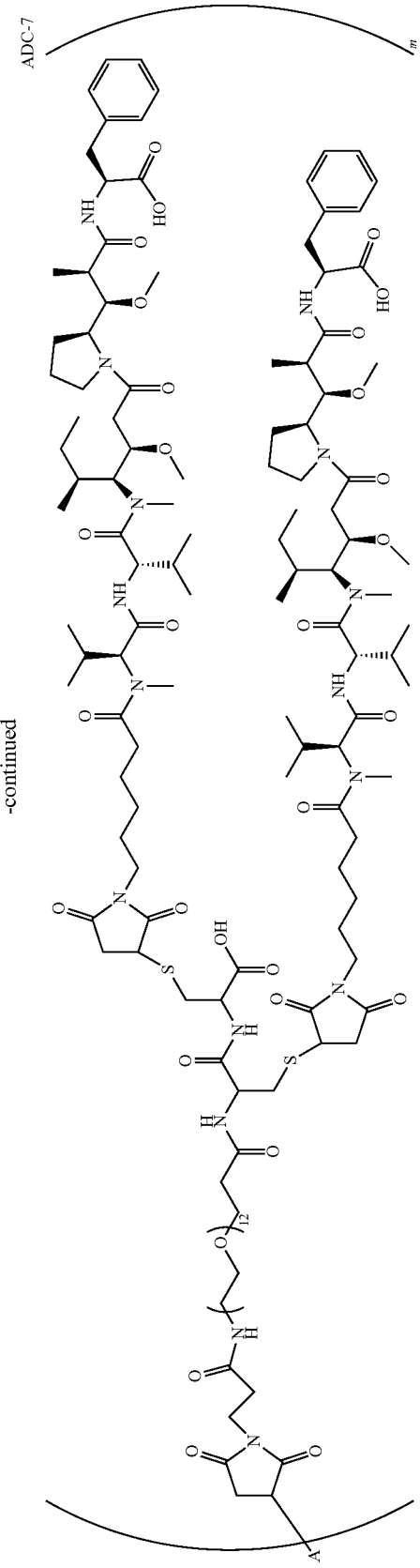

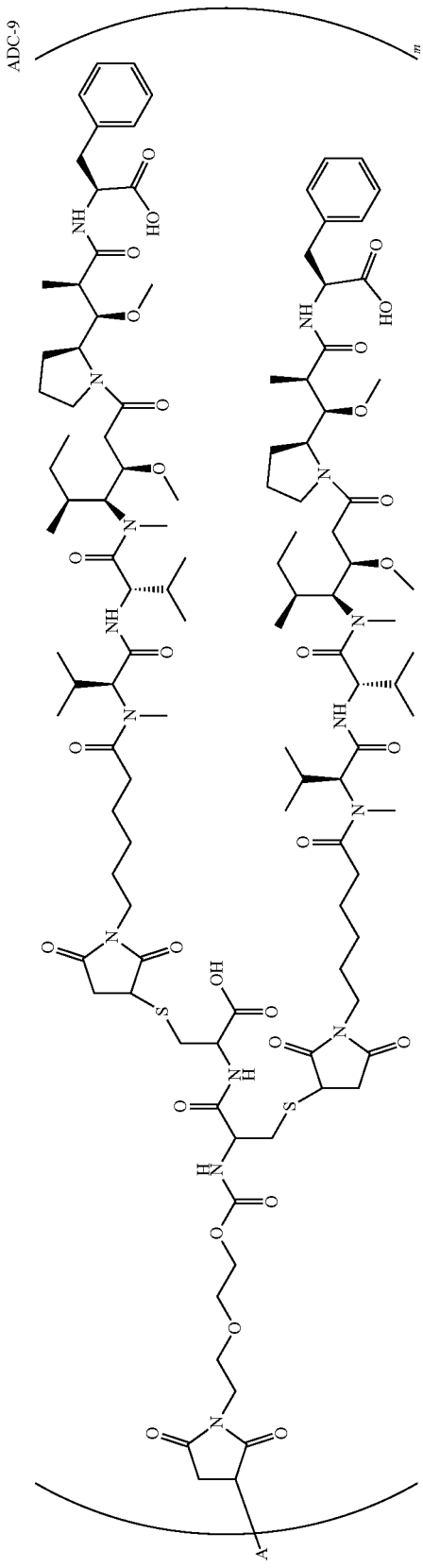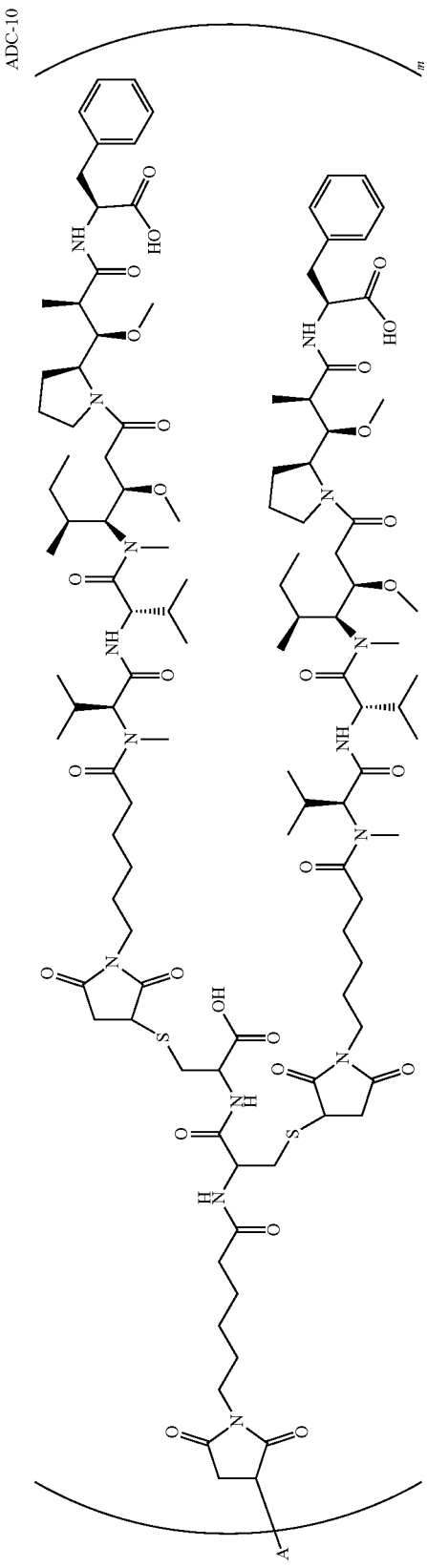

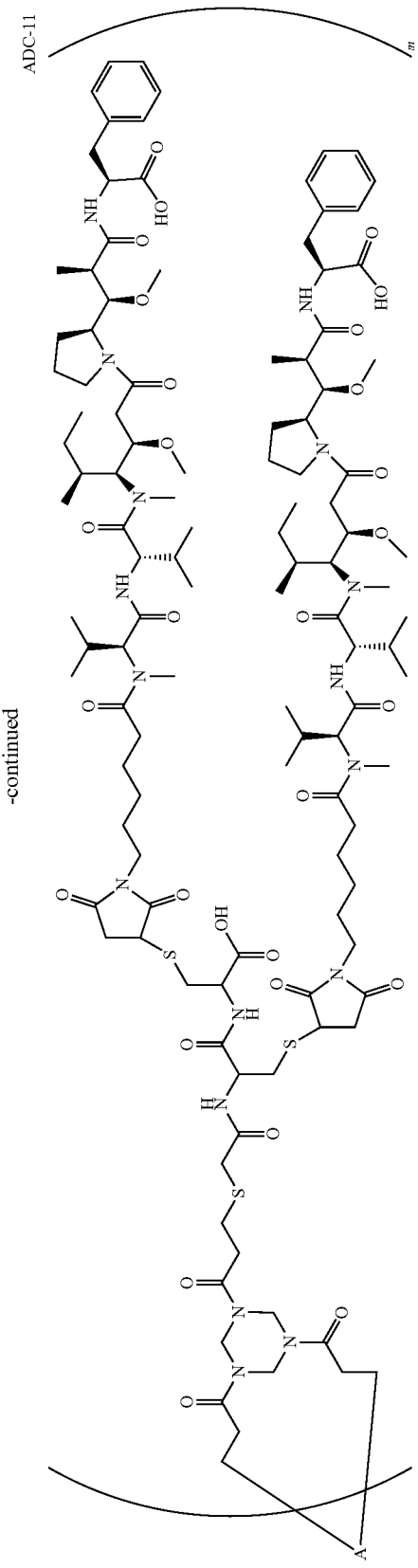

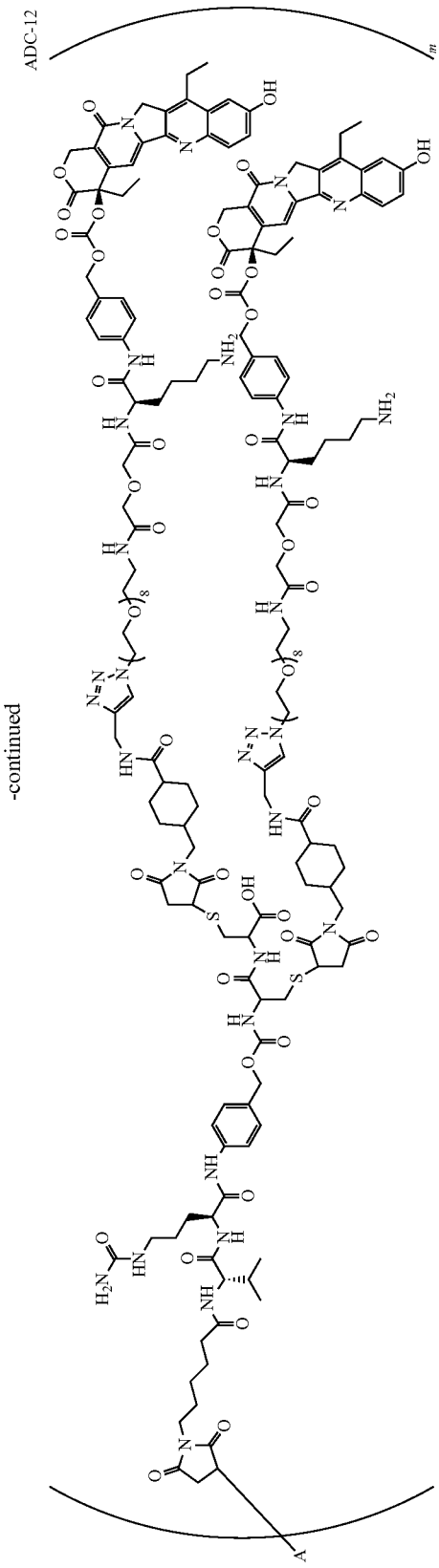
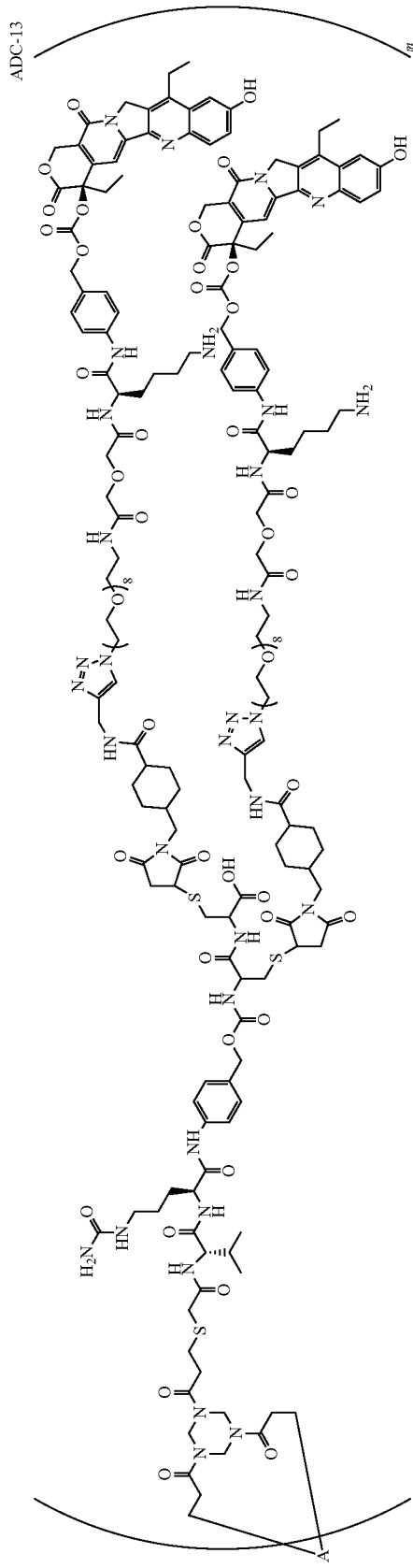

-continued
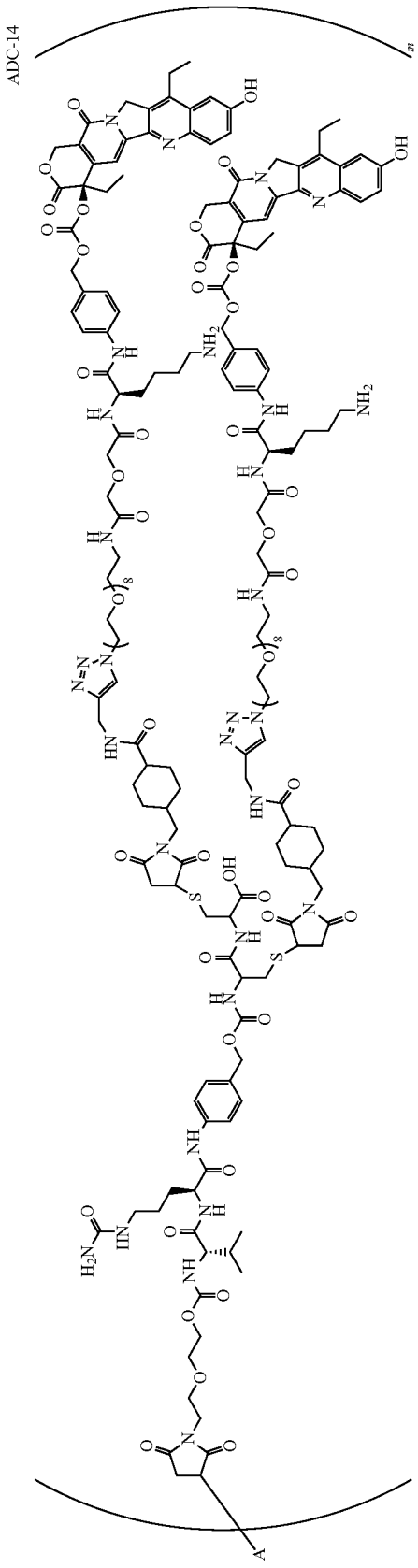
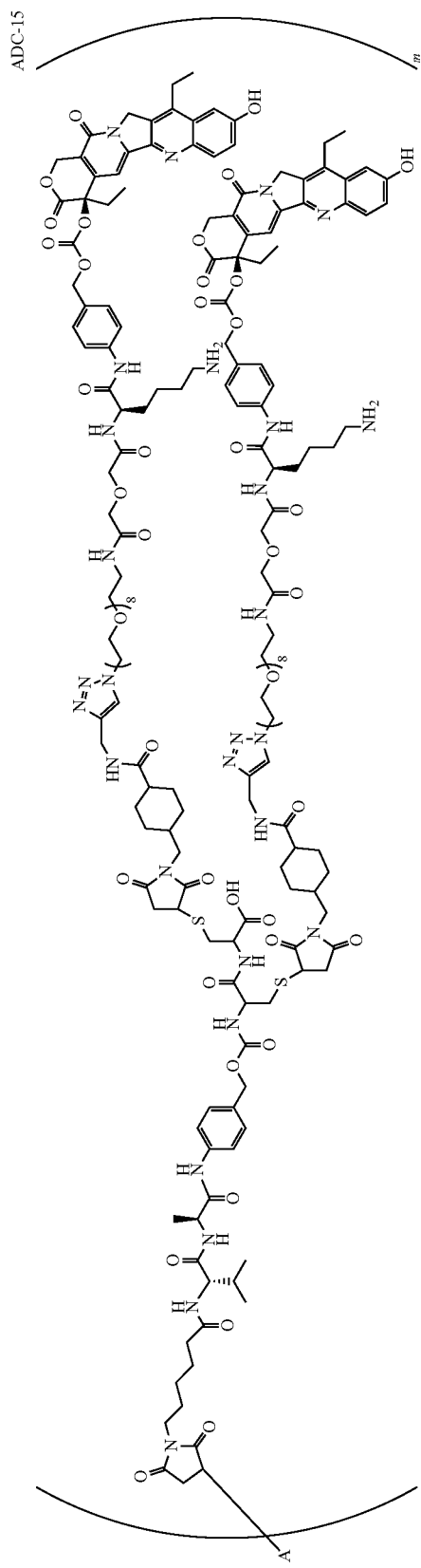

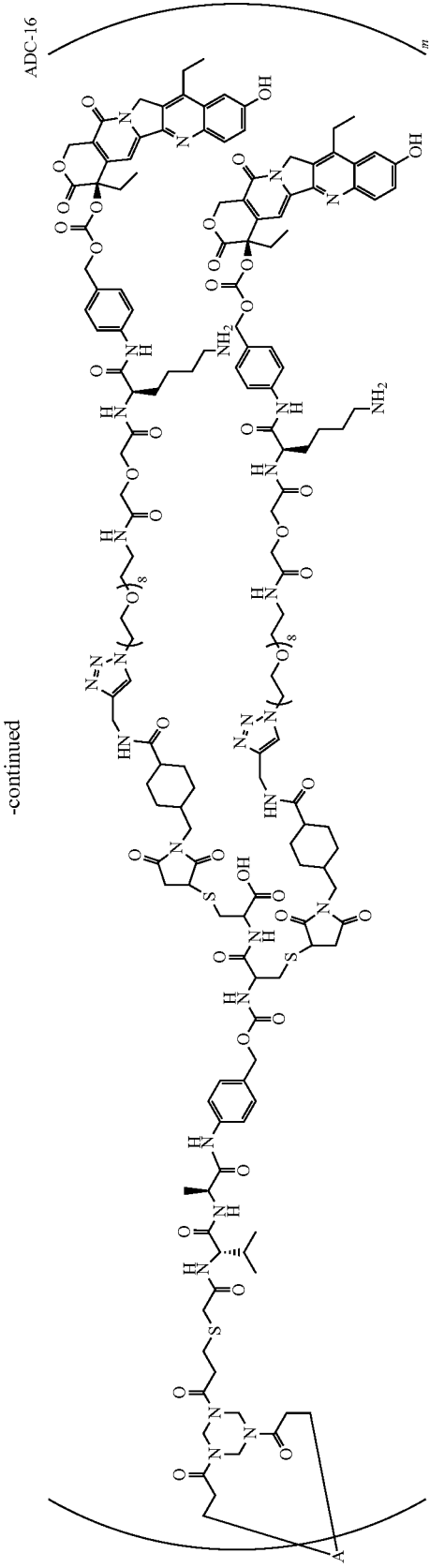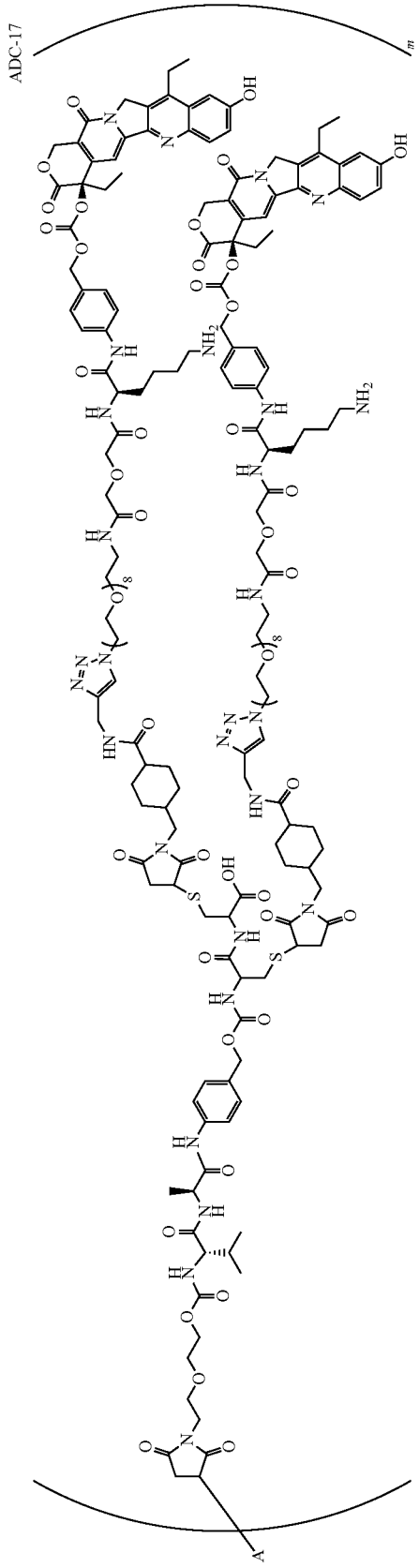

-continued
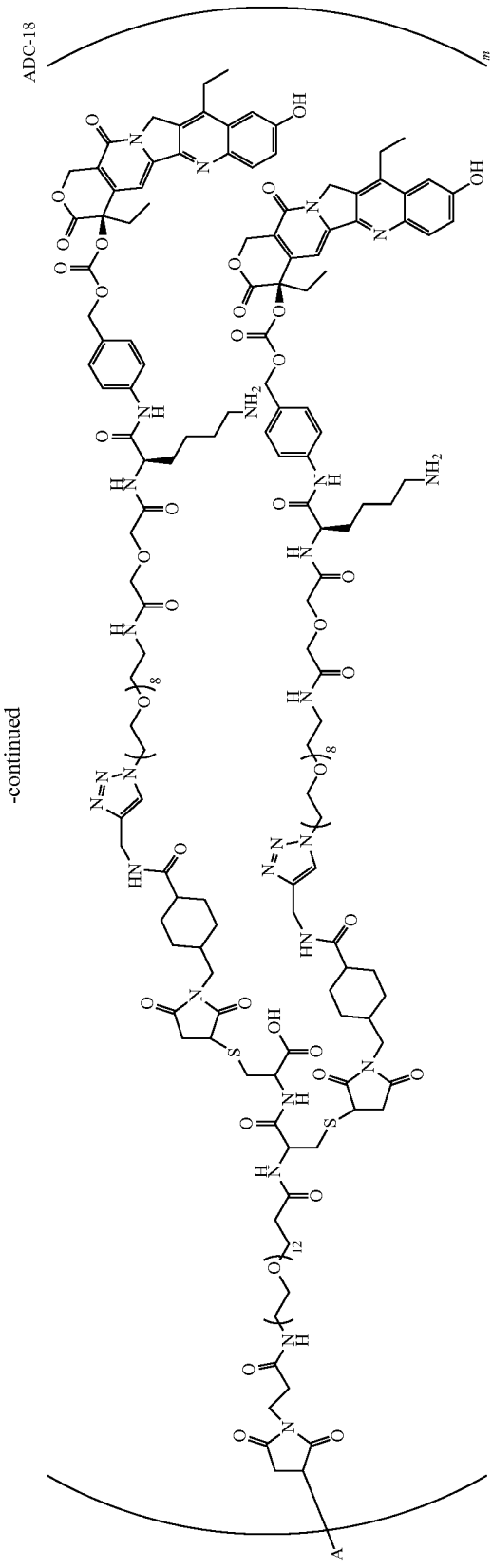
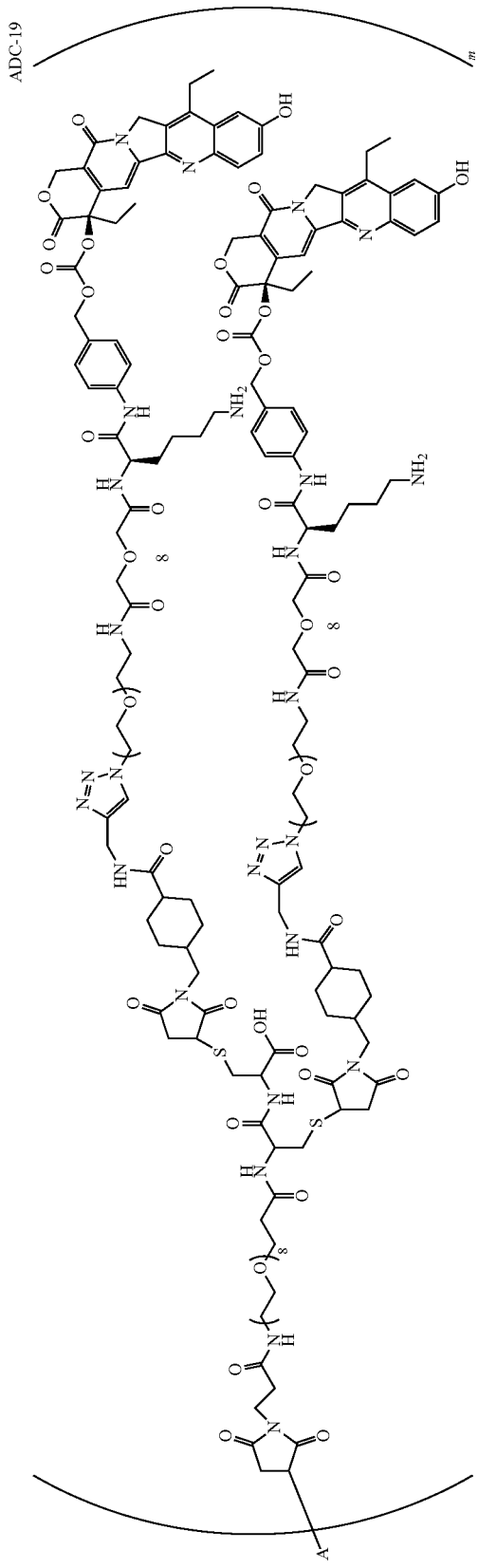

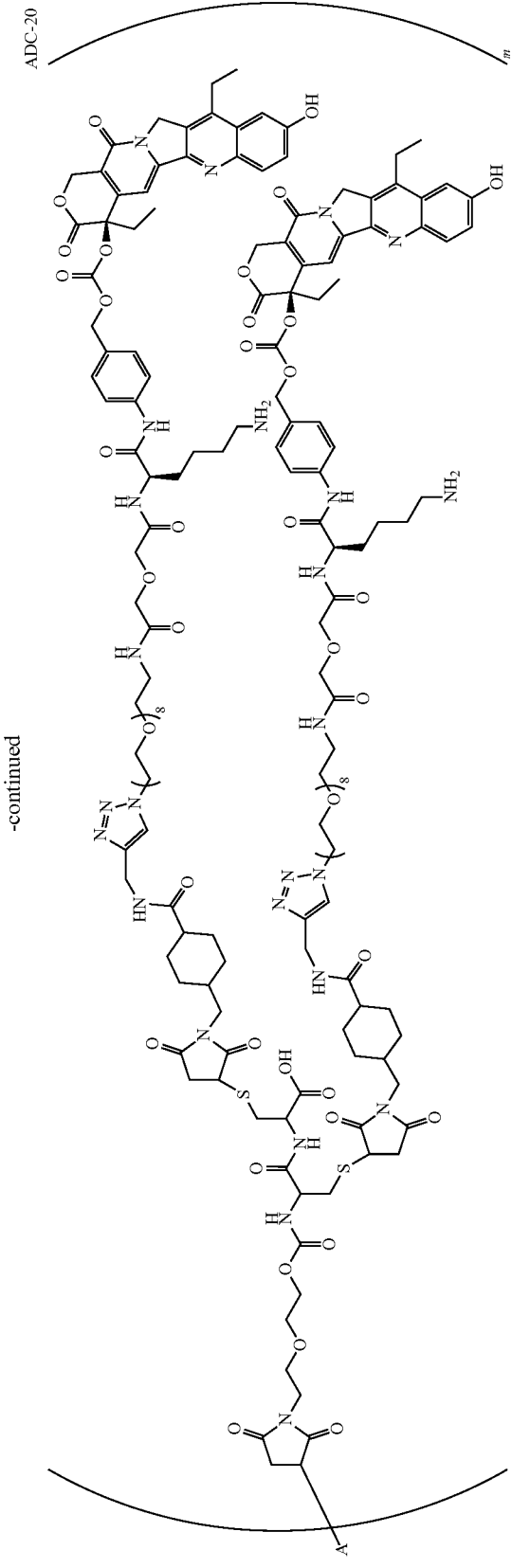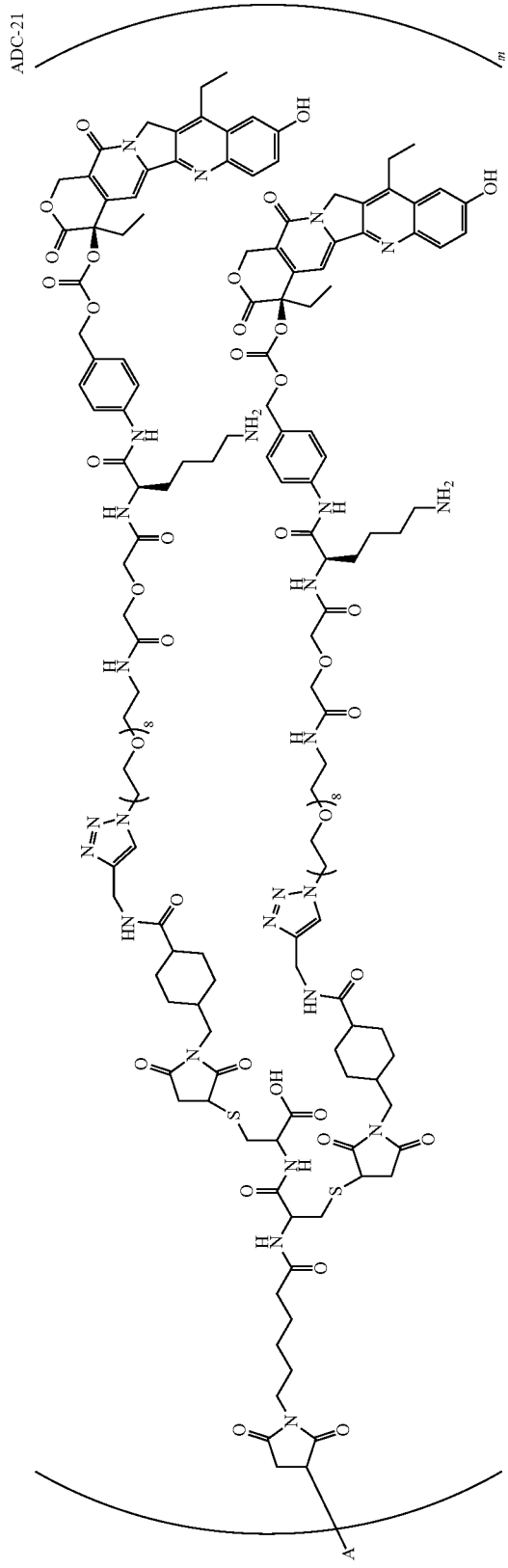

-continued
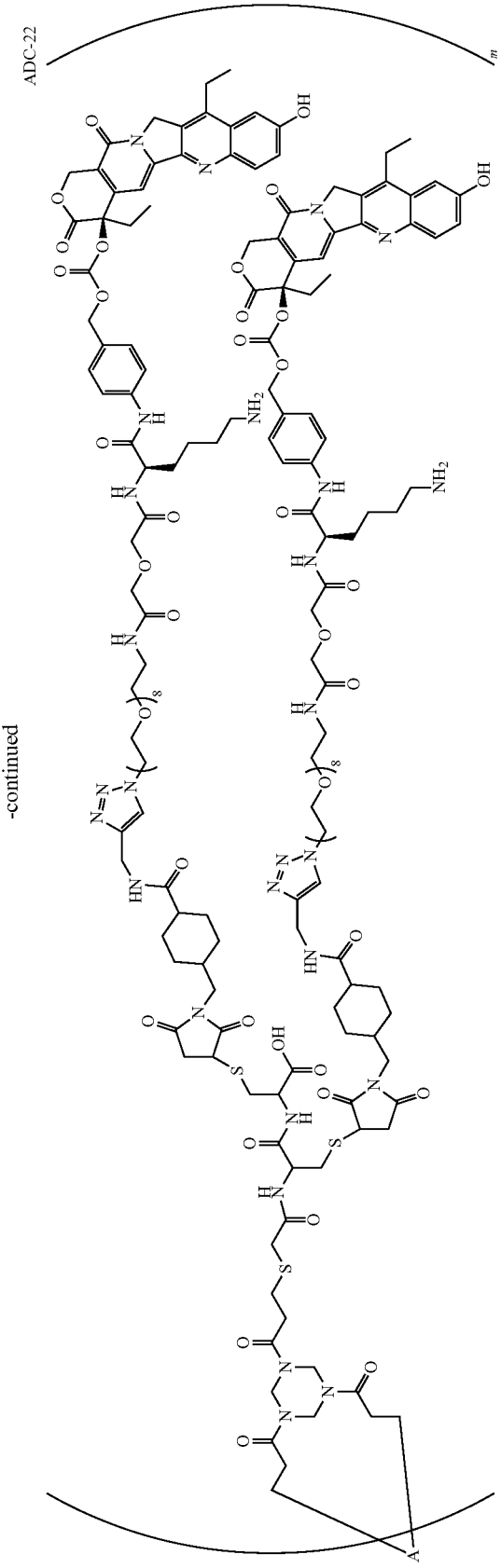

-continued
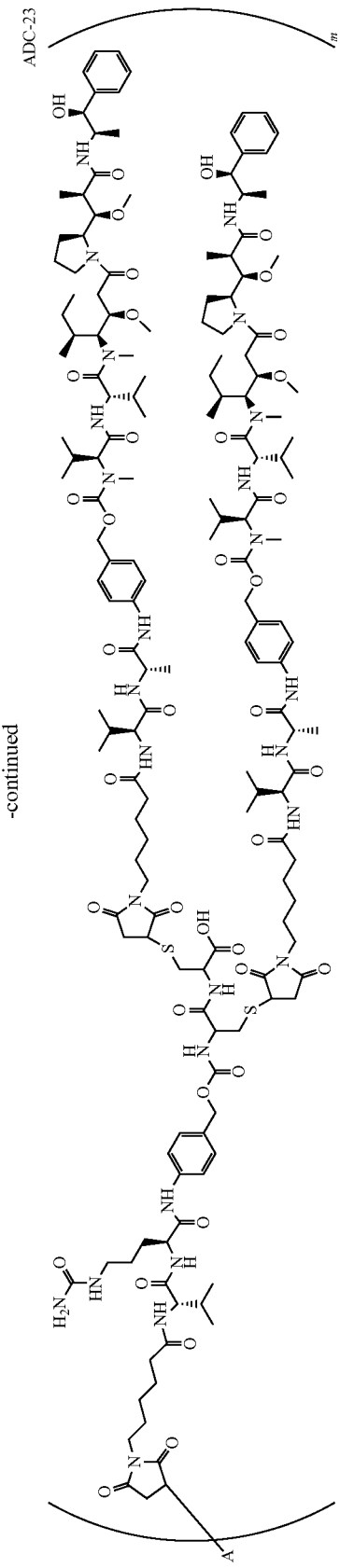
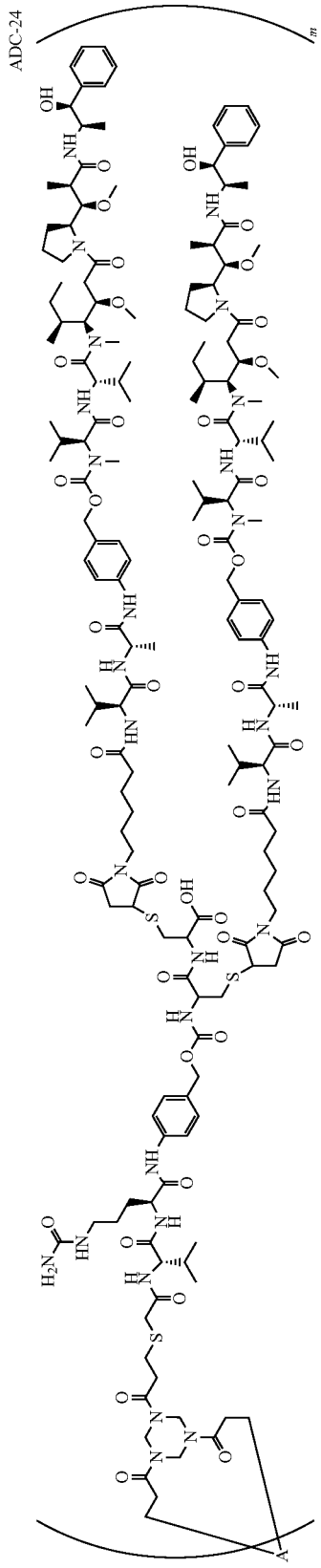

-continued
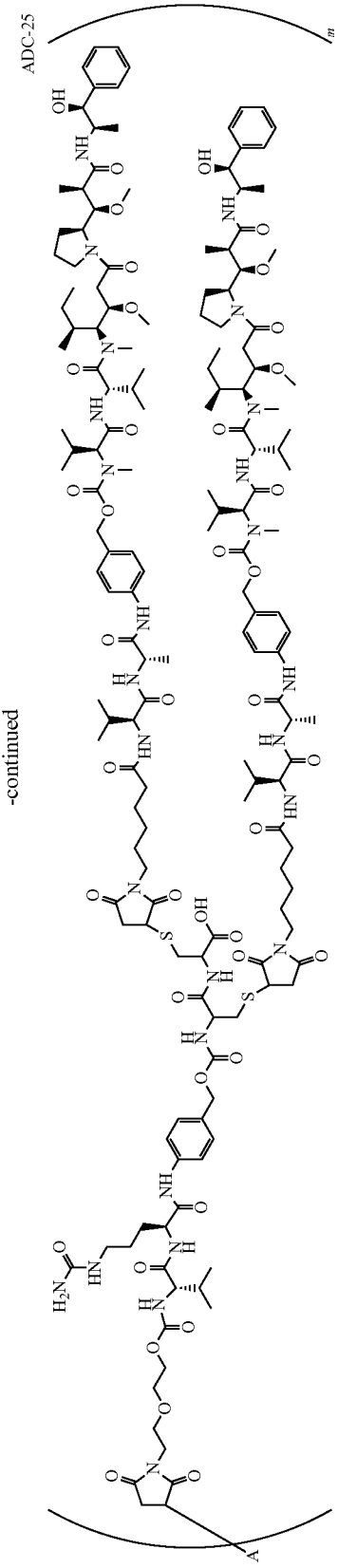
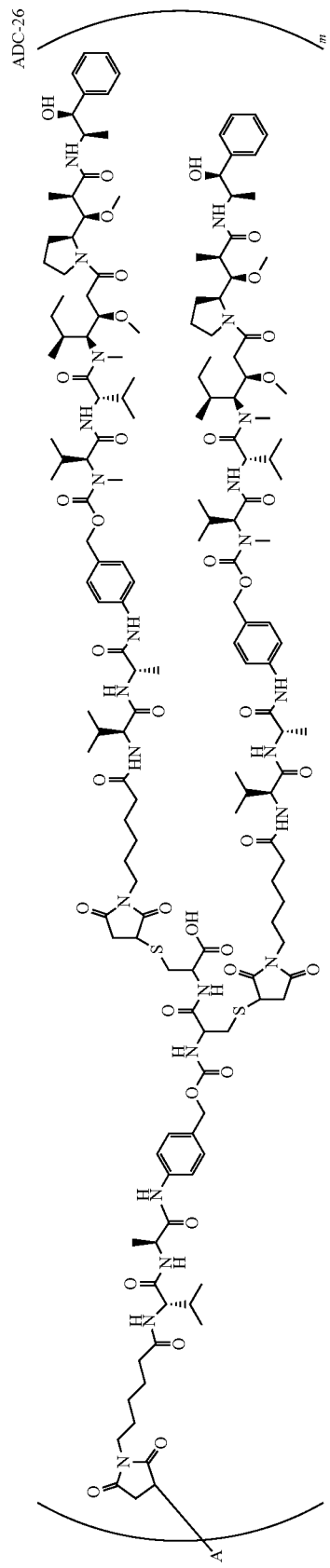

-continued
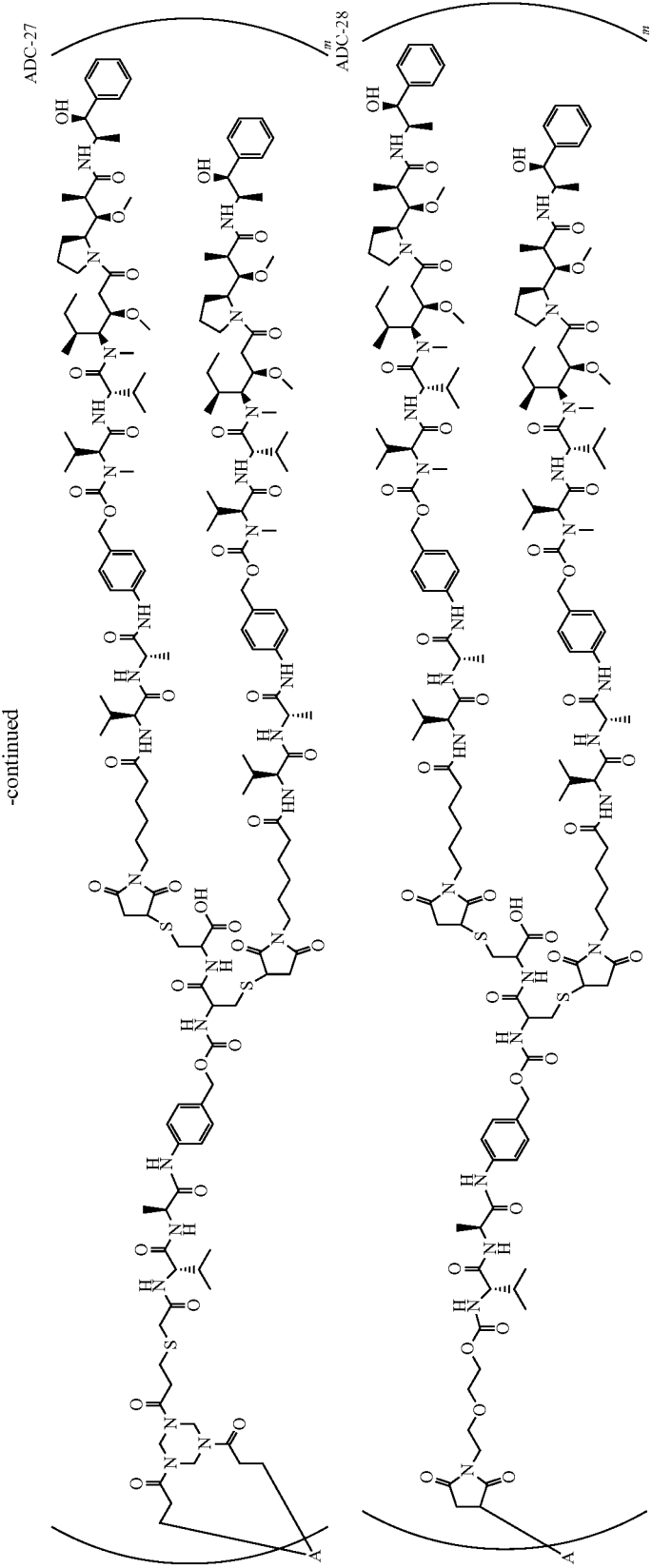

-continued
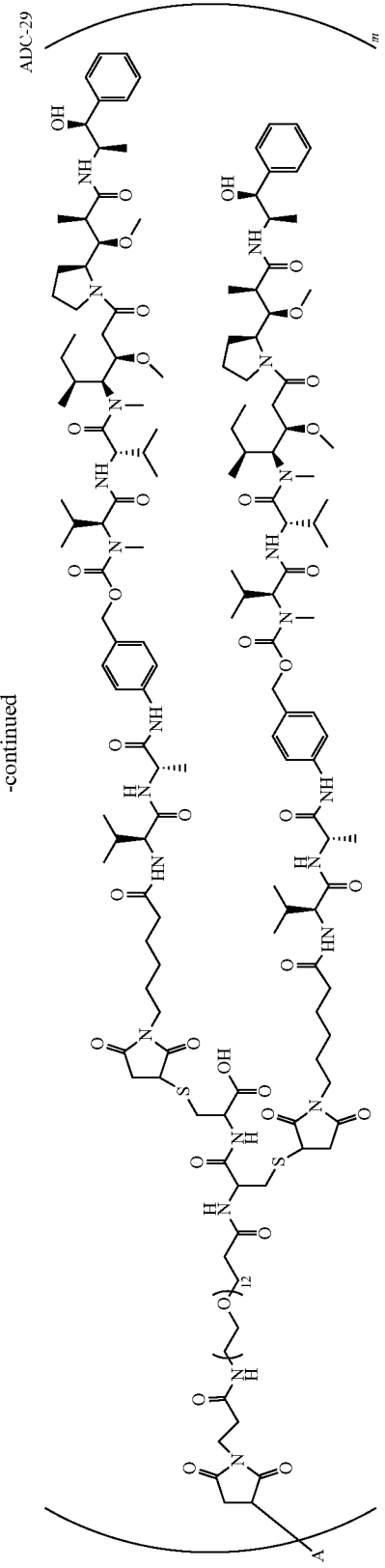
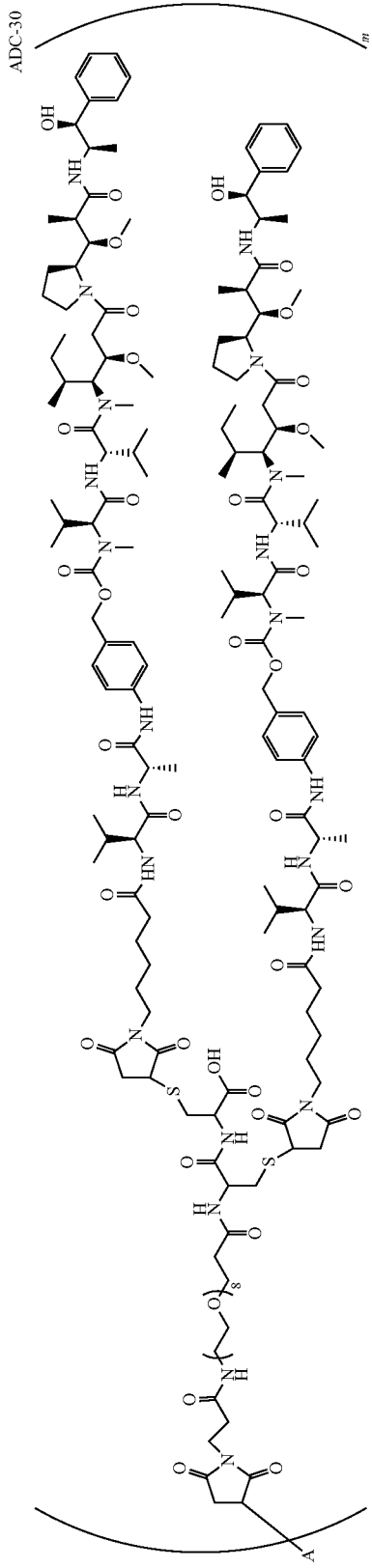

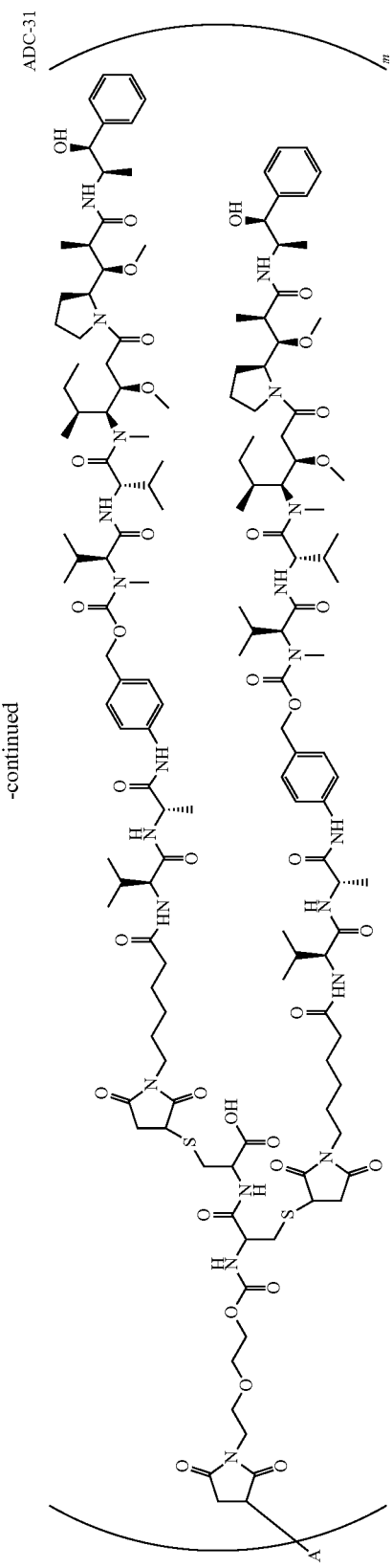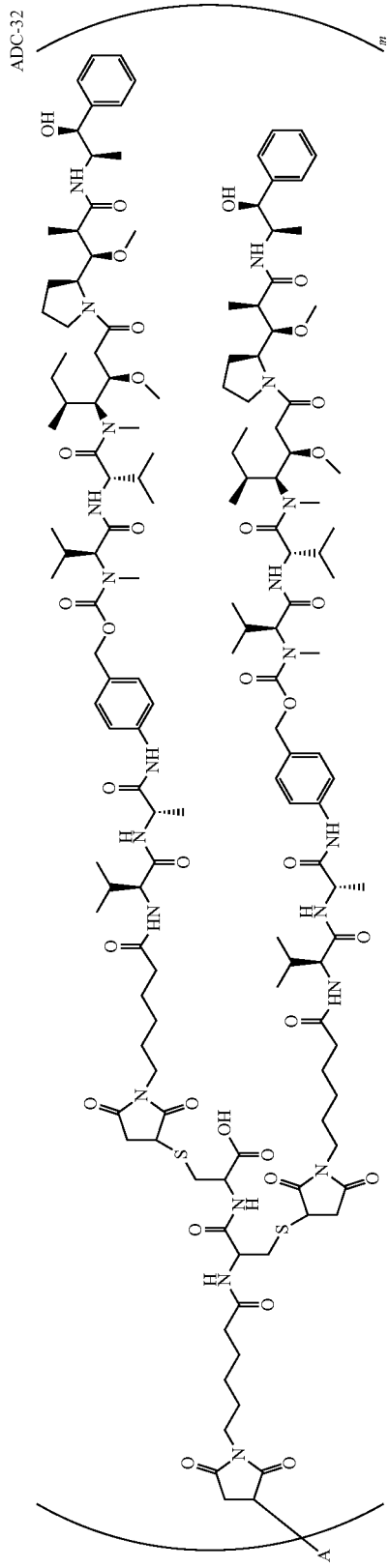

-continued
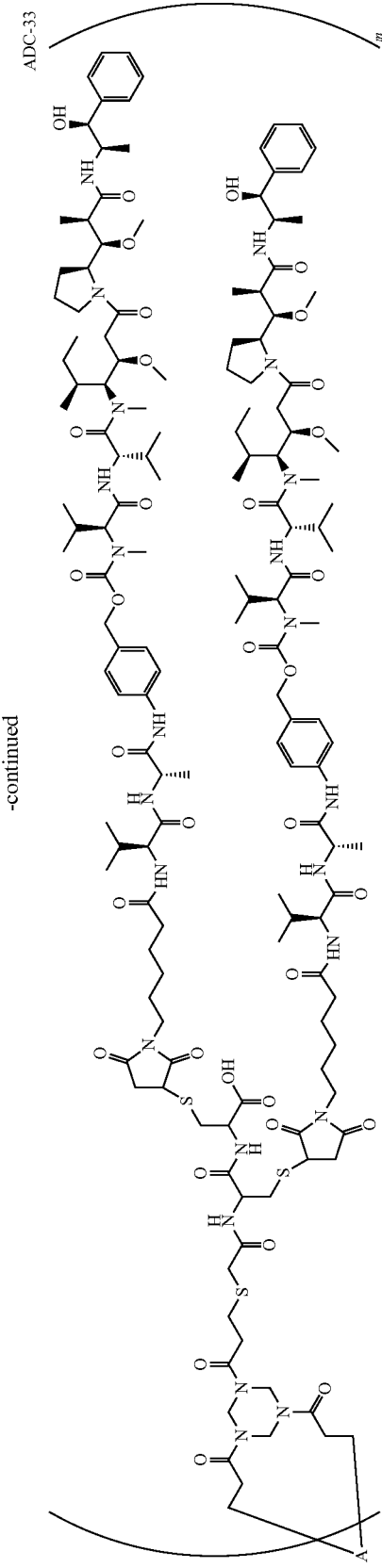
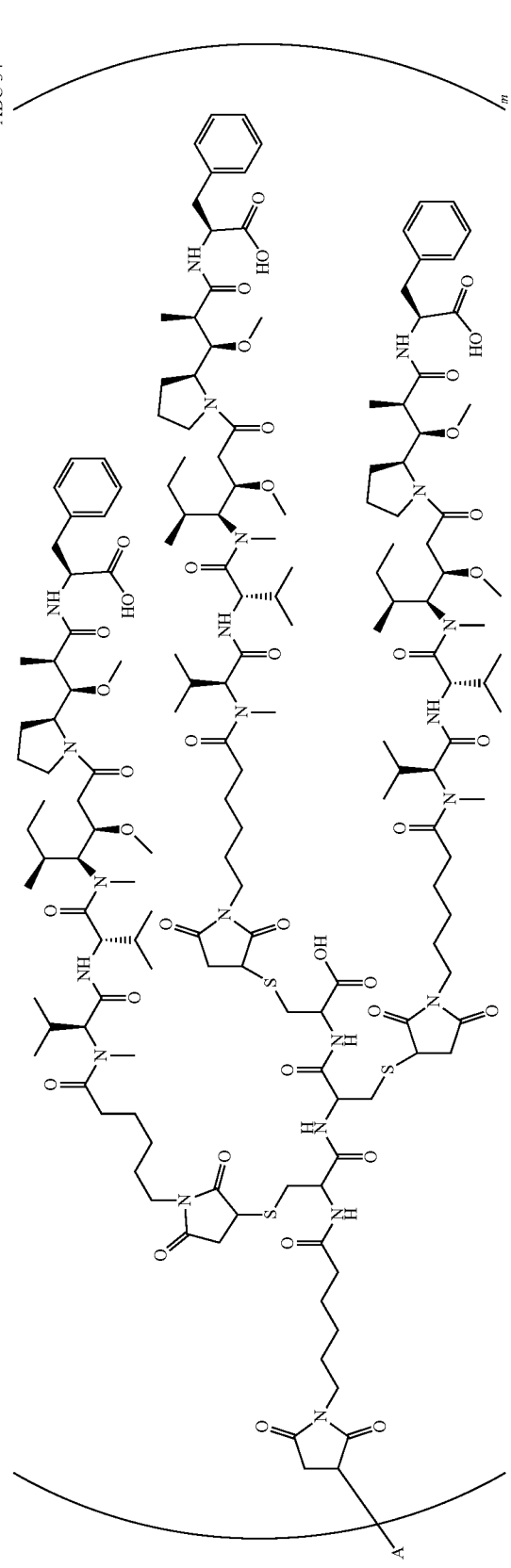

wherein
A is an antibody or a functional binding fragment thereof; and
m is selected from the group consisting of 1, 2, 3, 4, 5, 6, 7 and 8.

13. A pharmaceutical composition comprising an effective amount of the antibody-drug conjugate according to claim 1, or a pharmaceutically acceptable salt or solvate thereof, together with a pharmaceutically acceptable excipient.

14. A method for the treatment of cancer comprising administering the antibody-drug conjugate according to claim 1 to a subject in need thereof.

15. The antibody-drug conjugate according to claim 1, wherein $L_1$ is covalently linked to a thiol group of the antibody.

16. The antibody-drug conjugate according to claim 1, wherein $L_1$, $L_2$, $L_3$, $L_4$, ..., and $L_{n+1}$ are a non-cleavable linker.

17. The antibody-drug conjugate according to claim 10, wherein the tubulin inhibitor is selected from the group consisting of a cytotoxic molecule of dolastatins and auristatins, and a cytotoxic molecule of maytansines; the DNA damaging agent is selected from the group consisting of calicheamicins, duocarmycins, pyrrolobenzodiazepine (PBD), camptothecins, and SN-38.

18. The antibody-drug conjugate according to claim 10, wherein the cytokine molecule of auristatins is selected from the group consisting of MMAE and MMAF; and the cytotoxic molecule of maytansines is selected from the group consisting of DM1 and DM4.

19. The antibody-drug conjugate according to claim 10, wherein the cytotoxic molecule is selected from the group consisting of:

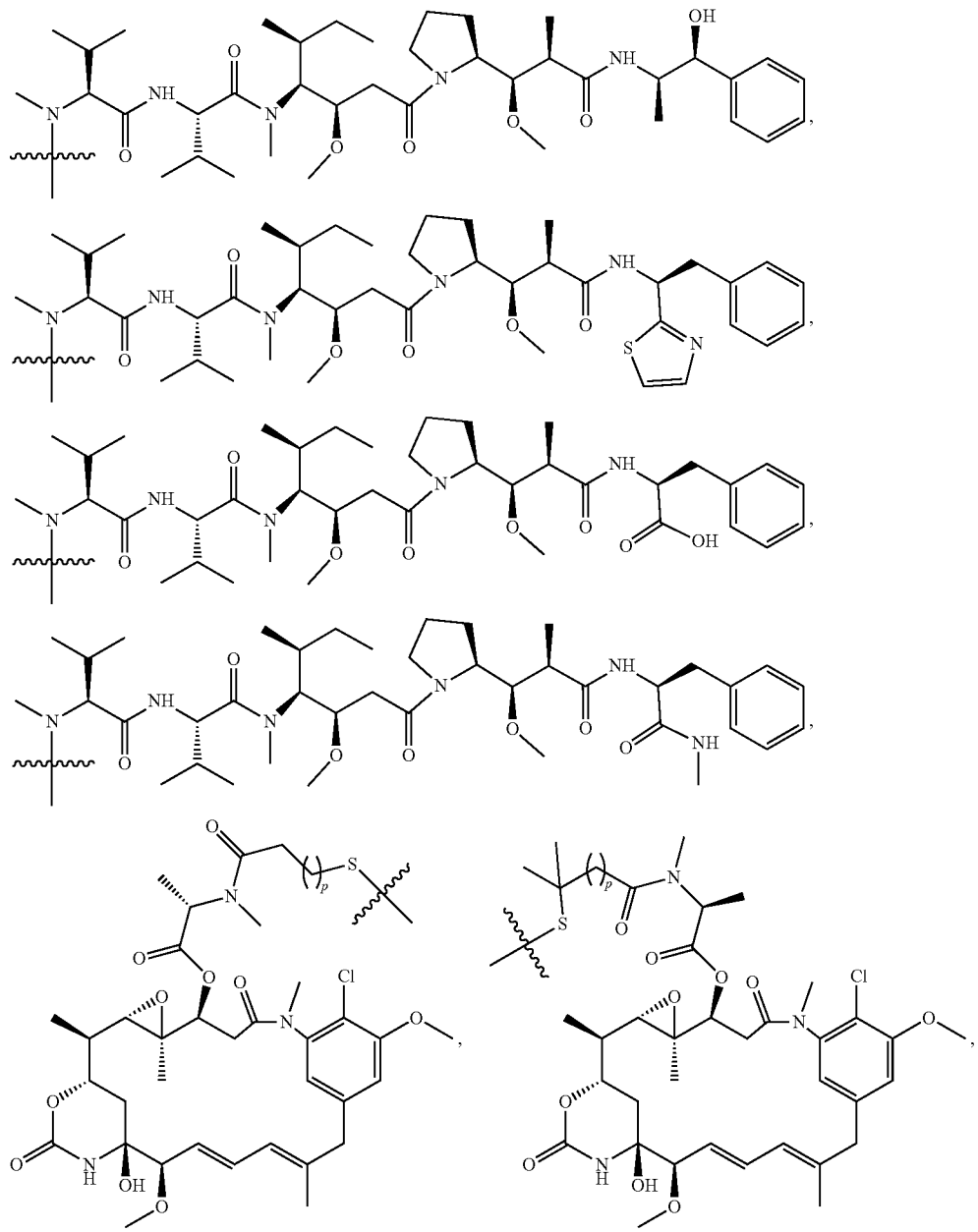

-continued
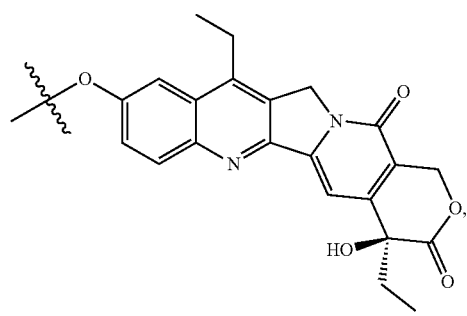
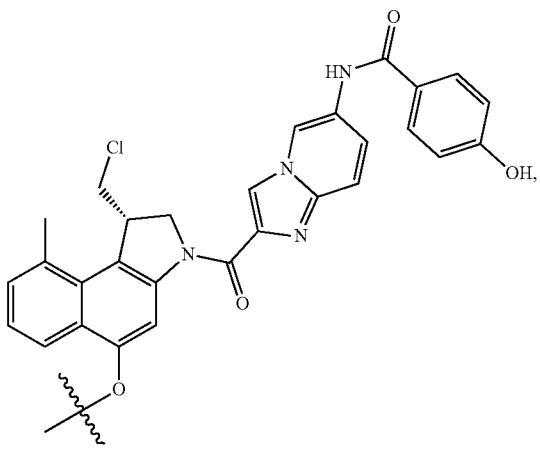
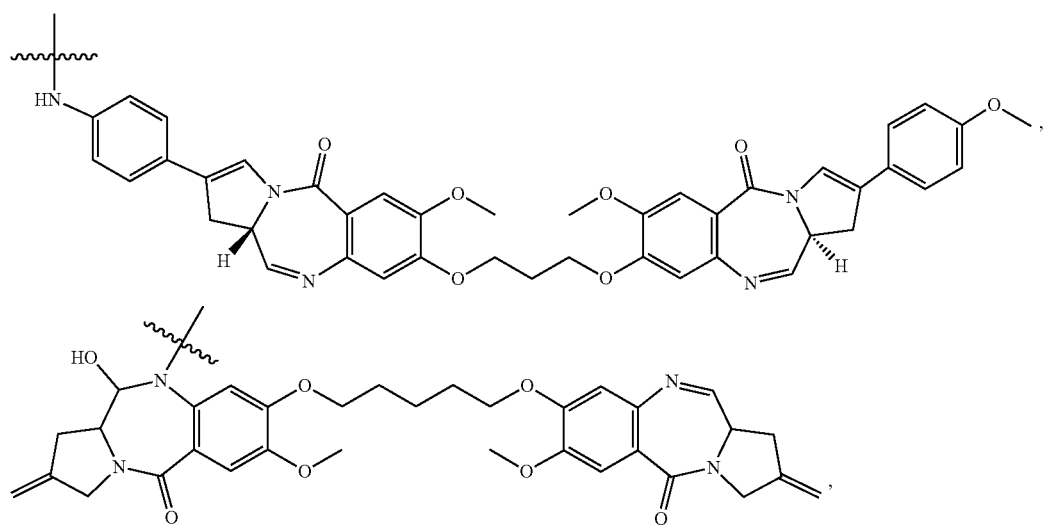
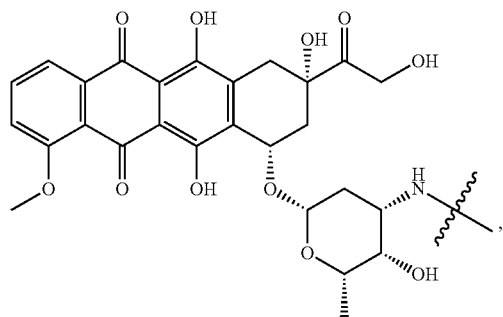
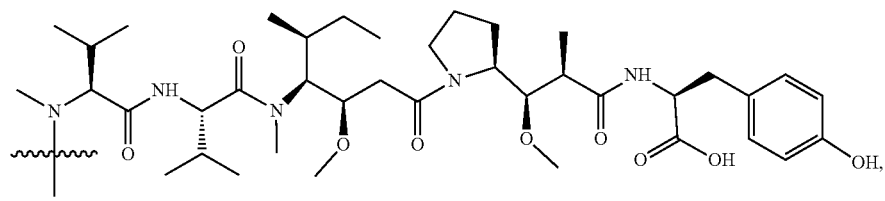

-continued
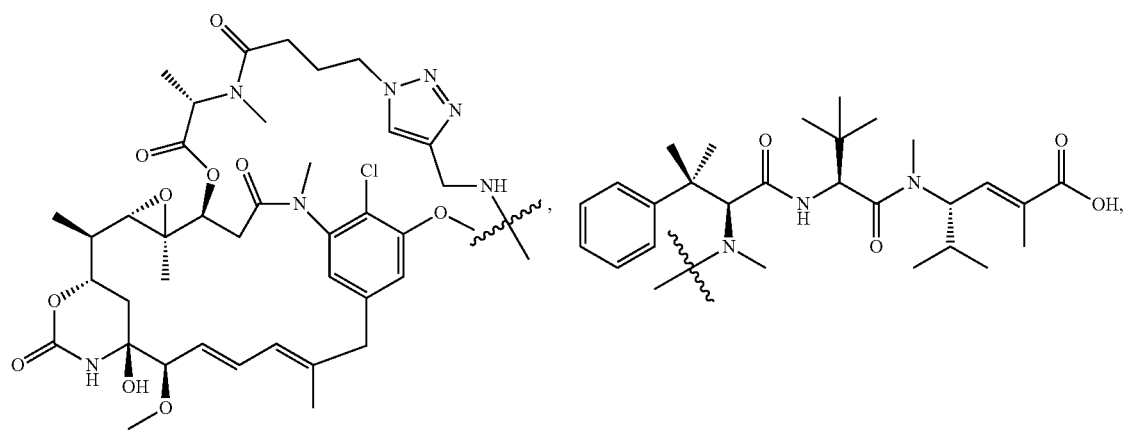
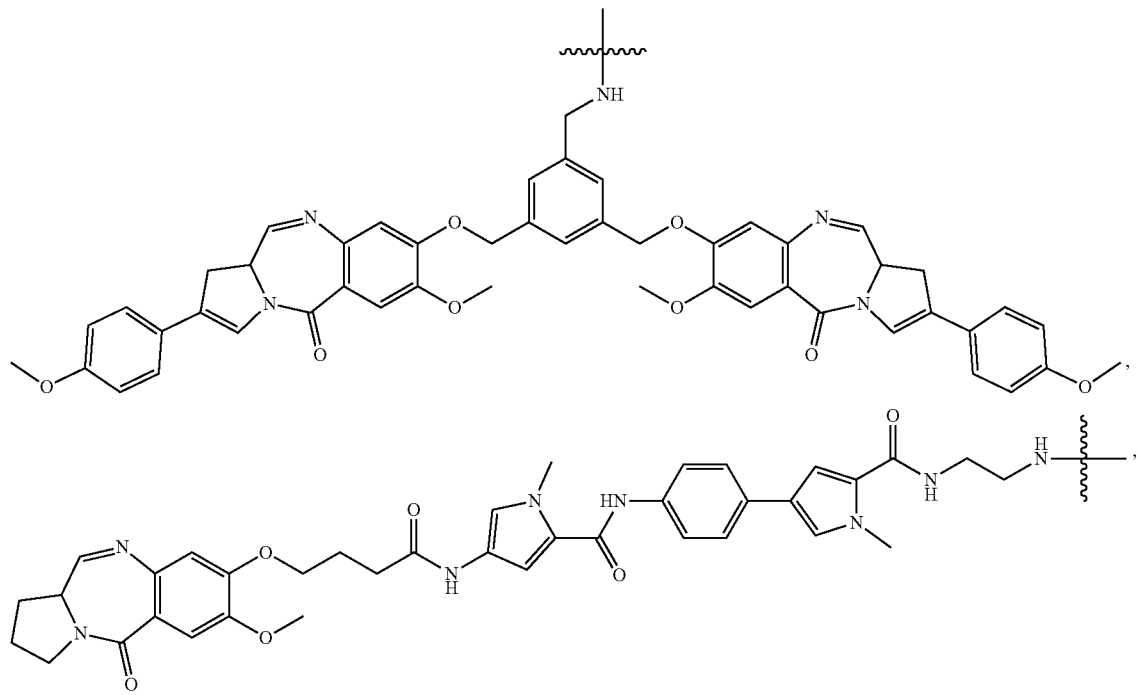
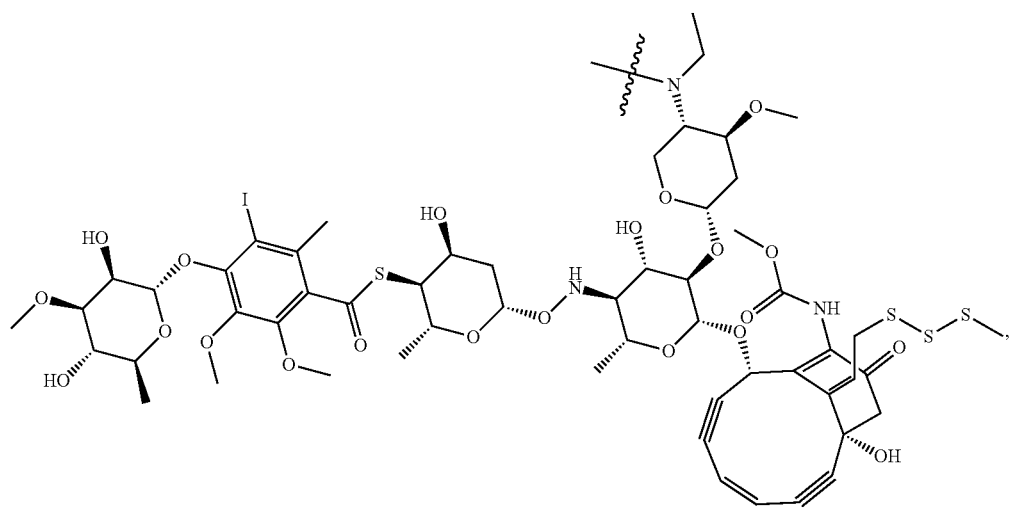

-continued
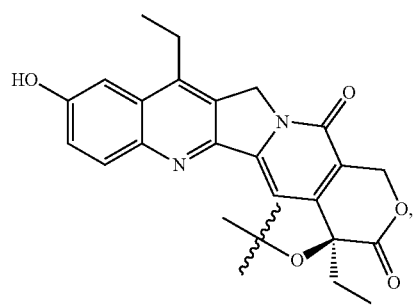
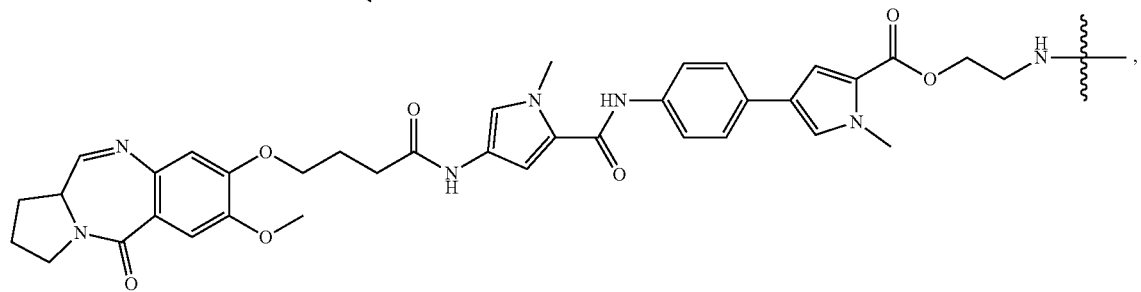
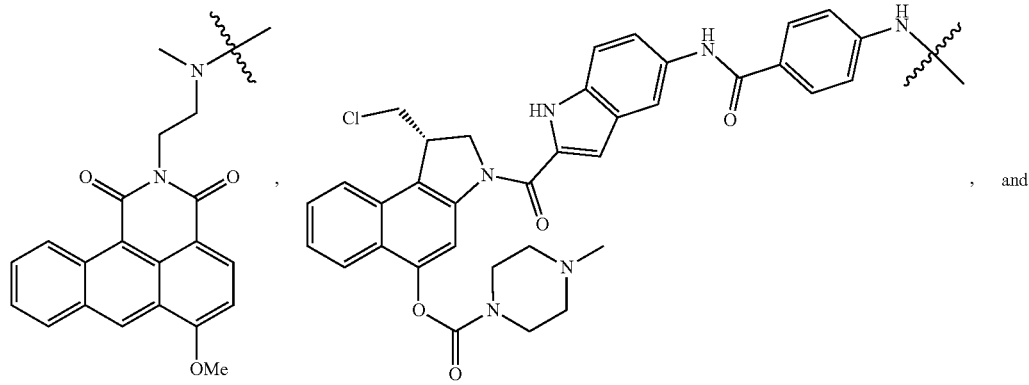, and
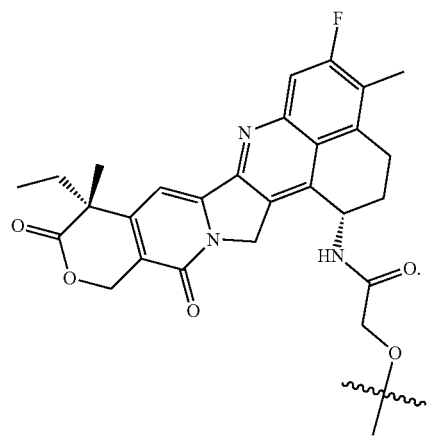 [SMILES: *OCC(=O)N[C@H]1CCc2c(C)c(F)cc3nc4c(c1c23)Cn1c-4cc2c(c1=O)COC(=O)[C@]2(C)CC]
* * * * *